US010456244B2

(12) United States Patent
Annest

(10) Patent No.: US 10,456,244 B2
(45) Date of Patent: *Oct. 29, 2019

(54) DEVICE AND METHOD FOR TEMPORARY OR PERMANENT SUSPENSION OF AN IMPLANTABLE SCAFFOLDING CONTAINING AN ORIFICE FOR PLACEMENT OF A PROSTHETIC OR BIO-PROSTHETIC VALVE

(71) Applicant: Lon Sutherland Annest, New York, NY (US)

(72) Inventor: Lon Sutherland Annest, New York, NY (US)

(*) Notice: Subject to any disclaimer, the term of this patent is extended or adjusted under 35 U.S.C. 154(b) by 236 days.

This patent is subject to a terminal disclaimer.

(21) Appl. No.: 15/460,954

(22) Filed: Mar. 16, 2017

(65) Prior Publication Data
US 2017/0181851 A1 Jun. 29, 2017

Related U.S. Application Data

(63) Continuation of application No. 14/669,728, filed on Mar. 26, 2015, now Pat. No. 9,622,858, which is a
(Continued)

(51) Int. Cl.
*A61F 2/24* (2006.01)
*A61B 17/04* (2006.01)
*A61B 17/00* (2006.01)

(52) U.S. Cl.
CPC ........ *A61F 2/2409* (2013.01); *A61B 17/0469* (2013.01); *A61F 2/246* (2013.01); *A61F 2/2418* (2013.01); *A61F 2/2436* (2013.01); *A61F 2/2439* (2013.01); *A61F 2/2457* (2013.01); *A61B 2017/003* (2013.01); *A61B 2017/00243* (2013.01); *A61B 2017/00349* (2013.01);
(Continued)

(58) Field of Classification Search
CPC .... A61F 2/2466; A61F 2/2409; A61F 2/2418; A61F 2/2427; A61F 2/2445; A61F 2/246
See application file for complete search history.

(56) References Cited

U.S. PATENT DOCUMENTS 6,419,696 B1 * 7/2002 Ortiz ............... A61F 2/2409
623/2.37
6,964,684 B2 11/2005 Ortiz et al.
(Continued)

FOREIGN PATENT DOCUMENTS

| EP | 2416739 | 2/2012 |
| WO | WO 2008/068756 A2 | 6/2008 |
| WO | WO2010/117471 | 10/2010 |

*Primary Examiner* — Thomas M McEvoy
(74) *Attorney, Agent, or Firm* — R. Neil Sudol; Henry D. Coleman

(57) ABSTRACT

In a surgical method for improving cardiac function, an implantable scaffold or valve support device is inserted inside a patient's heart and attached to the heart in a region adjacent to a natural mitral or other heart valve. The scaffold or valve support device defines an orifice and, after the attaching of the scaffold or valve support device to the heart, or temporary support while native valve leaflets and/or subvalvular structures are captured, a prosthetic or bio-prosthetic valve seated in the orifice, and the native valve may be retracted into the scaffold/replacement assembly to create a gasket for sealing the complex.

17 Claims, 34 Drawing Sheets

Related U.S. Application Data continuation of application No. 13/365,715, filed on Feb. 3, 2012, now Pat. No. 9,011,522, which is a continuation-in-part of application No. 12/798,629, filed on Apr. 8, 2010, now Pat. No. 8,986,370.

(60) Provisional application No. 61/168,279, filed on Apr. 10, 2009, provisional application No. 61/439,734, filed on Feb. 4, 2011, provisional application No. 61/518,772, filed on May 11, 2011.

(52) U.S. Cl.
CPC ........... *A61B 2017/0409* (2013.01); *A61B 2017/0427* (2013.01); *A61B 2017/0441* (2013.01); *A61F 2/2412* (2013.01); *A61F 2220/0008* (2013.01); *A61F 2220/0016* (2013.01); *A61F 2250/0003* (2013.01); *A61F 2250/006* (2013.01)

(56) References Cited

U.S. PATENT DOCUMENTS

| | | | |
|---|---|---|---|
| 7,335,213 B1 * | 2/2008 | Hyde | A61B 17/0469 606/151 |
| 7,569,062 B1 | 8/2009 | Kuehn | |
| 7,887,583 B2 | 2/2011 | Macoviak | |
| 8,986,370 B2 | 3/2015 | Annest | |
| 9,011,522 B2 | 4/2015 | Annest | |
| 2001/0047150 A1 | 11/2001 | Chobotov | 604/107 |
| 2002/0029080 A1 | 3/2002 | Mortier et al. | |
| 2003/0083742 A1 | 5/2003 | Spence | |
| 2004/0044406 A1 | 3/2004 | Woolfson | |
| 2004/0167620 A1 | 8/2004 | Ortiz et al. | 623/2.11 |
| 2004/0236419 A1 | 11/2004 | Simcha | |
| 2005/0070999 A1 | 3/2005 | Spence | |
| 2005/0075727 A1 | 4/2005 | Wheatley | |
| 2005/0137702 A1 * | 6/2005 | Haug | A61F 2/2418 623/2.38 |
| 2006/0074484 A1 * | 4/2006 | Huber | A61B 17/22004 623/2.11 |
| 2006/0259135 A1 | 11/2006 | Navia et al. | |
| 2008/0039935 A1 | 2/2008 | Buch et al. | |
| 2008/0077235 A1 | 3/2008 | Kirson | |
| 2008/0125860 A1 | 5/2008 | Webler et al. | |
| 2008/0167713 A1 | 7/2008 | Bolling | |
| 2008/0262609 A1 | 10/2008 | Gross et al. | |
| 2009/0054969 A1 | 2/2009 | Salahieh et al. | |
| 2010/0042147 A1 | 2/2010 | Janovsky et al. | |
| 2010/0049315 A1 | 2/2010 | Kirson | |
| 2010/0070027 A1 | 3/2010 | Bonhoeffer et al. | |
| 2010/0161047 A1 | 6/2010 | Cabiri | |
| 2010/0262232 A1 | 10/2010 | Annest | |

* cited by examiner

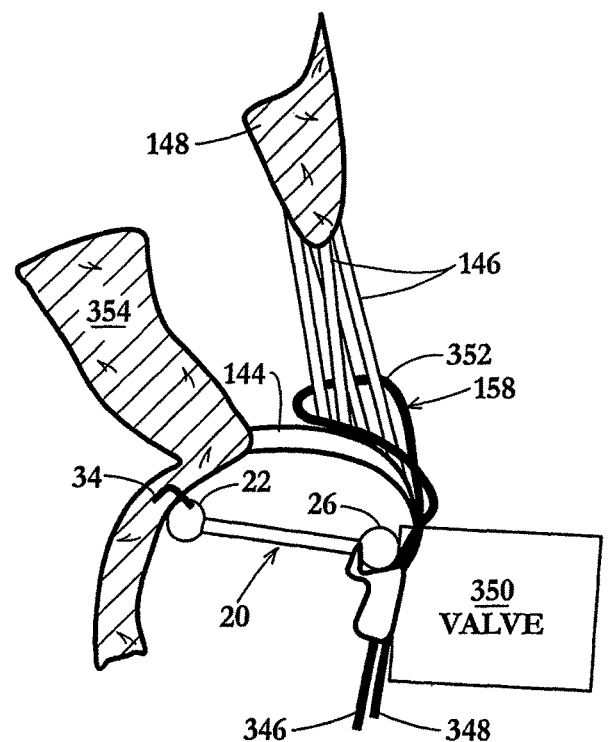
FIG. 38
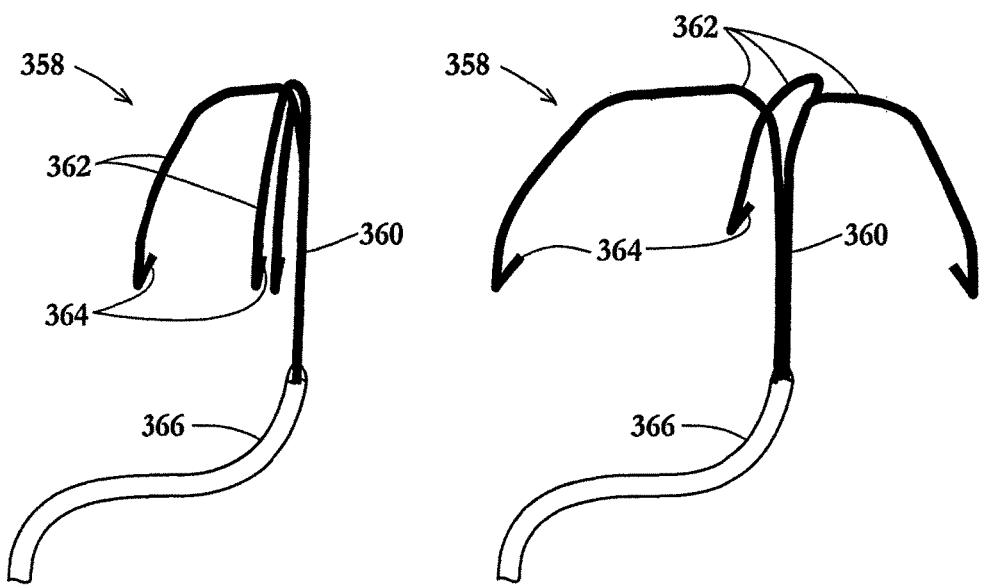
FIG. 39
FIG. 40

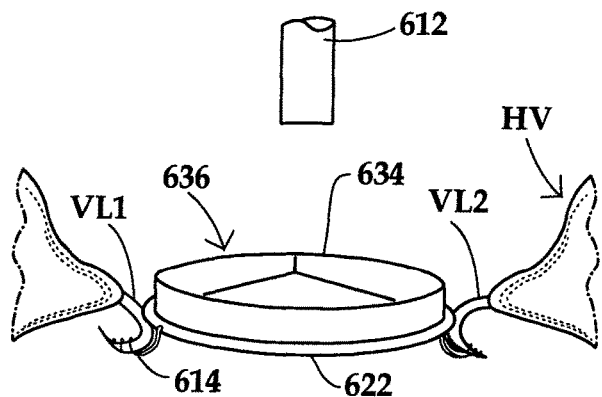
FIG. 62
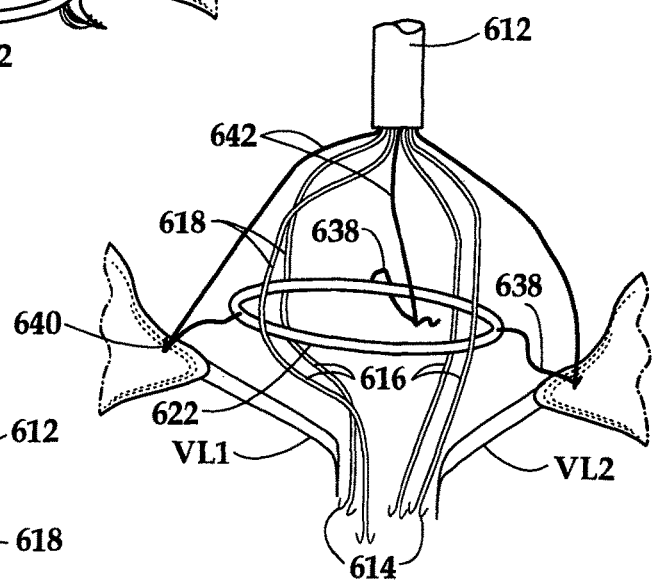
FIG. 63
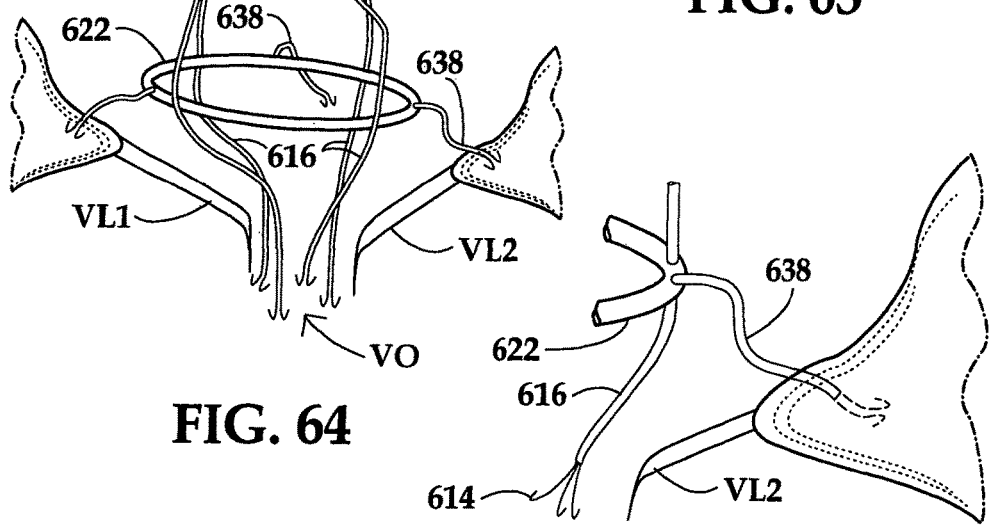
FIG. 64
FIG. 65

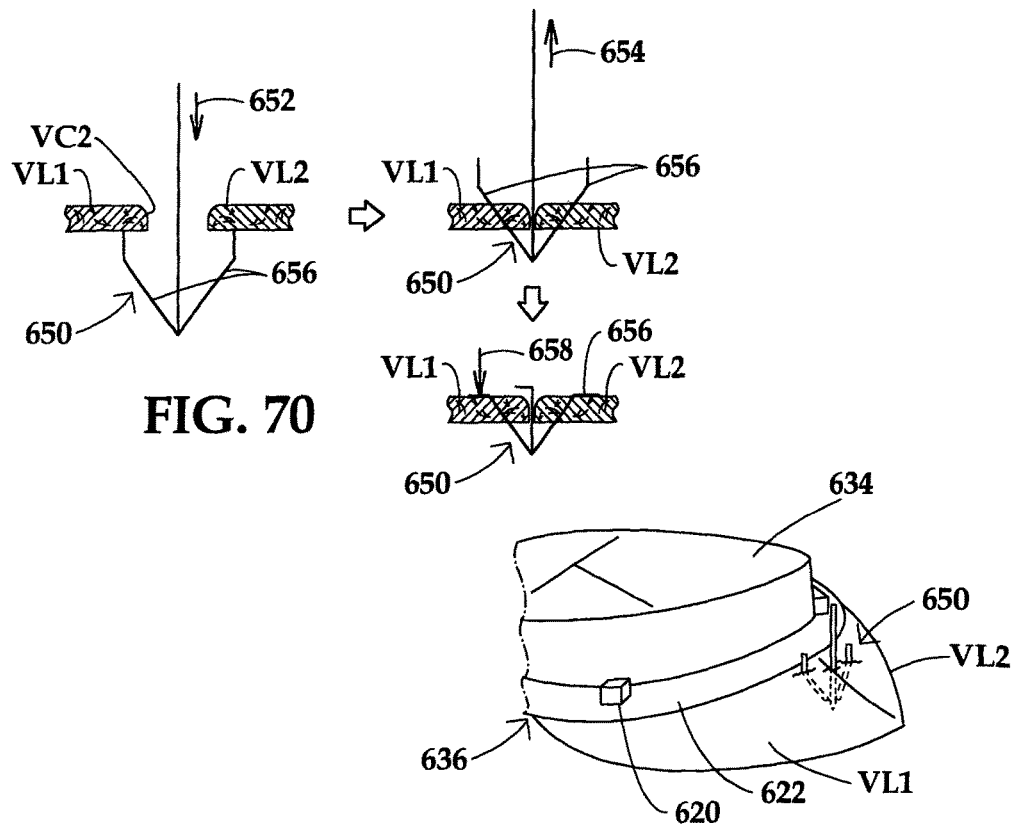
FIG. 70
FIG. 71
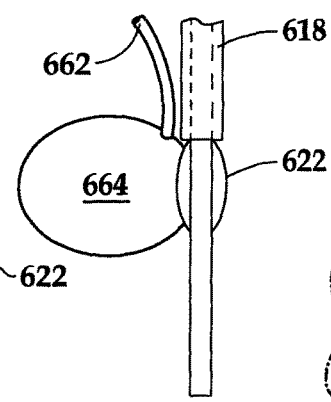
FIG. 72A  FIG. 72B
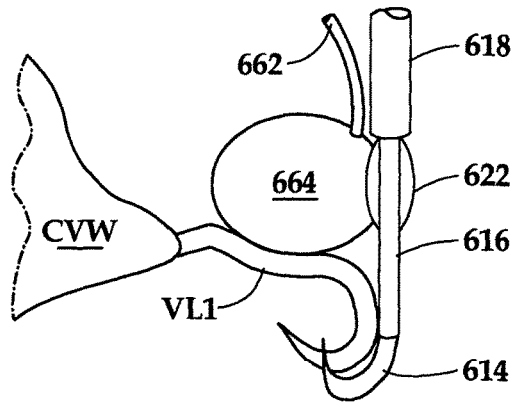
FIG. 73

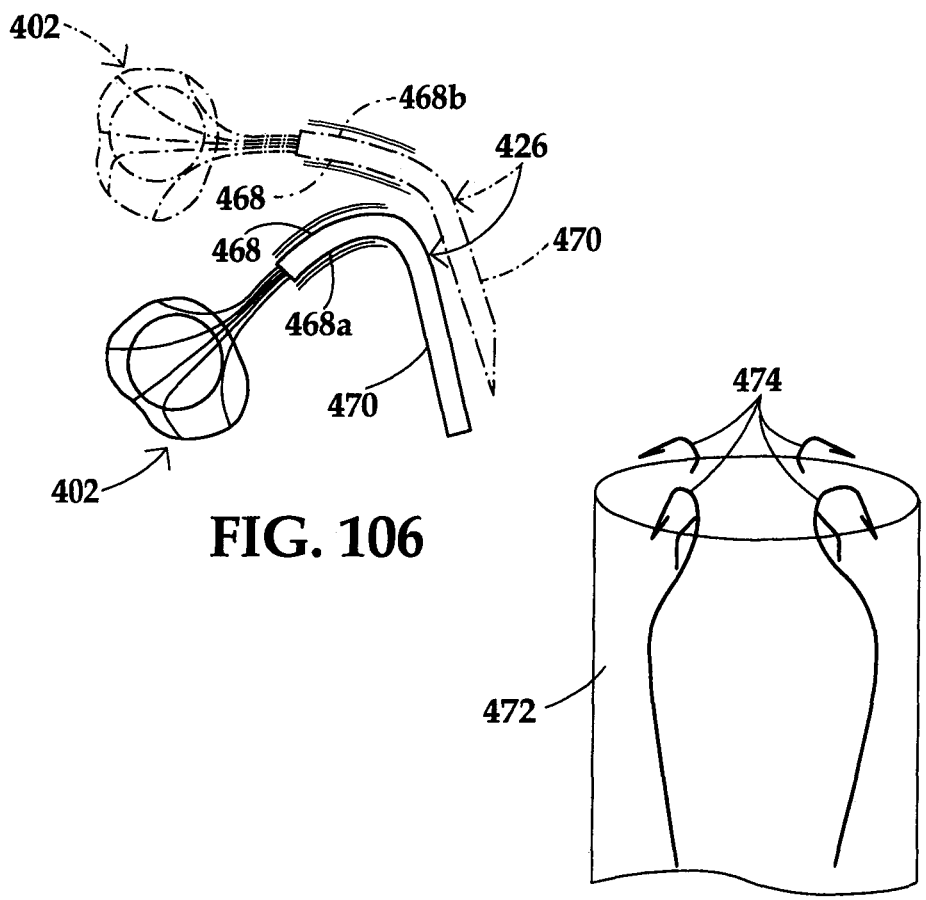
FIG. 106
FIG. 107
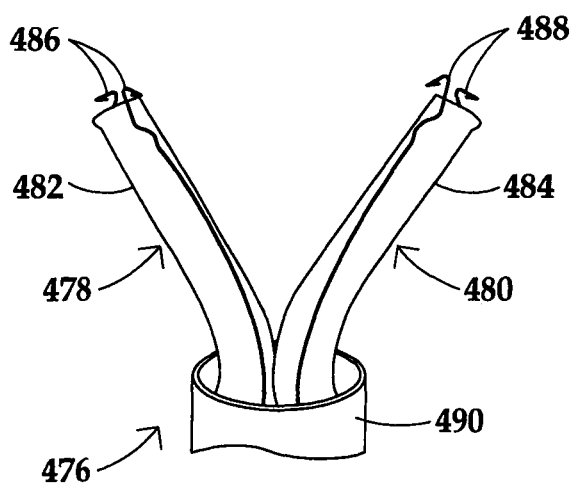
FIG. 108

DEVICE AND METHOD FOR TEMPORARY OR PERMANENT SUSPENSION OF AN IMPLANTABLE SCAFFOLDING CONTAINING AN ORIFICE FOR PLACEMENT OF A PROSTHETIC OR BIO-PROSTHETIC VALVE

CROSS-REFERENCE TO RELATED APPLICATIONS

This application is a continuation of U.S. patent application Ser. No. 14/669,728, now U.S. Pat. No. 9,622,864, filed Mar. 26, 2015 as a continuation of application Ser. No. 13/365,715, now U.S. Pat. No. 9,011,522, filed Feb. 3, 2012 as a continuation-in-part of U.S. patent application Ser. No. 12/798,629 filed Apr. 8, 2010 and claiming the benefit of U.S. Provisional Patent Application No. 61/168,279 filed Apr. 10, 2009. This application also claims the benefit of U.S. Provisional Patent Application No. 61/439,734 filed Feb. 4, 2011 and the benefit of U.S. Provisional Patent Application No. 61/518,772 filed May 11, 2011.

FIELD OF THE INVENTION

The present invention relates to medical devices and procedures, in particular related to the fixation within the heart or blood vessel of a device which enables replacement of a heart valve, and more particularly, to a novel device for use in a novel procedure for performing a catheter-based heart valve replacement.

BACKGROUND OF THE INVENTION

The four valves of the human heart consist of either two or three pliable leaflets attached circumferentially to a fibrous skeletal annulus. Normally, heart valves function to open in one portion of the cardiac cycle, either systole or diastole, (depending on the valve), causing minimal resistance to forward blood flow, but close by hinging from the annulus during the other part of the cardiac cycle, with the leaflets (either two or three) coming into central contact with each other, such that retrograde flow is inhibited.

Heart valve regurgitation, or leakage occurs when the leaflets of the valve fail to come fully into contact. This can be congenital, or the result of a disease process. Regardless of the cause, the leakage interferes with heart function, since it allows the unintended flow of blood back through the valve. Depending on the degree of leakage, the backward flow can become a self-destructive influence on not only function, but also cardiac geometry. Alternatively, abnormal cardiac geometry can cause the leakage, and the two processes are "cooperative" in causing acceleration of abnormal cardiac function.

The result of a valve having significant regurgitation is that a pathological state develops in which blood may be simultaneously pumped both forward through the outflow valve of a chamber and backward through the inflow valve, decreasing forward cardiac output. Depending on the severity of the leakage, the capability and efficiency of the heart to pump adequate blood flow can be compromised. In the case of the two trio-ventricular valves, (the mitral and tricuspid), the process can be caused by myocardial infarction damaging papillary muscles located in the left (or right) ventricle, torn or abnormally elongated chordae tendineae, or in any valve through damaged valve structures by infection, degenerative processes, or stretching of the annulus such that leaflets no longer come into contact by virtue of the increased cross-sectional area. Stretching of the ventricle and increased distance between the papillary muscles can also cause leakage of the atrio-ventricular (A/V) valves.

At present, for the most part, regurgitant valves can be either surgically repaired or replaced, both currently requiring open-heart surgery, use of cardio-pulmonary bypass and stoppage of the heart. Because of the magnitude of the procedure, risk of death, stroke, and bleeding, respiratory, renal, and other complications is significant enough that many patients are not candidates for treatment. The heart or aorta must be cut open, and even when performed by very experienced surgeons, repairs can fail early, or, if initially successful, are not always durable over time.

In the case of the mitral valve, replacement with a prosthetic or bio-prosthetic valve is associated with a higher operative mortality than repair of the native valve, but does not result in recurrent regurgitation experienced after a repair. The higher mortality is thought to be the result of loss of the function of the papillary muscles of the left ventricle, which are attached to the mitral valve leaflets by cords known as chordae tendineae, which contribute to tethering of the leaflets and systolic shortening of the left ventricle. However, with preservation of these sub-valvular structures, the outcomes equalize, or may be better in severe cases with replacement and sub-valvular structure preservation. (See Ann Thorac Surg 2 81: 1153-61.)

Even though the prognosis of surgically untreated mitral regurgitation is poor, (see N Engl J Med 2 352:875-83), only 33% of patients with significant regurgitation are referred, due to age, co-morbidities, or physician preference (see European Journal of Cardio-thoracic Surgery 34 (2) 935-36).

In the face of a severe, life threatening pathological process with no treatment offered to a majority of patients due to the magnitude of the risks of currently available therapy, a simpler, less invasive approach to treatment, such as a percutaneous device that can effectively eliminate regurgitation, yet preserve annulo-ventricular in atrio-ventricular connectivity and function, is severely needed.

For this reason, there is widespread development currently underway for placement of valves into the aortic (see Circulation December 2002 p. 3006-3008), and Pulmonary, (see J. Am. Coll. Card., vol. 39, May 15, 2002, p. 1664-1669), positions. There are currently a variety of technologies for aortic replacement, but all generally have an expandable support structure for attached pliable leaflets, delivered either through the apex of the ventricle or retrograde through the aorta from the femoral artery (The Journal of Thoracic and Cardiovascular Surgery; October 2008, p 817-819).

Because of the asymmetry of the annuli, as well as the lack of rigidity, the same principals cannot be applied to the mitral and tricuspid valves, or in the aortic valve in the absence of calcification, as in most cases of aortic insufficiency. In the mitral position, several approaches have been pursued. Additionally, in the case of the mitral valve, radial expansion of a prosthetic replacement could impinge on the aortic valve, with which it shares a portion of its annulus along the anterior mitral leaflet.

Primarily, remodeling or alteration (to support or decrease the size) of the mitral annulus by various means has been a focus of intense interest. Some of the most tested of these are those that rely on the perceived anatomic proximity between the posterior annulus and the coronary sinus (see Webb, et al). Although initially promising, the coronary sinus has been shown in virtually all cases to course on the atrial side of the mitral annular plane, and averages 7 to 11 mm from the annulus, and the distances are variable. Moreover, the distances increase in subjects with mitral regurgitation. (See Choure, et al, J Am. Coll. Card.; Vol. 48, No. 10, 2.) The approach has been largely abandoned.

Another approach is the central apposition of the anterior and posterior leaflets at the midpoint, mimicking the so-called "Alfieri stitch". The benefit comes from creation of central coaptation. Devices to create this reconfiguration have been tested and commercialized, but do not control regurgitation to the degree achieved in replacement.

In general, current heart valve replacement procedures generally require invasive surgery. This, of course, is a long, difficult and complex process and requires that the patient endure significant, invasive surgery. While various alternatives have been proposed to minimize this trauma, there is still a need in the art to further reduce such potential injury.

SUMMARY OF THE INVENTION

Recently a number of prosthetic valve-replacement devices have been developed that can be delivered through a trans-catheter approach, and that expand into the natural annulus of a native valve. Since the mechanism of fixation of these valves is generally radial expansion, either actively or passively, a rigid annulus, (such as with calcification or a previously placed surgical valve or ring), is required, or the replacement valve would distort, or even rupture the heart. In many cases of valve pathology, the disease process does not include a rigid annulus or fibrous skeleton of the heart. Consequently, the benefit of these advances is limited to specific pathological states.

Proof of the concept has been published in the medical literature in a very similar way. Inelastic rings were surgically implanted adjacent to the native mitral valve of sheep. One week later, percutaneous valves were successfully expanded into the rings in all five animals. (See Journal of the American College of Cardiology, Vol. 58, No. 24, 2011.) The current invention enables the implantation of the ring, or neo-annulus, through a catheter.

U.S. Patent Application Publication No. 2010/0262232 and International Patent Application No. PCT/US2010/001077 describe an implantable scaffold that contains a neo-annulus into which a prosthetic or bio-prosthetic valve could be implanted. The present invention seeks to provide a means through which that scaffold, which is rigid, can be inserted such that the radially expanding, trans-catheter valve concept can be extended to valves with pathology not currently amenable to this approach.

In a surgical method for improving cardiac function in accordance with the present invention, an implantable scaffold or valve support device is inserted inside a patient's heart (or blood vessel) and attached in a region adjacent to a natural or native valve. In the heart, the scaffold or valve support may be anchored to the heart wall and/or to the native valve itself. The scaffold or valve support device defines an orifice which receives a prosthetic or bio-prosthetic valve after disposition of the scaffold or support device in the heart and either before or after anchoring of the scaffold or support to the heart.

A catheter is placed into the appropriate location, and the scaffold assembly is delivered out the tip of the catheter. The scaffold is positioned in part by steering the delivery catheter and in part by manipulating tethers or wires that are removably attached to the scaffold. The wires may be flexible, steerable, or relatively stiff, and may be pre-formed or made of a component with a memory. In one embodiment of the invention, through use of specific fixation methods and devices disclosed herein, the scaffold is then fixed at its margin or body to a heart or blood vessel wall adjacent to a native valve. In sequence, the scaffold is delivered, positioned, and then fixed to the heart or blood vessel wall. With the scaffold or heart valve support system in place, a prosthetic valve can be installed in an annulus or aperture of the scaffold. In an alternative approach described herein, after the scaffold is ejected from the distal end of the delivery catheter into a heart chamber and expanded from a collapsed insertion configuration to an expanded deployment configuration, a prosthetic valve is seated in an orifice of the scaffold and the combined assembly is attached, through use of specific fixation methods and devices disclosed herein, to the leaflets or the subvalvular apparatus of the native valve.

In the case of AV valves, the scaffold or valve support device is at least indirectly secured to chordae tendineae, and therefore, the papillary muscles of the heart. Such a device can distribute forces to the prosthetic valve similar to those typical of the normal, native valve. Thus, the attached or entrained chordae tendineae serve to retain the scaffold and prosthetic valve in position in opposition to systolic blood pressure. The current invention involves in part a method and an associated device for capturing the natural valve and concomitantly and indirectly the subvalvular apparatus and incorporating those structures into the scaffold or heart valve support system, or to the prosthetic valve.

Where the native valve is captured and coupled to a combined scaffold/replacement valve assembly, the scaffold and the replacement valve mounted thereto are attached to the leaflets of a native valve so that the scaffold and the replacement valve are in fluid-sealing engagement with the leaflets. Closure devices may be provided to close commissure gaps, if necessary.

During the implantation procedure, the valve-supporting scaffold may be attached to the heart chamber or vessel wall via at least one but more preferably a plurality of flexible or rigid tensile suspension element(s) or alternatively the scaffold may be held in place by tethers or other supporting elements extending from a delivery or deployment catheter. In either instance, the scaffold or neo-annulus, or the assembly of the combined replacement valve and scaffold or neo-annulus, are attached to the native valve, such that all forces normally borne by the native valve, and to which the replacement valve is now subjected, are transmitted to the native valve, and its subvalvular apparatus, in the case of atrio-ventricular valves.

A scaffold or neo-annulus in accordance with the present invention, if employed in a setting wherein attachment of the valve directly into the annulus of a native heart valve is not ideal, possible, or otherwise feasible, enables valve placement wherein it otherwise could not occur, yet maintains the normal transmission of forces from the replacement valve to the native valve. The present invention provides devices and mechanisms for fixation of the suspension elements to the heart or vessel wall, as well as devices and mechanisms for incorporation of the sub-valvular apparatus, in the case of atrio-ventricular valves, (or to the native valve in the case of ventricular outflow valves), to the implanted scaffold or neo-annulus.

Fixation of Neo-annulus Suspension Elements to Heart or Blood Vessel Wall

Deployment of a replacement valve through a trans-catheter approach requires first that there is a stable, inelastic valve support scaffold with an orifice into which the replacement valve can be inserted. Stability can be achieved through fixation of such a valve support scaffold to the heart or blood vessel wall. In this embodiment, the process requires first that the scaffold or valve support device be suspended or supported. This scaffold-like element defines, in one embodiment, of an orifice into which the valve will ultimately be deployed, which is suspended by one or a plurality of structural elements of the device, which fixes it to a heart or blood vessel wall.

Therefore, the neo-annulus scaffold may be actively suspended from the heart or blood vessel wall through the use of one or more suspension elements, each an elongate flexible tensile element. The suspension element(s) may be actively or automatically affixed to the heart or blood vessel wall. In the case of active attachment, the suspension element(s) may each be provided with a deployment tether that extends through the deployment catheter to a site of proposed fixation on the suspension element to the heart or blood vessel wall (for example, the end of suspension component remote from its attachment the neo-annulus). With the neo-annulus supported in its desired location, the end of the suspension element is advanced to the proposed site of fixation on the heart or blood vessel wall, and a helical or alternatively-shaped, screw-type fixation or similar component or a pronged staple or other fixation element is used to secure the suspension element to the heart or blood vessel wall.

Once the appropriate locus for fixation of the suspension component(s) on the heart or blood vessel wall has been reached, the tethers used to deliver fixation device(s) to the suspension element(s) may be used both to create fixation and to manipulate/position the suspension element(s). By advancement of the fixation device(s) over the tether(s), a means is provided whereby manipulation of fixation elements and placement of the elements in a specific location in the heart or blood vessel wall. Fixation of the suspension element(s), once achieved, provides support for the neo-annulus, because of its connection to the heart or blood vessel wall by (an) intervening member(s), which is (are) the suspension element(s).

The attachment, or fixation, of a suspension element to the heart or blood vessel wall may be made by a separate component, such as a staple, clip or device of other appropriate design delivered by a separate component, or may be an integral part of the suspension element itself, such as a burr, barb, hook, or other appropriate fixation element. In general, the suspension elements are likely to be sigmoid or somewhat linear structures, extending radially from the orifice-defining neo-annulus scaffold to the point of attachment to the heart or blood vessel wall.

The suspension element or elements are generally part of the construction of, or attached to, the scaffold or neo-annulus as a whole, and are attached or otherwise fixed to the scaffold, extending to the heart or blood vessel wall, wherein the suspension element(s) are attached. However, the suspension elements may be separate structures and be delivered and attached to the neo-annulus in-situ. The suspension elements may be of any length, so that the neo-annulus may be somewhat distant, very near, of even essentially in contact with the wall adjacent to the valve or annulus.

In one embodiment, the orifice-defining neo-annulus scaffold preferably takes the form of a ring. The ring made be made of nitinol or other shape-memory material with a temperature induced memory or other means by which the scaffold assumes a substantially rigid, or at least inelastic configuration of pre-determined shape after ejection from the delivery or deployment catheter. Alternatively, it may be passively expanded and be made of another appropriate material, such as a weave, fabric, or monofilament material.

The scaffold is optionally provided with the above-described linear suspension components, which are extendible outwardly to attach to the heart or blood vessel wall near the native valve for which replacement is intended. The suspension elements may be of any length or shape, and may appear like spider legs, or as ring-topped, flattened tripod (in instance wherein three such elements are used). They are constructed preferably of a spring-like material and are curved to allow for fixation to a heart or blood vessel wall of variable contour, as well as for excursion of the neo-annulus toward or away from the valve as necessary, but may be in any appropriate configuration.

The suspension components or "legs" are, in an especially preferred embodiment, permanently attached/constructed to the valve-support ring, but are of a material and design that allows them to assume a folded or collapsed configuration within the delivery catheter. The suspension elements may be actively extended by deployment tethers operated from outside the subject or automatically extended, in the case of a spring-like material, when released. Also, the suspension elements may either be actively guided toward, or designed in a way as to extend automatically to, the heart or blood vessel wall, wherein fixation of the ends of the suspension elements to the heart or blood vessel wall will ensue. Alternatively they may be actively deployed, as by balloon expansion or other method.

In the passive-fixation iteration of the device, each of the one or more suspension elements has a barb, hook or other appropriate fixation element at its free end. Apposition of the hook, barb, or other appropriate fixation element to the heart or blood vessel wall results in attachment of the respective suspension element to the heart or blood vessel wall. This automatic attachment may be by an expansion or piercing or other passive fixation element. The suspension elements are each configured to passively connected to the heart or blood vessel wall. In the most preferred iteration, the hook, barb, burr, or other appropriate component is manipulated by a tether or other similar component of the suspension capable of the manipulation/engagement, but amenable to subsequent removal. This could occur through release of a self-expansile suspension element that engages and attaches to the heart or blood vessel wall as it expands, as in the case of an expanding metal or other memory-like material that expands when released and pierces the heart or blood vessel wall.

With the neo-annulus located adjacent to the native valve, allowing free flow through its center, and fixation to the heart or blood vessel wall adjacent to the native heart valve, the valve replacement process requires deployment of the valve, and simultaneous or subsequent capture of the native valve and fixation to the neo-annulus/replacement valve complex. In both iterations, the valve-capture tension elements are incorporated into the neo-annulus so as to transmit forces generated by cardiac function to the neo-annulus, and the tethers run over or near the tension elements to allow a "push-pull" on the neo-annulus relative to the native valve.

The orifice, which is more or less central to the device, is generally circular or becomes generally circular, and is defined by an inelastic scaffold or neo-annulus into which a replacement valve can be deployed, the scaffold or neo-annulus being deliverable through a delivery catheter placed at an appropriate position in a heart chamber or blood vessel through a percutaneous, trans-vascular approach.

Therefore, the valve-supporting scaffold is flexible and capable of being collapsed, folded, twisted, or otherwise compressed that it can assume a low profile for delivery but becomes a generally round or otherwise appropriate configuration after delivery. The scaffold or neo-annulus may be reconfigured passively or automatically, for example, by being made of a temperature-sensitive or non-temperature sensitive shape memory material that reconstitutes when liberated from a compressed or folded state. Alternatively, reformation into an appropriately round shape may be active, such as by placement of a central expansile element, such as an inflatable balloon, that actively creates a round orifice or central neo-annulus before deployment of a replacement valve.

In one embodiment, the orifice-defining neo-annulus scaffold preferably takes the form of a ring. The ring made be made of nitinol with a temperature induced memory by which the scaffold, having been delivered in a flexible configuration, assumes a substantially rigid configuration of pre-determined shape after ejection from the delivery or deployment catheter. The scaffold is optionally provided with the above-described linear suspension components, which are extendible radially, or generally in an outward direction, to attach to the heart or blood vessel wall near the native valve for which replacement is intended. The suspension elements appear like spider legs, or as ring-topped, flattened tripod (in instance wherein three such elements are used), or other appropriate configuration. They are constructed preferably of a spring-like material and are curved to allow for fixation to a heart or blood vessel wall of variable contour, and allow for excursion of the neo-annulus toward or away from the valve as necessary.

Since most replacement valves are deployed by radial expansion, the orifice or neo-annulus is preferably flexible for at least a given time after ejection from the delivery catheter, so as to allow manipulation and reconfiguration after delivery, but also relatively inelastic so that a radially expanded valve does not distort it. The valve-supporting scaffold or neo-annulus may therefore be constructed of a braided or monofilament metal or other appropriate synthetic or naturally occurring material with the appropriate physical characteristics.

The scaffold or heart valve support device is thus delivered through a catheter in a collapsed configuration, and so is compressible or otherwise reconfigurable to fit into the lumen of a delivery catheter. After delivery through the tip of a delivery catheter, the scaffold device is be suspended and fixed in a position adjacent to a heart valve for which replacement is considered, and into which a valve can subsequently be placed.

Suspension element(s), as well as the neo-annulus, may be covered or coated with a substance to enhance tissue ingrowth, prevent dot or blood adhesion, may be drug eluting, have heparin or other substance bonding, or otherwise be constructed of a material that enhances tissue ingrowth, prevent clot or blood adhesion, or other properties deemed to be advantageous.

After suspension by the elements, attachment to the native valve leaflets and replacement valve deployment follow essentially as disclosed hereafter.

Stabilization of Neo-ANNULUS Through Temporary Support Through Delivery Catheter Prior to Capture of Native Vale/Subvalvular Apparatus, without Fixation to Heart or Blood Vessel Wall Deployment of a replacement valve through a transcatheter approach requires first that there is a stable, rigid or inelastic neo-annulus, or orifice, into which the replacement valve can be inserted. Stability can be achieved through temporary support of the neo-annulus or orifice without permanent fixation to the heart or blood vessel wall.

In this approach, the valve-receiving scaffold is suspended through or by the delivery system while the valve is deployed and the native valve leaflets are incorporated into the neo-annulus or replacement valve. Thereafter, since fixation of the neo-annulus and replacement valve deployed therein to the native heart valve or subvalvular apparatus is completely supportive of the implanted devices, the connection to and support from the delivery system may be interrupted and the replacement-valve/neo-annulus left in situ, with forces on the replacement valve being transferred to the native valve (and the subvalvular apparatus, in the case of A/V valves), wherein they are borne in the normal or natural physiological state.

In this embodiment, the neo-annulus may be suspended by a single tether or a plurality of tethers (preferably three or four) that allow both support and positional maneuvering of the neo-annulus. The tethers are removable when the need for support no longer exists. Thus the neo-annulus is deployed via the delivery system connected to the tethers, and after either actively or passively expanding, is positioned and supported over the orifice of the targeted native valve. Most preferably, the tethers are placed over or near tensile coupling elements having free or distal ends adapted to entrain, capture, and grasp native valve leaflets. The tethers are slidable relative to the tension/tensile coupling elements and engage the neo-annulus or scaffold so as to enable the operator to push the scaffold in a distal direction while holding or pulling on the tensile coupling elements, thereby approximating the scaffold (typically with replacement valve mounted thereto) and the leaflets of the native valve.

Regardless of the support/suspension strategy (suspension elements or temporary support through the delivery system), the suspended neo-annulus is supported at least in part by the positioning tethers that pass over the tensile coupling elements. The tensile coupling elements pass through or otherwise are incorporated into the substance of the neo-annulus. On the distal ends of the tension elements are devices for capturing and entraining the native valve leaflets, to retract the native valve leaflets and bring them into contact or near contact with the neo-annulus.

The devices for valve leaflet capture are hooks (e.g., grappling hooks), barbs, clips, burrs, or other appropriate entrainment components that allow adherence/fixation of the tension elements to the valve leaflets while still allowing their normal or near normal excursion. Thus, until engaged, valve leaflets have continued "normal" (or with no or minimal additional impediment), or near normal function until such time as they are captured and tethered/incorporated into the neo-annulus/replacement valve complex by simultaneous "forward" or distally (in the direction of forward blood flow) directed force on the tethers and retracting force on the tension elements within or near the tethers.

The hooks, barbs, clips, burrs, or other appropriate components may penetrate, impinge, entrap, clip over, or in any other appropriate way engage the leaflet so as to allow tension to be placed permanently thereon by traction elements to which the hooks, barbs, burrs, or other appropriate components are attached. Since the tension elements are incorporated into an aspect of the neo-annulus or central orifice, the valve leaflets may be pulled into contact with the neo-annulus or central orifice.

To create the excursion of the neo-annulus with its orifice toward the native valve leaflets in a preferred embodiment, the tension members are retracted or pulled in a proximal direction from the proximal end (i.e., outside of the body) as the tethers, generally tubular members surrounding portions of the tension members, are advanced in a distal direction from the proximal end of the delivery catheter. The opposing forces cause the valve-supporting neo-annulus or scaffold with its valve-receiving orifice to move toward the native valve. In general, since this excursion may also disrupt native valvular function, it is contemplated that the replacement valve will have been deployed into the central orifice of the neo-annulus or scaffold before the final approximation excursion is generated.

It is possible for the neo-annulus to be delivered through a catheter passed directly through the heart wall. In the case of the A/V valves, entry may be made through a ventricle and the neo-annulus suspended proximal to the valve on the atrial side. In that approach, the support of the valve or sub-valvular structures is achieved from the ventricular side, reversing the above-discussed neo-annulus seating and supporting procedure. In order to approximate a valve support member or scaffold and the leaflets of a native valve to one another in a trans-ventricle procedure, the scaffold or valve support member may be pulled in the proximal direction (towards to operating surgeon) while the valve leaflets are held or pushed in the distal direction. In any event, forces are exerted on the scaffold and the valve leaflets so as to move the scaffold or valve support member on the one hand and the valve leaflets on the other hand towards one another and into force-transmitting and effective fluid-sealing contact.

To permanently position the replacement-valve/scaffold complex in a fluid-sealing engagement with the valve leaflets, the tension or tensile coupling elements preferably have a "lock" such as a one-way incremental movement device in the nature of a ratchet. The ratchet may take the form of cooperating tooth formations and a tapered passageway or spring loaded latch, a cam, a compression device or other appropriate component that prevents the valve-supporting neo-annulus or scaffold member from moving away from the native valve, once having moved toward it. The lock may be built into the neo-annulus or scaffold, or be a separate component, advanced over the tension element toward the neo-annulus or central orifice.

Once the neo-annulus/replacement valve complex has become fixed to the native valve, creating a seal, the neo-annulus is supported by the native valve leaflets. The neo-annulus or scaffold may be additionally supported by tensile suspension elements attached to the cardio-vascular wall, particularly in the event that such suspension elements are used to hold the neo-annulus or scaffold in place during the implantation procedure.

After the securing of the neo-annulus or scaffold to the native valve leaflets, positioning tethers can be removed, as well as proximal portions of the tensile coupling elements. The distal end portions of the tensile coupling elements remain in place holding the neo-annulus to the native valve leaflets in tension, the final position of the neo-annulus or scaffold being secured through the "lock" mechanism.

It is possible that after restriction/capture of the valve leaflets, the neo-annulus/captured valve contact will not completely eliminate leakage around the valve. In one embodiment of an implantation system in accordance with the invention, an inflatable or otherwise expandable component such as an annular bladder can be enlarged around the neo-annulus to further inhibit paravalvular leak and enhance the seal between the native valve and the scaffold/replacement valve. This sealing component may initially take the form of a collapsed inner-tube-like component that is attached to the neo-annulus or that is separately delivered and positioned in situ. The inflatable sealing component is provided with an inflation tube through which air, saline solution, another fluid, or other appropriate substance, such as polymers, is infused, expanding the sealing component to eliminate potential or actual peri-valvular leak. After expansion of the sealing component, the inflation tube is removed/plugged, or otherwise eliminated from permanent connection with the inflatable sealing component. Also, a fluid, such as saline, may be initially infused, but later be exchanged for another, potentially permanent material, such as a polymer or other material of appropriate properties.

In addition to acting as a means of resolving perivalvular leakage, the circumferential or partially circumferential inflatable component may be used simply as a means to make the apposition of native valve and neo-annulus less erosive, less distorting to the heart, more likely to fit a rigid neo-annulus/replacement valve complex into a generally soft, beating heart without long-term tissue change, or other potentially desirable characteristics. In essence, the inflatable component may impart the characteristics of a "sewing ring" such as is found on most valves constructed for open surgical implantation.

The inflatable sealing component may be delivered as a separate element, or be a part of the construct of the central orifice or neo-annulus. It may be constructed of an elastic material or one of fixed volume and/or shape, regardless of the pressure of its internal contents. It may be filed with fluid long-term, or have a permanent polymer that can be infused primarily, or as a replacement for an initial fluid or gas infusate. It may be covered or coated with a substance to enhance tissue ingrowth, prevent clot or blood adhesion, may be drug eluting, heparin or other substance bonding, or otherwise be constructed of a material that enhances tissue ingrowth, prevent clot or blood adhesion Alternatively, an implantable clip, barb, staple or other approximation device of appropriate design may be placed at the site of a gap between native valve leaflets for bringing the leaflets into apposition around the scaffold or valve support device to obliterate a site of perivalvular leakage. One such device for perforating two nearby tissue strictures has a multi-pronged or multiply legged "V", "U", "Y" structure or other similarly shaped component, such that after perforation of the generally two, or paired, barbs on the clip into the tissue structures, advancing the clip in one direction (in the examples described, upward) the perforation sites are brought into apposition.

Such a clip-like approximation device is constructed of a metallic or other appropriate material, may have memory, and are placed and manipulated through the delivery system or other means. It is affixed in place, as with bending the arms outward, automatically springing when released, fixation with a separate element, or other appropriate means. Alternatively, a spring-like device, suture-like device, staple-like device, or other means of apposing native valve leaflets at gaps may be used.

The leaflet approximation device may be introduced prior to introduction of the remainder of the implantable devices, creating a smaller orifice in the native valve, and enabling a potentially more complete circumferentially solid line of contact between the neo-annulus/replacement valve complex. Therefore the capture of the native valve, introduction of the scaffold, deployment of the replacement valve may follow apposition of the commissures, in order to diminish the size of the native vale orifice.

In general, in the implantation embodiment wherein the neo-annulus is only temporarily supported by the delivery system while permanent fixation to the native valve is achieved (or if suspended by either elongate elements, as disclosed above, or by a membranous component disclosed previously, and after suspension has been accomplished), the placement of the scaffold and replacement valve may consist of a procedure summarized as follows:

- A delivery system is inserted through the vascular system or heart wall to an appropriate site in a heart chamber or blood vessel near a valve to be replaced.
- A device consisting of the tensile coupling elements for valve capture, the neo-annulus, suspension elements, if appropriate, support tethers, and other components, as required, is advanced out of the delivery system.
- The valve leaflets are engaged by the tensile coupling elements incorporated into or attached to the neo-annulus. In some iterations, where a heart wall is used for introduction, these tensile elements may be compressive.
- The neo-annulus is suspended to the heart or blood vessel wall if appropriate, or alternatively, supported only by tethers emanating from the delivery system.
- The replacement valve is deployed into the neo-annulus.
- The native valve is retracted by the tensile coupling elements with entrainment or capture components on their ends, such that the retracted leaflets form a "gasket"-like element toward or around the perimeter of the replacement valve/neo-annulus complex, eliminating leak and retracting the native valve out of the inflow or outflow tract to or from the native valve. Separate or incorporated locking devices integrated with the tension elements cause a "one-way" tightening of the tension elements, so that the leaflets are retracted into the neo-annulus/replacement valve complex.
- The inflatable element, if used, is inflated to eliminate peri-valvular leakage. The initial inflation substance can then be replaced if appropriate, and imaging confirms elimination of peri-valvular leak. Alternatively, a hook, barb, clip, or other device of appropriate design is placed into adjacent native valve leaflets at the site of a gap, such that valve leaflets are apposed.
- Tethers, tubes, extensions of tension elements are finally removed, leaving only the replacement valve, neo-annulus, and inflatable component or gap-closure device, if used. Any other appendages associated with delivery, deployment, stabilization, fixation, valve capture, inflation, etc. are removed.
- As an alternative, the commissures may be apposed prior to the implementation of the above sequence.

Capture of the Native Valve

With certain valves in the heart, specifically the atrio-ventricular valves, the sub-valvular structures are important for chamber function. It has been recommended, therefore, when replacement is performed rather than repair, that these structures be incorporated into the annulus of the new valve. (See M. A. Borger, et al Ann Thoracic Surg 2006; 81:1153-1161.) The current invention provides a device and method for incorporation of these structures into the scaffolding, thereby preserving ventriculo-annular contribution to systolic function.

Accordingly, the current invention also contemplates a device and means for attachment of the native valve, or sub-valvular structures (in the case of the mitral or tricuspid valves) to either the neo-annulus or another part of the implanted scaffold. In the principal embodiment, attachment elements consist of single or multiple hooks, single or multiple barbs, or other appropriate means of grasping the valve leaflet(s) or chordae tendineae, and attaching them either directly or with an intervening element to some portion of the scaffold, such that, in the case of the atrio-ventricular (A/V) valves, systolic ventricular forces on a valve implanted into the neo-annulus will be transmitted to the papillary muscles and cords rather than to the fixation points of the scaffold margin alone, thus preserving systolic A/V valvular/papillary function.

In a particularly preferred embodiment, the valve leaflets are "snagged" by one or more hooks or barbs. As discussed above, a device with multiple hooks is incorporated, through tensile or compressive coupling members, into the neo-annulus, and is delivered through the native valve orifice during the entrainment process by bringing the neo-annulus toward the leaflets or subvalvular structures. The hooked device may be advanced through a catheter and across the native valve orifice prior to emergence through the delivery system of the neo-annulus and suspension elements, if used, or advanced from the ventricle, in the case where a transmural (across a heart wall) approach is used. In other words, the valve capture elements may be first out of the delivery system, followed by the neo-annulus, followed by the suspension elements, if used, or the last, depending on the direction of deployment and delivery. In this way, minimal delivery system size may be possible. Other sequences of delivery are possible.

The hooks, barbs, clips, or other appropriate components attached to the tensile coupling elements may precede the delivery of the remainder of the scaffold out of the delivery catheter. The hooks, barbs, clips, or other appropriate components may have one or more separate delivery components, which enable the capture of the leaflets. The hooks, barbs, clips, or other appropriate components are removably or temporarily attached to the delivery or deployment device, which may advance the hooks or barbs out of the catheter and into the valve orifice as noted above. In a preferred approach, the hooks may "snap" into a delivery element, or may be freely advanced through a native valve, and are passed from a delivery catheter through the valve orifice, between leaflets. The delivery element may have the capability of manipulating the location on the native valve wherein the hooks, barbs, clips, or other appropriate components are engaged to the native valve.

Alternatively, the delivery catheter may cross the native valve, deliver the hooks, barbs, burrs, or other valve capture elements, then retract back across the native valve before releasing the neo-annulus and other components.

The deployment elements may then orient the hooks or barbs, and subsequently release them once the leaflets were engaged by the hooks or barbs. The tensile coupling elements on the hooks may be used to further manipulate the hooks or barbs, such as twisting or applying tension to increase or maintain purchase of the hook or barb on the leaflet.

In a preferred embodiment, tension or tensile members attached to the hooks or barbs used to capture the valve leaflets may be permanently attached to or through a retention element of the scaffold or neo-annulus, generally at outer edge, so as to facilitate the apposition of the native valve around the edge of the neo-annulus/replacement valve complex. Alternatively, the elements may be secondarily attached to the neo-annulus or scaffold.

Because the coaptation surface of some valves is linear, while the replacement or prosthetic valve to be placed is round, it may be desirable to have the hooks or barbs dispersed or spread around the perimeter of the neo-annulus/replacement valve complex. In the most preferred embodiment, the tension/tensile members are preferably distributed at intervals around the neo-annulus. Alternatively, they may be spread separately after exiting from their connection to the central orifice on neo-annulus.

Therefore, there may be a feature of the deployment element that fans out or separates the hooks or barbs as they leave the delivery catheter. Such a device element may consist of a released spring, elastic material, pre-shaped memory substances, active opening, or other appropriate means of dispersing or separating the hooks or barbs over a length of valve leaflet before attachment of the valve-grasping element to the scaffold or valve support system.

In order to assist in the delivery of the valve-capture elements, which are hooks, barbs, or other appropriate elements designed to engage the native valve leaflets, the hooks, barbs, or other appropriate elements may be collapsed or otherwise constrained into a lower profile configuration. This enhances delivery and minimizes native-valve functional disruption prior to fixation to the native valve, replacement valve deployment, and native valve capture. As such, the hooks, clips, barbs, or other appropriate elements may be actively configured into a low profile, as when bound by a fabric or other constraint element, which is removed or otherwise released prior to engagement with the valve leaflets. Alternatively, the hooks, barbs, or other appropriate elements may be formed of a self-expanding material, such that the intended profile/configuration may be taken on after delivery.

Tethers, tension elements, infusion ports, or other appendages, if fixed to the implantable devices, may be severed or otherwise separated from the implantable devices through the use of an end-cutting device, which can be individually passed over or near the appendage. Alternatively, an attenuated area may be constructed into the appendage such that a natural breakage site can create a severance by twisting, pulling or otherwise manipulating the appendage. Other means of separating tethers, tension elements, infusion ports, or other appendages, if fixed to the implantable devices, as appropriate, may be employed, either through the characteristics of the ancillary elements or appendages, or through introduction of a separate component to create the separation, as appropriate.

The present invention allows attachment of the central orifice or neo-annulus to the heart or blood vessel wall by a continuous suspension element (previously disclosed, see U.S. Patent Application Publication No. 2010/0262232 and International Patent Application No. PCT/US2010/001077), by discontinuous suspension components, with or without a specific margin. Alternatively, the central orifice or neo-annulus may be supported only by the delivery system until fixation of the orifice ore neo-annulus to the native valve can be achieved.

In the current disclosure, the scaffold can be secured to the heart or vessel wall, such that a valve may be delivered through a limited intrusion by utilizing a catheter to deliver and assemble the heart valve components in-situ. This disclosure describes a scaffold which may be attached to the heart or blood vessel wall in a limited way, or else simply stabilized while the valve is inserted, deployed, and subsequently affixed to the native valve, rendering the initial attachment of the scaffold, or neo-annulus of lesser or only temporary importance to the ultimate fixation of the replacement valve.

Because the replacement valve must be deployed into approximately the same location as the native valve, it is necessary to alter the position of the native valve. In the current invention, a mechanism for pulling the native valve leaflets toward the periphery of the neo-annulus and away from the valve center is also provided Because this fixation of the generally round scaffold, or neo-annulus to the native valve would require that the two be more-or-less sealed circumferentially, it is possible that native valve leaflets may require plication or otherwise reconfiguration, such that peri-valvular leakage does not occur. A device and method for achieving this reconfiguration is disclosed herein.

Attachment of Scaffold to Heart Wall Via Fasteners Slid Along Respective Tethers The present invention provides devices and mechanisms for fixation of a margin of a scaffold or valve support device to the heart or vessel wall, as well as devices and mechanisms for incorporation of the sub-valvular apparatus, in the case of atrio-ventricular valves, to the implanted scaffold or neo-annulus.

In the principal embodiment of the present invention, the scaffold has a series of tethers or support elements attached to its outer edge or margin at intervals around its circumference. In this iteration, there are preferably primary and secondary tethers. The margin of the scaffold or valve support is attached to the heart or vessel wall at the points on the margin where the primary tethers are attached. Because three points determine a plane, in most cases there are three primary tethers (but could be more or fewer). Secondary tethers may be used to position additional fixation points of the scaffold margin after the scaffold margin is attached to the implantation site at the primary points. In some cases it may not be necessary for the secondary tethers to have the ability to manipulate the margin of the scaffold.

The scaffold, which is generally delivered through the lumen of a catheter, is advanced out the tip of said delivery catheter and manipulated in into the desired position through the process of advancing or retracting the primary tethers. The delivery catheter is advanced through the blood vessels or cardiac chamber of the patient and positioned in the appropriate site for scaffold delivery and subsequent fixation. In general, the scaffold is crimped or otherwise packed in the catheter lumen, then pushed or otherwise extruded from said catheter. The scaffold may expand automatically from the collapsed insertion configuration to the opened implantation configuration.

In a preferred embodiment, the tip of the delivery catheter is steerable in at least one direction, such that the position of the scaffold can be directed to the proper location, not unlike a movie projector aims a film image at a screen. The steering element may be a property of the delivery catheter on by placing a movable element into the catheter lumen after the scaffold has been advanced. The scaffold can be moved toward the appropriate location by advancing or otherwise manipulating the tethers. The orientation of the scaffold is controlled by differentially advancing the tethers, particularly the primary tethers. Steerability may not be needed in instances where a heart wall is the site of introduction of the delivery system.

Once the appropriate locus of the scaffold margin has been reached, the tethers serve not only as holders to maintain position of the scaffold position, but also as support for passage and placement of margin fixation devices. In this embodiment, the sites and number of fixation points are determinable by the number and spacing of the primary and secondary tethers around the scaffold margin.

Once fixation is deemed to be satisfactory, and fasteners have been advanced or otherwise placed, the tethers are detached from the scaffold margin, leaving the scaffold, attached at intervals around its circumference, to the heart or blood vessel wan. By advancement of the fixation devices over the tethers, a means is provided whereby manipulation of fixation elements and placement of those elements at specific points around the circumference of the scaffold from a remote location and through a catheter is possible. Fixation of the outer scaffold margin to the heart, once achieved, provides support for the neo-annulus, because of its connection to the margin by an intervening member such as a membrane.

In a principal iteration, fixation elements slide over the primary and secondary tethers, advanced by sheaths slidably positioned around and over the tethers. The fixation elements, in one form, consist of individual screw-like devices, each of which is located on a respective one of the tethers. The devices in this case each comprise a double helix attached to a cap that may take the form or a circular disk. The cap has a hole and is passed over the tether (the tether traversing the hole), such that the screw-like fixation device can be advanced over the respective tether to the margin of the scaffold and into the heart or vessel wall.

The double helix can be either twisted or simply pressed into the wall. Typically, pushing the associated sheath in the distal direction over the respective tether and against the cap of the screw-like fastener or fixation device first causes the distal tips of the helix wires to insert into the tissue and then induces turning of the helix about its longitudinal axis. The helices may have one or more barbs or other elements to inhibit their unintended dislocation. Such a barb or other element may be activated after acceptable deployment has been achieved. Once the fixation element is embedded in the heart or blood vessel wall, the tether can be detached (for instance, by a twisting action or a simple withdrawal), leaving the fixation element holding the scaffold margin to the wall. In this instance, the cap can straddle the margin with one or both of the helical elements perforating the membranous element.

Alternatively, the fixation elements or fasteners may take the form of a double, pronged or pincer-like staple or other appropriate design, pre-formed or super-elastic element that, when applied to the margin over the tether, fixates the margin to the heart or vessel wall. There may be an element of the device in this instance to hold the margin element with or without perforating the membranous element of the scaffold.

In any fastener or staple design, there may an element in the cap of the fastener or staple that prohibits the dislodgement of that fastener. For example, the cap of a helical fixation element may have a pin, which when advanced, enters the heart or blood vessel wall and prohibits unintentional untwisting and removal. Similarly, staples or pronged fasteners may have a spring-loaded barb or hook, which advances into the heart or blood vessel wall with no resistance but prohibits withdrawal of the staple.

The tethers may be disconnected from the scaffold after fixation either by unscrewing, twisting to fracture, or other means of separation from the margin of the scaffold. Alternatively, a tool can be introduced into the target heart or blood vessel that is manipulated to induce the separation.

With certain valves in the heart (specifically the atrio-ventricular valves), the sub-valvular structures are important for chamber function. It has been recommended, therefore, when replacement is performed rather than repair, that these structures be incorporated into the annulus of the new valve. (See M. A. Borger, et al Ann Thoracic Surg 2 81:1153-1161.) The present invention provides a device and method for incorporation of these structures into the scaffolding, thereby preserving ventriculo-annular contribution to systolic function.

Accordingly, another feature of the present invention relates to a device and means for attachment of the native valve, or sub-valvular structures (in the case of the mitral or tricuspid valves) to either the neo-annulus or another part of the implanted scaffold. In the principal embodiment, these consist of one or more hooks, clips, barbs, or other appropriate means of grasping the valve leaflet(s) or cordae tendineae and attaching them either directly or with an intervening element to some portion of the scaffold, such that, in the case of the atrio-ventricular (A/V) valves, systolic ventricular forces on a valve implanted into the neo-annulus will be transmitted to the papillary muscles and cords rather than to the fixation points of the scaffold margin alone, thus preserving systolic A/V valvular/papillary function.

In a preferred embodiment, the incorporation of the valve or sub-valvular elements is accomplished after the scaffold or valve-support device has been fixed to the heart or blood vessel wall. A separate tool is then introduced into the chamber or blood vessel whereby the valve leaflets are "snagged" by one or more hooks or barbs. In a most preferred embodiment, a device with multiple hooks is advanced through a catheter and across the valve orifice when it opened, as in forward flow, and retracted when the valve closes, piercing or otherwise capturing the leaflets, such that they (the leaflets) can be pulled into the scaffold as desired. In such an embodiment, the hooks or barbs separate so that the individual leaflets are not tethered to each other when the cycle requires the valve to open, thereby avoiding an obstruction.

The hooks or barbs, which actually capture or entrain the leaflets, may be reversibly or temporarily attached to a delivery or deployment device, which advances the hooks or barbs out of a catheter and through the valve orifice as noted above. In one iteration, the hooks attach or snap into a deployment element, which is passed from a delivery catheter through the valve orifice, between the leaflets. The delivery or deployment device then orients the hooks or barbs, and either actively or passively releases them once the hooks or barbs engage the leaflets. Tethers (tensile elements) may be attached to the hooks or barbs for use in further manipulating the hooks or barbs, such as by twisting or applying tension to increase or maintain purchase of the hooks or barbs into the leaflets or subvalvular structure.

Because the coaptation surface of some valves is linear or planer, while the replacement or prosthetic valve to be placed is round, it may be desirable to have the hooks or barbs dispersed or spread around the perimeter of the replacement valve. Therefore, there may be a feature of the deployment element that "fans out" or separates the hooks or barbs as they leave the delivery catheter. Such a device element could consist of a released spring, elastic material, pre-shaped memory substances, active opening, or other appropriate means of dispersing or separating the hooks or barbs over a length of valve leaflet before attachment of the valve-grasping elements to the scaffold or valve support system.

The present invention contemplates snagging the valve leaflets and rolling them up into the new valve annulus or into the scaffold or valve support system. The natural valve leaflets are generally disabled by being marginalized, around the edge of the new valve or neo-annular element of the scaffold or heart valve support system. This procedure is akin to gathering a curtain at the edge of a window and wrapping it tight to the new frame. In the case of the A/V valves, the cordae tendenae, which are still attached to the papillary muscles or ventricular wall, transmit their forces to the margin of the new valve or the scaffold. The force generated by ventricular systole keeps the prosthetic valve and scaffold from being dislodged into the atrium.

Another issue is that the anterior leaflet of the mitral valve, if malpositioned, can obstruct the LV outflow tract causing subvalvular aortic stenosis. This is called "SAM", or systolic anterior motion, and can be the consequence of mitral repair done imperfectly. With a pure in-valve replacement of the mitral, the anterior leaflet may be displaced into the sub-aortic position, which would potentially create SAM and could be deleterious to cardiac function.

The present invention contemplates a leaflet capture device with hooks, barbs, or other appropriate components that grasp and entrain the valve leaflet edges and curl the leaflets against the replacement valve annulus or scaffold margin, thereby retracting and disabling the leaflets around the margin of the replacement valve or into the scaffold. This procedure has the additional benefit of sealing the edge or margin of the scaffold against leakage. The bunched up leaflets serve as a "gasket" against leakage of blood back into the atrium, thereby making discontinuous attachment to the heart or blood vessel wall of the scaffold margin to the atrial wall feasible from a standpoint of valvular or perivalvular regurgitation.

In the case of the aortic or pulmonary valves, the scaffold or heart valve support system would be fixed either on the ventricular or arterial side of the valve with fixation thereto. In the case of the aortic valve, if placed in the aorta, the scaffold or valve support system is perhaps best placed in a sub-coronary ostial position so as not to obstruct coronary flow. In this application of the invention, the hooks, barbs or other appropriate components for grasping the valves are modified to grasp or entrap the leaflets from the convex side of the leaflet, thereby ensnagging or otherwise achieving leaflet fixation on or through the ventricular surface or coaptation surface/margin of the valve.

BRIEF DESCRIPTION OF THE DRAWINGS

FIG. 38 is a diagram similar to FIG. 37, showing a fastener or locking element crimped to the two strands of the tether.

FIG. 39 is a side view of a grappling hook for capturing the sub-valvular apparatus in a method in accordance with the invention.

FIG. 40 is a front view of the grappling hook of FIG. 39.

FIG. 62 is a schematic perspective view similar to FIG. 61, showing the neo-annulus/replacement valve complex seated the orifice of the native valve after removal of the tethers and severing of the tensile coupling elements.

FIG. 63 is a schematic perspective or side elevational view, showing a step of an alternative valve implantation procedure, wherein a ring-shaped neo-annulus scaffold or valve support member is provided with a plurality of elongate flexible suspension elements that are fixed to the heart or blood vessel wall via respective removably attached deployment tethers that deliver staples or clips.

FIG. 65 is a partial schematic perspective view similar to FIG. 63, showing a detail of an alternative, auto-fixation, method of attachment of a suspension line to a heart or vessel wall.

FIG. 70 is a series of three side elevational views of a tissue approximation clip or anchor in three configurations relative to apposed valve leaflets, initially inserted through a commissure gap, then retracted causing apposition of the leaflets and a filling of the gap, and finally with prongs bent for permanent placement.

FIG. 71 is a partial schematic perspective view similar to FIG. 69, showing the anchor-shaped clip of FIG. 70 deployed for leaflet-edge approximation.

FIGS. 72A and 72B are a pair of partial schematic cross-sectional views of an annulus or ring-shaped valve support member, a tether and a tensile coupling element, FIG. 72A showing a collapsed bladder-like component, along with an inflation-port, FIG. 72B showing the bladder-like component after inflation.

FIG. 73 is a schematic partial side elevational view of a neo-annulus scaffold in apposition with a captured valve leaflet with the inflatable component of FIGS. 72A and 72B in an expanded configuration sealing a line of contact and with infusion tube and port still attached.

FIG. 82 also depicts a portion of a pusher sleeve or tube.

FIG. 84 is a schematic partial cross-sectional view similar to FIG. 83, showing the helical fastener advanced into the heart wall, with the fastener straddling the margin of the scaffold.

FIG. 106 is a schematic perspective view of an expanded valve-support scaffold extended via positioning tethers out of a delivery catheter, showing the catheter in a pair of configurations illustrating steerability of the catheter tip.

FIG. 107 is a schematic perspective or isometric view of a portion of a leaflet entrainment device in accordance with the present invention.

FIG. 108 is a schematic perspective or isometric view of a portion of a modified leaflet entrainment device in accordance with the present invention.

DEFINITIONS

Figure 1:
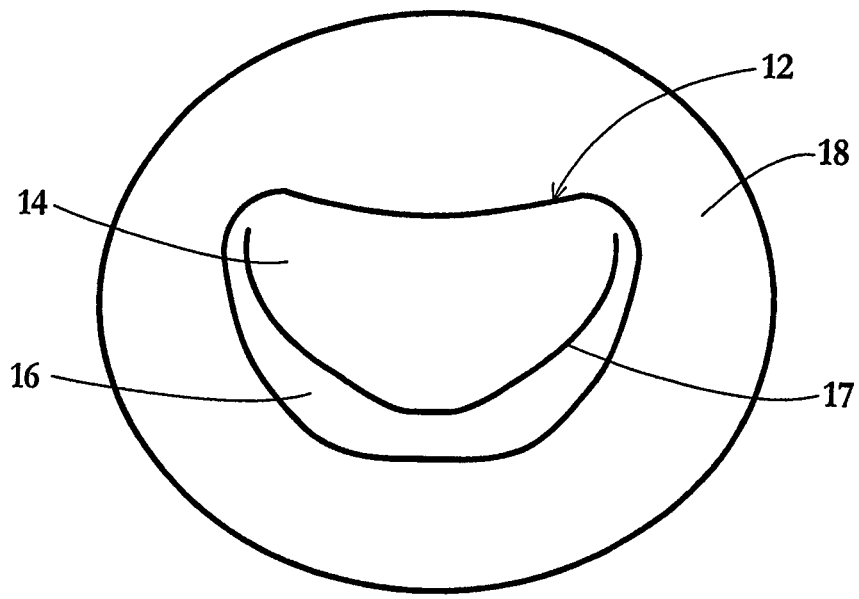
FIG. 1 is a view of the mitral valve from the left atrium.

The word "tether" is used herein to denote an elongate member that extends from outside a patient to an implantable device inside the patient, especially but not necessarily within the vascular system. A tether is used to remotely manipulate and position the implantable device within the patient and may also be used to implement attachment of the implantable device to organic tissues of the patient. It is contemplated that a tether is normally detachable from the implantable device once implantation has been secured. A tether may be a wire made of a metallic or metal alloy material and is capable of transmitting compressive, tensile and torsional forces as required.

The terms "scaffold" and "neo-annulus" are used interchangeably herein to denote an implantable device or structure that serves as a framework for receiving a prosthetic valve and anchoring the valve to the patient at the site of a malfunctioning native valve. A scaffold or neo-annulus is preferably delivered to the operative site via a catheter. Consequently, the scaffold or neo-annulus must be flexible or collapsible for insertion into the patient. Once the scaffold or neo-annulus is ejected from the catheter into the patient, the scaffold or neo-annulus expands to a predetermined use configuration suitable for receiving, seating and attaching to a prosthetic or bio-prosthetic valve. A scaffold or neo-annulus as described herein defines an orifice, preferably circular, for receiving a prosthetic or bio-prosthetic valve.

The term "prosthetic" as applied to a valve herein includes bio-prosthetic valves.

The term "force-transmitting and fluid-sealing contact" as used herein with reference to the implantation of a scaffold or neo-annulus in juxtaposition with or apposition to native valve leaflets means in part that the scaffold or neo-annulus is attached at least indirectly to the native valve leaflets so as to enable the transmission of operative natural valve forces at least in part over the native valve to the scaffold or neo-annulus and the prosthetic valve attached thereto. The term "force-transmitting and fluid-sealing contact" also means that the implanted scaffold or neo-annulus is effectively sealed relative to the natural valve so that blood flow occurs essentially solely through the prosthetic valve upon completion of the implantation procedure. Sealing may occur wholly or in part because of direct contact between the scaffold or neo-annulus and the native valve leaflets or between the scaffold or neo-annulus and the cardio-vascular wall about the native valve. A seal may be effectuated wholly or in part because of the use of an ancillary sealing element or elements such as staples, clips or sutures or one or more inflatable bladders that close off potential fluid flow channels about the scaffold or neo-annulus.

The term "cardio-vascular wall" is used herein to denote the inner surface of a heart chamber or a blood vessel into which a prosthetic valve and its associated scaffold or neo-annulus is implanted.

The terms "tensile coupling element" and "tension member" and variations thereof are used herein to denote an elongate member such as a wire which may be pushed or pulled and thus supports both compressive and tensile forces, as well as torsional forces and which in part remains in a patient connecting a scaffold or neo-annulus to a patient under tension.

The terms "distal" and "distally directed" are used herein to denote a direction extending from an operator such as a surgeon, who is outside a patient, towards the patient and more particularly towards a valvular structure inside a patient. Concomitantly, the terms "proximal" and "proximally directed" denote a direction extending towards an operator such as a surgeon from a patient and more particularly from a valvular structure inside a patient.

DETAILED DESCRIPTION

The present invention provides devices and associated methodology for attaching a valve-supporting scaffold or frame member to a subject, particularly to natural valve leaflets of a native heart or vessel valve of the subject. Such a valve-supporting scaffold and methods related thereto are disclosed in U.S. Patent Application Publication No. 2010/0262232, the disclosure of which is hereby incorporated by reference.

As depicted in FIG. 1, a mitral valve 12 includes a pair of leaflets or valve flaps 14 and 16 that contact one another along a generally D-shaped set of points 17 in a closed state of the valve. On the atrial side of the valve 12, leaflets are continuous with an internal wall 18 of the atrium.

Figure 2:
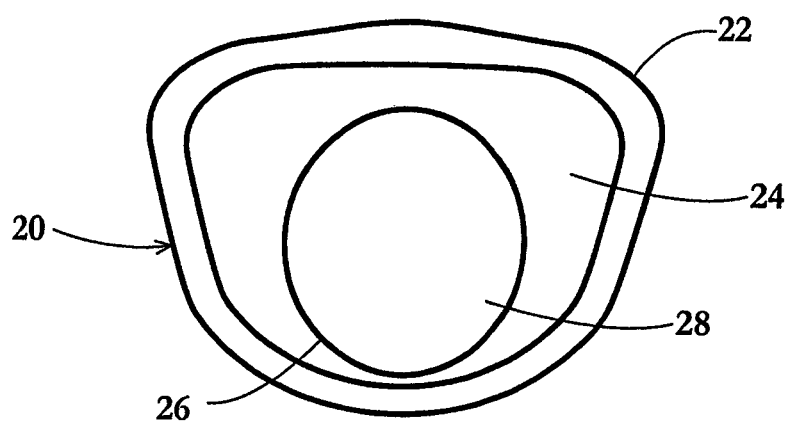
FIG. 2 is a view of a deployed implantable scaffold component in accordance with the invention, showing an outer margin, a membranous portion, an orifice for valve placement, and a neo-annulus.
Figure 9:
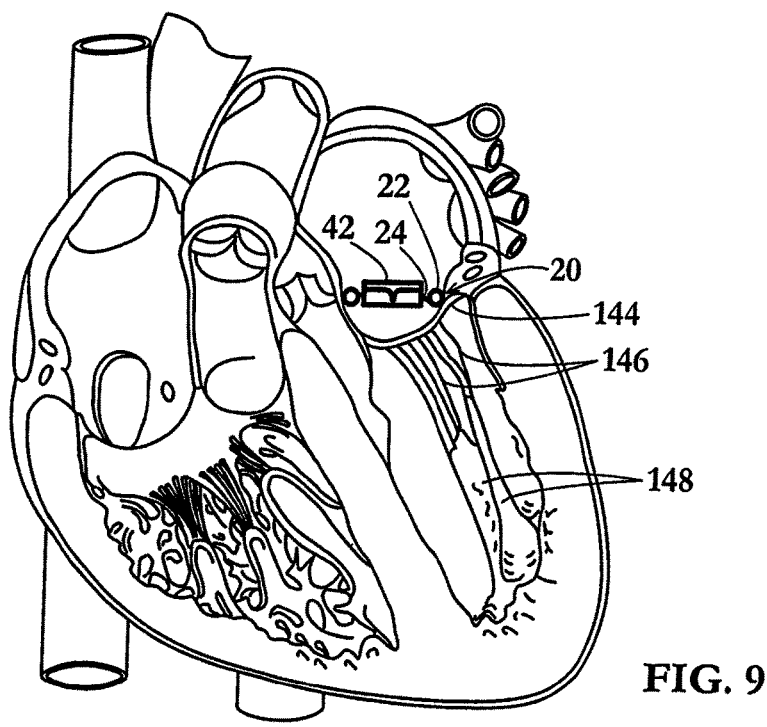
FIG. 9 is a photograph that includes a diagram of an implantable scaffold in accordance with the invention showing diagrammatically how the implantable margin is fixed at the mitral annulus, an abbreviated membranous portion separating the spaces, and a cylindrical implanted valve with apposed leaflets in profile resides within the neo-annulus.

As depicted in FIG. 2, an implantable valve scaffold or mounting component 20 includes an outer margin or rim element 22, a membranous portion 24, and a generally annular inner margin or rim element 26 defining an orifice 28. Orifice 28 serves as a neo-annulus for receiving or seating a prosthetic or bio-prosthetic valve 42 (FIG. 9). It is contemplated that the valve is a modular or staple article. However, the valve may be custom designed.

It is to be understood that the inner margin or rim element 26 generally has a circular or cylindrical shape, so as to enable the seating of commercially available prosthetic or bio-prosthetic valves, which are circular or cylindrical. The term "annular member" is used herein to denote a continuous or endless configuration that defines an opening, orifice, or aperture. While the opening, orifice, or aperture is typically round or circular, the shape is not necessarily such. An "annular member" as that term is used herein particularly with reference to the element that defines the valve-receiving orifice or neo-annulus, may be oval or even polygonal.

Figure 3:
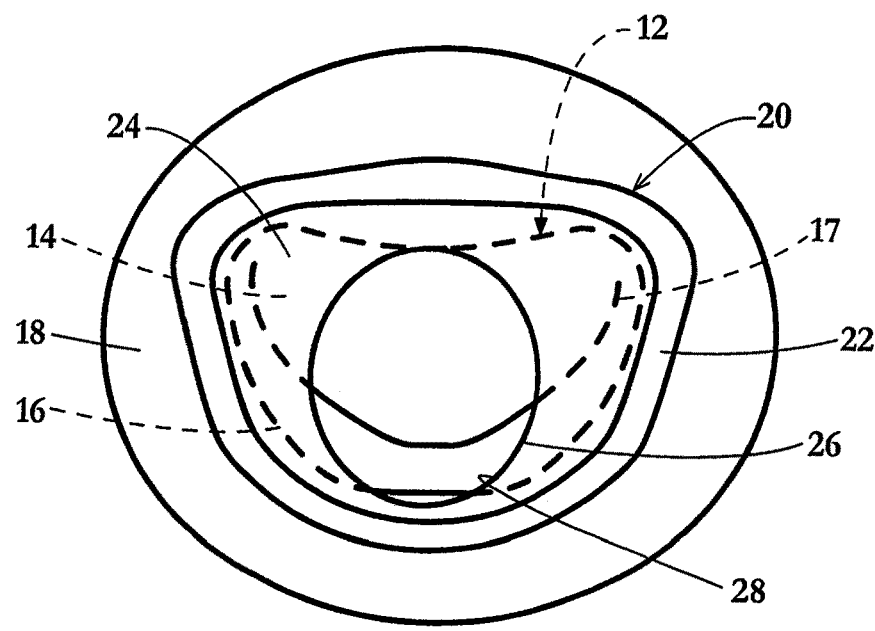
FIG. 3 is a view from the left atrium of the implantable scaffold fixed in position adjacent to a mitral valve.

Scaffold or mounting component 20 is implantable, for example, into the left atrium of a patient's heart, during a procedure to rectify and improve improper valve functioning. FIG. 3 shows scaffold 20 fixed in position over mitral valve 12.

Scaffold or support device 20 is comprises a generally rounded or somewhat oval body member (not separately designated), shown in FIGS. 2 and 3, which symmetric or asymmetric in two dimensions, but generally flat in the third dimension. Outer margin or rim element 22 is a pliable, conforming margin, which is generally continuous around the perimeter of the scaffold 20 and is able to take on a variety of shapes so that it can conform to the topography of the heart wall to which it is being attached. The scaffold device can be permanently fixed to the tissue.

Outer margin or rim element 22 is disposed generally in a plane and circumferentially surrounds pliant membrane 24, such that the margin is attached to the heart tissue and together with the membrane creates a barrier to blood flow. The barrier would be obstructive, were it not for orifice 28 in roughly the center of membrane 24, which is generally round and flexible but generally inelastic. Orifice 28 provides a neo-annulus into which a prosthetic or other valve can be inserted and attached to the scaffold or support device 20. Scaffold 20 provides a means of placing a valve into a site adjacent to a native valve annulus, in a way unencumbered by the limitations of the native valve annulus.

Figure 4:
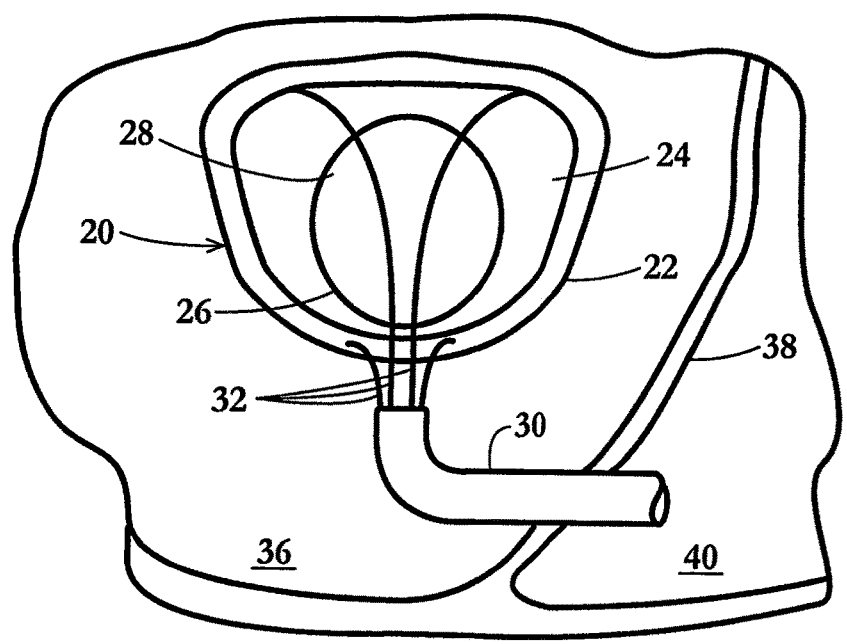
FIG. 4 is a view of a delivery system crossing the inter-atrial septum from the right atrium to deploy the device over the mitral valve.

FIG. 4 illustrates a delivery system and a means by which the outer margin or rim element 22 of scaffold or support device 20 can be fixed to the tissue of a heart or vessel wall, generally over or behind a heart valve such as mitral valve 12 of FIGS. 1 and 2. The delivery system includes a delivery catheter 30 and a plurality of guide wires, filaments, or cords 32 that are removably connected at their distal ends to outer margin or rim element 22. Guide wires, filaments, or cords 32 may be manipulated to shape outer margin or rim element 22 in-situ to match the contours of the surface to which the valve will be attached. Guide wires, filaments, or cords 32 are attached to various portions of the outer margin or rim element 22 at spaced points therealong. Guide wires, filaments, or cords 32 are used as manipulators to adjust the shape and position of the scaffold 20, and to hold it in position while the outer margin or rim element 22 is fixed to the adjacent tissue surface.

As schematically represented in FIG. 4, delivery catheter 30 may be inserted into the left atrium 36 by crossing the inter-atrial septum 38 from the right atrium 40 to deploy the valve scaffold or support device 20 over the mitral valve 12 (FIG. 3).

Figure 5:
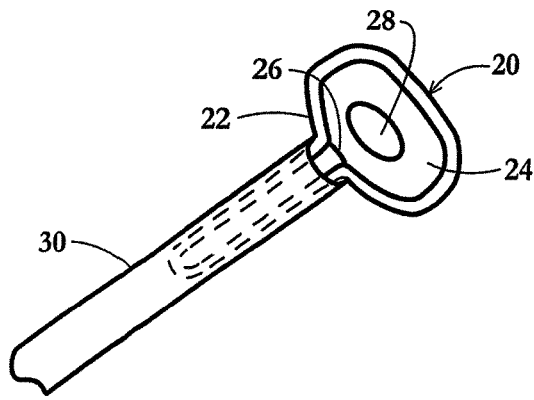
FIG. 5 is a view of a collapsed implantable scaffold in accordance with the invention emerging from the tip of the delivery system.

FIG. 5 depicts scaffold 20 in an intermediate stage of ejection from delivery catheter 30. At the onset of a percutaneous implantation procedure, when catheter is being manipulated through the vascular system, preferably the venous system, to the heart, scaffold 20 is stored in a collapsed configuration inside a distal end portion of the catheter. Alternatively, the collapsed scaffold may be inserted into a proximal end of the catheter and pushed to the distal end after the arrival of the distal end at the surgical site.

Figure 6:
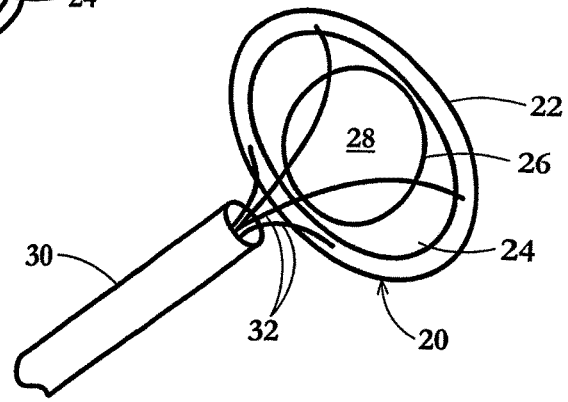
FIG. 6 is a view of a completely extruded implantable scaffold in accordance with the invention, having guide wires that are used to manipulate the scaffold for placing it in position.

FIG. 5 shows a partially expanded scaffold 20 emerging from the distal end of catheter 30 together with distal ends of a pair of guide wires, filaments, or cords 32. FIG. 6 similarly shows a completely ejected and expanded scaffold 20 outside the distal end of catheter 30 with several guide wires, filaments, or cords 32 extending from the lumen (not designated) of catheter 30 to outer margin or rim element 22.

Figure 7:
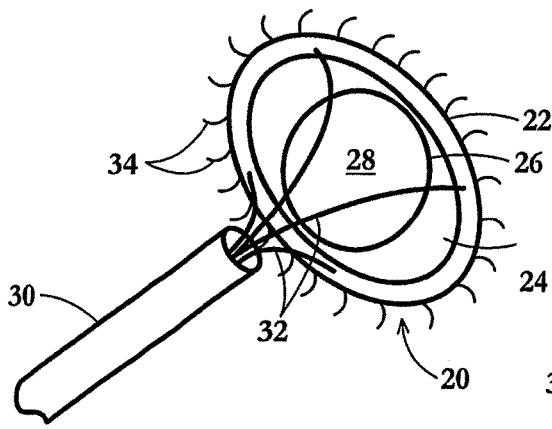
FIG. 7 is a view of an implantable scaffold component showing one embodiment for fixing the outer margin to the adjacent tissue walls.
Figure 8:
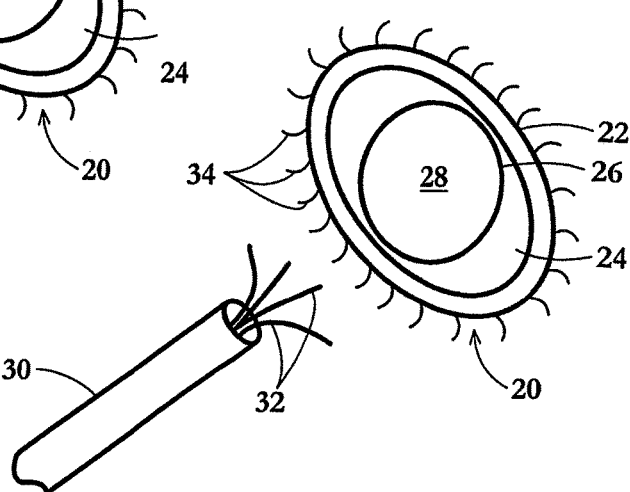
FIG. 8 is a view of the implantable scaffold component of FIG. 7 after fixation, and after release from the catheter delivery system, so that the neo-annulus is now capable of receiving a circular valve prosthesis through the same or another delivery system, though the valve prosthesis could also be surgically implanted.

As depicted in FIGS. 7 and 8, outer margin or rim element 22 may be pre-assembled with fixation elements 34, which engage heart tissue after the scaffold 20 is in position. Fixation elements 34 are spaced sufficiently close to one another to attach outer margin 22 circumferentially to the tissue so as to create a continuous or near continuous contact between the tissue and the scaffold 20. Fixation elements 34 may take any form suitable for achieving this result. Acceptable candidates include hooks, barbs, anchors, and aliquots of adhesive. The adhesive may be initially in an inert form and activated by the application of waveform energy, electromagnetic or ultrasonic, or possible heat energy. A separate instrument may be inserted into the heart chamber or guided to the surgical site for activating the adhesive.

Once implantation of scaffold or support device 20 has been completed, orifice 28 is ready to receive a circular or cylindrical valve prosthesis 42 (FIG. 9) through the same or another delivery system, though the valve prosthesis could alternatively be surgically implanted.

Annular inner margin or rim element 26 may be either elastic or inelastic with respect to its circumference and may be rounded or irregularly shaped and asymmetric, as appropriate to the valve morphology. In general, the combination of the implantable scaffold or support device 20 and the subsequently placed valve 42 (FIG. 9) will create complete separation between the chamber of fixation (e.g., 36) proximal and distal to the membrane margins, except for flow through the valve.

For purposes of facilitating a surface substantial enough to allow fixation of a valve 42, orifice 28 acting as the neo-annulus may have a cylindrical configuration, creating a surface rather than a rim. The cylindrical surface of the annulus extends perpendicularly to the plane of the membrane portion 24 of the scaffold device 20 and the plane of the native mitral annulus and in alignment with or parallel to the blood flow. The cylinder may be made of metal mesh, inelastic cloth, material elastic in only one plane (the plane of the blood-flow), a coil, or other appropriate material.

The cylindrical surface may be an integral part of the implanted scaffold 20, or may be attached by a separate step at some time-point after the scaffold has been deployed. Fixation to the inner margin or annular member 26 may be by compression, hooks, barb, or other appropriate means.

Valve scaffold or support device 20 may be provided with a means of tethering the sub-valvular apparatus into orifice 28 in order to take advantage of any potential contribution of the sub-valvular apparatus to cardiac function.

FIG. 9 depicts valve scaffold or support device 20 with outer conformable margin 22 fixed at the mitral annulus, an abbreviated membranous portion 24 separating the spaces, and cylindrical implanted valve 42 with apposed leaflets in profile resides within the neo-annulus.

Figure 10:
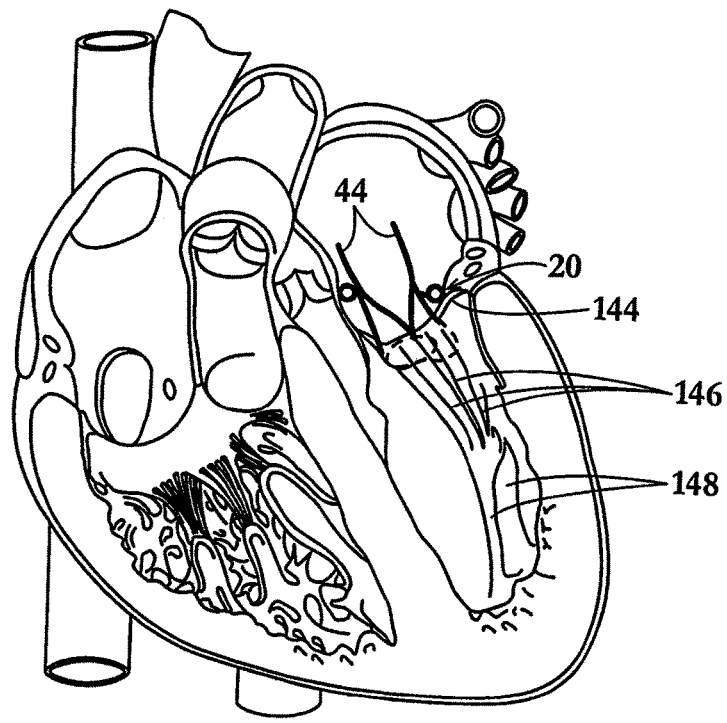
FIG. 10 is a photograph that shows loop tethers surrounding the cords, which in this iteration, are pulled though the neo-annulus so that with subsequent fixation of the valve, papillary function may continue to impact cardiac function.

FIG. 10 is a photograph that shows loop tethers 44 surrounding the cords or chordae tendineae 46 which in this iteration, are pulled though the neo-annulus orifice 28 so that with subsequent insertion and fixation of the valve 42, papillary function may continue to impact cardiac function.

Outer conformable margin 22 may be made of a pliant material, likely tubular in nature, in which fixation elements or fasteners 34 in the form of hooks, barbs, expandable anchors, or other appropriate attachment elements may be held. When the outer conformable margin or rim element 22 is positioned, fixation elements 34 are extended or otherwise deployed into the internal tissues of the atrial wall 18 to cause fixation. Parts of the outer conformable margin 22 may be attached either separately or all at one time. Outer margin 22 may be covered with a porous material such as polyester, or similar biocompatible covering to facilitate tissue ingrowth.

Alternatively the fixation elements or fasteners 34 may comprise hooks, barbs, screws, anchors, staples, magnets, glue, stents, or other fixation components that are delivered and deployed in part or totally separately from the implantable valve scaffold itself. Thus, valve scaffold 20 may be initially free of fixation elements or fasteners 34, with the fixation elements being attached in situ to the scaffold and the host tissue surface.

Commercially available valves, as well as those in development for catheter delivery and commercial availability in the future, are generally round, and, in the case of those designed for catheter delivery, are used either trans-arterially or trans-apically in the aortic position, but have not been used for the mitral valve replacement because of the asymmetry of the annulus and native valve. These devices cannot fit within the asymmetrical contours of a heart chamber. However, using scaffold 20, this asymmetrical chamber opening is converted to a round opening, thereby enabling existing round valve designs to be adapted for use in the mitral valve area.

Also, since the left atrium can be accessed through the venous system across the foramen ovale, it will accommodate a larger catheter than can generally be passed through the arterial side, and can address both the tricuspid and the mitral, neither of which now has a strategy for catheter-based replacement.

In general, a significantly larger valve may be required in the mitral position than in the aortic, and the valve 42 may be positioned into the orifice 28 of the neo-annulus by way of catheter 30, and expanded into the orifice. Orifice 28 may be a hole that receives and seats valve 42. Alternatively, orifice 28 may have valve connectors pre-assembled with scaffold 20 prior to placement to facilitate mounting. Alternatively, a standard prosthetic or bio-prosthetic valve may be sewn into place in an open procedure The primary use of scaffold 20 is in the mitral area. However, scaffold 20 may be adapted for use with the tricuspid, with slight modification to allow for the coronary sinus orifice. Of course, scaffold 20 can be adapted for providing a neo-annulus in any location where such a neo-annulus would have therapeutic value. As the membranous portion 24 can vary in size depending on the discrepancy in size between the desired valve and the dimensions of the surrounding tissue to which the scaffold will be fixed, and the outer margin 22 is conformable to virtually any irregular contour opening, it is clear that scaffold 20 is adaptable for location in many areas of the body, and is not limited to the particular embodiments shown and described herein, as would be understood by one skilled in the art.

Figure 11:
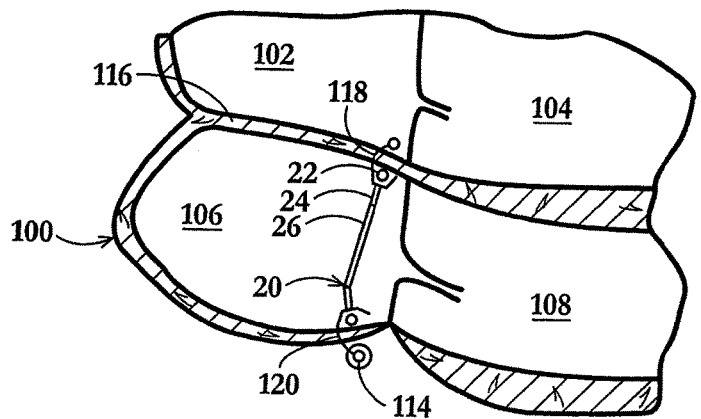
FIG. 11 is a diagram showing a four-chamber view of the heart with the margin of an implantable scaffold in accordance with the invention fixed through the coronary sinus and the atrial septum.

FIG. 11 diagrammatically depicts a heart laving a right atrium 102, a right ventricle 104, a left atrium 106, and a left ventricle 108, with valve scaffold or support platform 20 implanted therein. Outer margin or perimeter element 22 is fixed via fasteners 118 and 120 through the coronary sinus 114 and the atrial septum 116.

Figure 12:
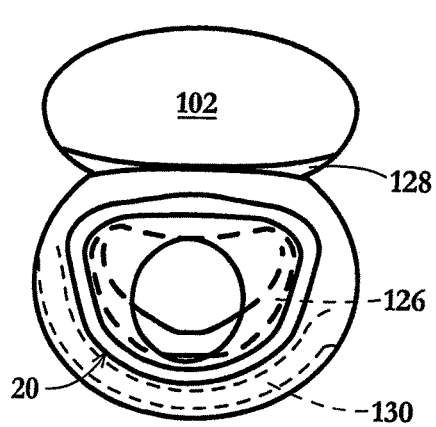
FIG. 12 is a schematic view of the mitral valve and atrial septum from the dome of the atrium. The tricuspid valve is not illustrated. The route of the coronary sinus is shown under the left atrial wall and roughly parallel to the posterior annulus.

FIG. 12 schematically illustrates a mitral valve 126 and atrial septum 128 from the dome of the left atrium 106 (FIG. 11) with scaffold or valve support device 20 in position in the atrium adjacent the mitral valve. The tricuspid valve is not illustrated. The route of the coronary sinus 130 is shown under the left atrial wall and roughly parallel to the posterior annulus.

Figure 13:
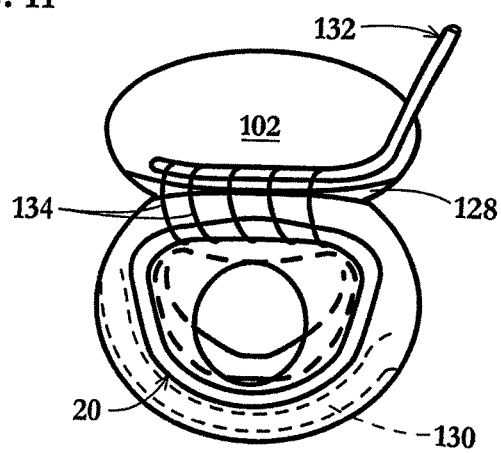
FIG. 13 is a schematic view similar to FIG. 12, illustrating a separate device passed into the right atrium equipped with fixation elements, which can attach to a portion of the margin of the scaffolding for partial anterior fixation.
Figure 14:
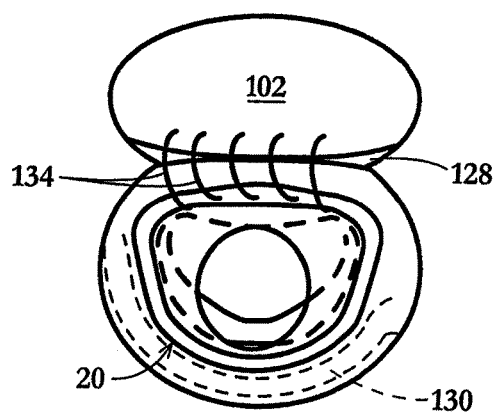
FIG. 14 is a schematic view similar to FIGS. 12 and 13, showing a scaffold is a schematic view similar to FIG. 12 fixed through the atrial septum as a result of the right atrial device used in FIG. 13.

As shown in FIG. 13, a separate device 132 may be passed into the right atrium 106 equipped with fixation elements 134, which can attach to a portion of the outer margin or rim element 22 of scaffold or valve platform 20 for partial anterior fixation. FIG. 14 shows scaffold or valve platform 20 fixed through the atrial septum 128 as a result of the right atrial device 132 used as depicted in FIG. 13.

Figure 15:
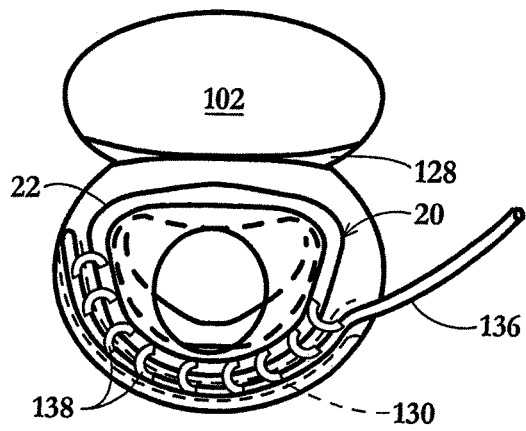
FIG. 15 is a schematic view similar to FIG. 12, illustrating a separate device passed into the coronary sinus equipped with fixation elements, which can attach to the margin of the scaffolding for partial posterior fixation.
Figure 16:
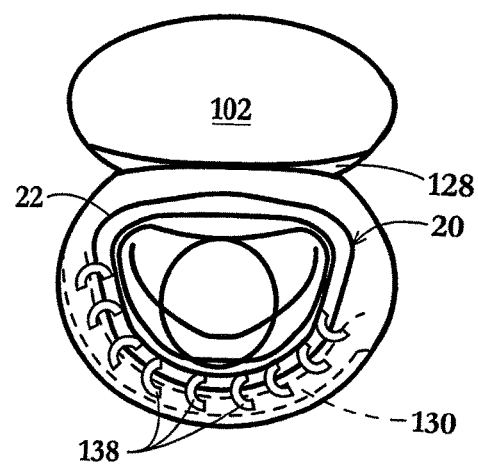
FIG. 16 is a schematic view similar to FIG. 15, showing a scaffold in accordance with the invention fixed through the atrial wall through the coronary sinus as a result of the coronary sinus device used in FIG. 15.

As illustrated in FIG. 15, another surgical device 136 equipped with fixation elements 138 is passed into the coronary sinus 130. Fixation elements 138 attach to the outer margin or rim element 22 of scaffold or valve support platform 20 for partial posterior fixation. FIG. 16 shows scaffold or valve support platform fixed through the atrial wall via the coronary sinus 130 as a result of the coronary sinus device 136 used as depicted in FIG. 15.

Figure 17:
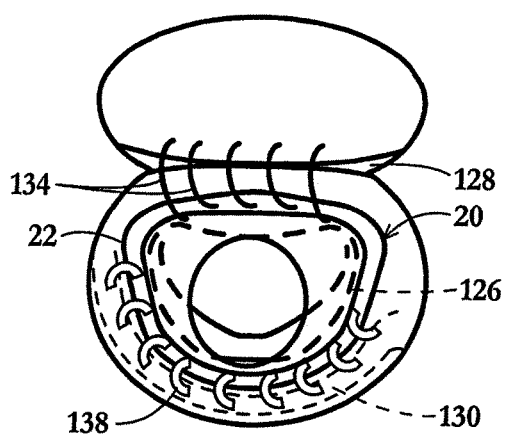
FIG. 17 is a schematic view similar to FIGS. 14 and 16, showing the scaffold fixed through both the atrial septum and the coronary sinus as a result of the right atrial device used in FIG. 13 and the coronary sinus device shown in FIG. 15.

FIG. 17, a schematic view similar to those of FIGS. 14 and 16, shows scaffold or valve support platform 20 secured in position next to the mitral valve 126 (A) by fixation elements or fasteners 134 extending through the atrial septum 128 as a result of the use of the right atrial device 132 pursuant to FIG. 13 and (B) by fixation elements or fasteners 138 extending from the coronary sinus 130 as a result of the use of the coronary sinus device pursuant to FIG. 15.

Figure 18:
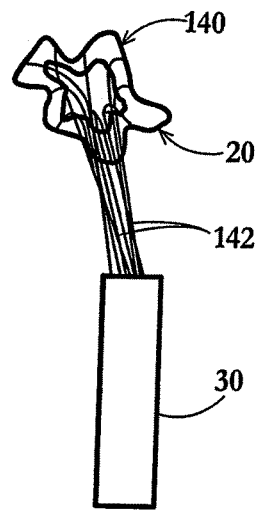
FIG. 18 is a schematic top plan view showing a collapsed valve scaffold device in accordance with the invention emerging from a distal end of the delivery catheter. In this iteration, a series of tethers or cords attached either to the margin, through the membranous portion, or more centrally, and are used to propel and position the scaffolding into place around the annulus.
Figure 19:
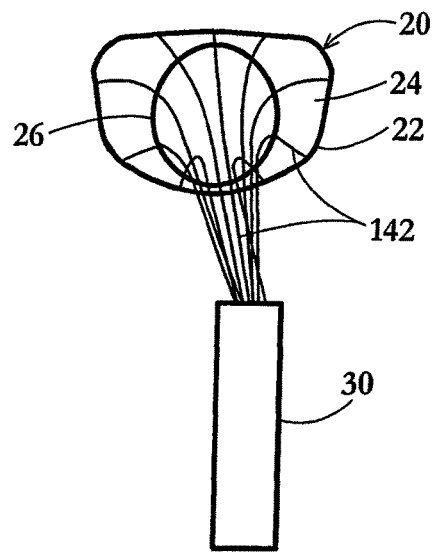
FIG. 19 is a schematic view similar to FIG. 18, showing the expanded implantable valve scaffold maneuvered into position by one or more guiding cords, tethers, guide wires or filaments, which allow advancement or retraction of any portion of the margin of the implantable into apposition with the tissue at the desired location.

FIG. 18 shows a collapsed configuration 140 of valve scaffold or support device 20 emerging from a distal end of delivery catheter 30. In this iteration, a series of tethers, cords, wires or filaments 142 are attached either to outer margin 22, the membranous portion 24, or more centrally, and are used to propel and position the scaffold or valve support device 20 into place around the annulus. Scaffold 20 expands automatically by virtue of the internal stresses of the shape memory material such as titanium and nitinol of which the scaffold is fabricated. FIG. 19 depicts the expanded implantable valve scaffold 20 maneuvered into position by one or more guiding cords, tethers, wires or filaments 142, which allow advancement or retraction of any portion of the outer margin 22 of the implantable scaffold 20 into apposition with the tissue at the desired location.

Figure 20:
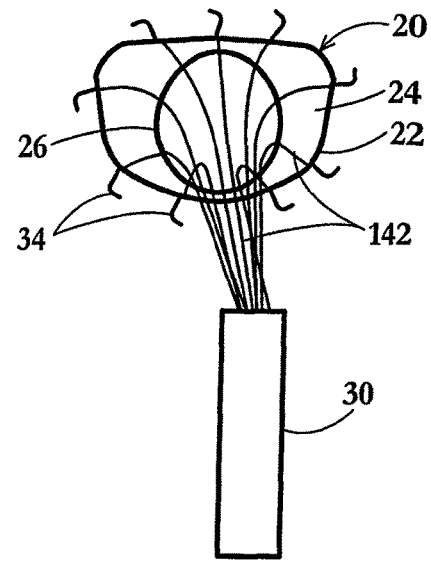
FIG. 20 is a schematic view similar to FIG. 19, showing the guiding cords, tethers, wires or filaments, advanced or else a fixation device at the end of each cord, tether, guide wire or filament is advanced at the margin to perforate the tissue and accomplish fixation. The fixation portion may be a detachable portion of the guides, or a separate element either advanced by or over the guides.
Figure 21:
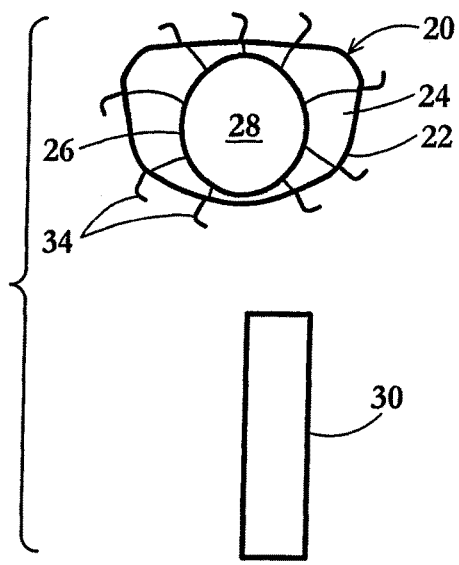
FIG. 21 is a schematic front elevational view of the implantable scaffold of FIGS. 19 and 20, showing the cords as retracted into the catheter so as to leave the deployed, fixed implantable valve scaffold with the neo-annulus located centrally over the native valve (not shown).

FIG. 20 diagrammatically shows the guiding cords, tethers, wires or filaments 142 and a fixation element or fastener 34 at the end of each cord, tether, guide wire or filament advanced at the margin 22 to perforate the tissue and accomplish fixation. Fixation elements or fasteners 34 may be detachable portions of cords, tethers, guide wires or filaments 142, or separate elements advanced either by or over the guides 142. In FIG. 21 cords, tethers, guide wires or filaments 142 have been retracted into the catheter 30 so as to leave the deployed, fixed implantable valve scaffold 20 with the valve-receiving orifice or neo-annulus 28 located centrally over the native valve (not shown).

Figure 22:
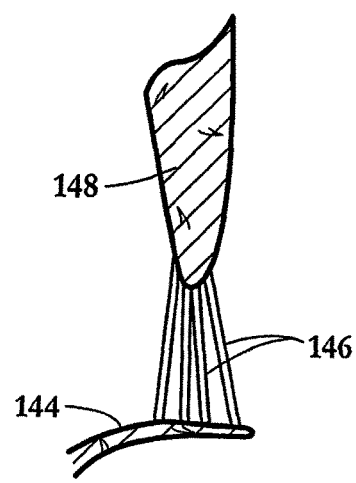
FIG. 22 is a diagram showing the mitral or tricuspid leaflet, with the cords and papillary muscle depicted in a long axis view.

FIG. 22 is a diagram showing a mitral or tricuspid leaflet 144, with the cords or chordae tendineae 146 and papillary muscle 148 depicted in a long axis view.

Figure 23:
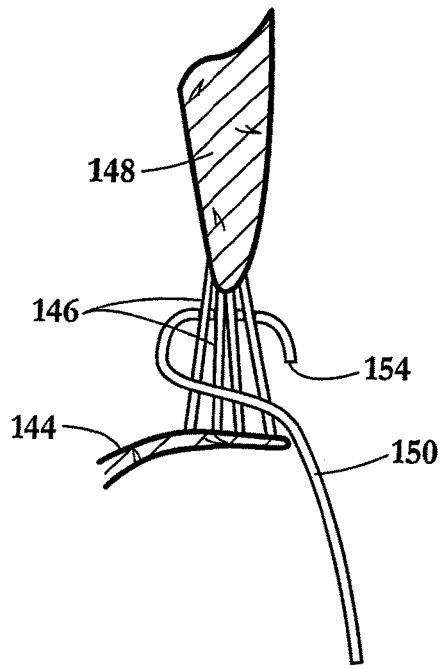
FIG. 23 is a diagram similar to FIG. 22, showing a pre-formed or steerable catheter passed around the cords or papillary muscle. In this view, the catheter is coming from the atrium, but the catheter could alternatively pass through the ventricular wall or ventricular outflow valve.
Figure 24:
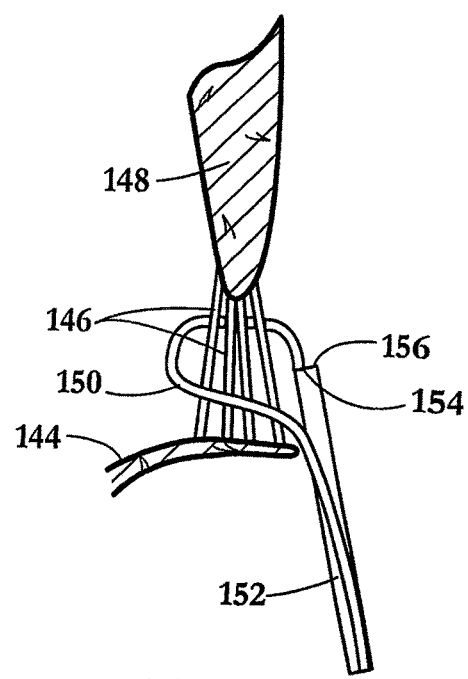
FIG. 24 is a diagram similar to FIGS. 22 and 23, showing a second, sliding catheter passed over or adjacent to the shaft of the first catheter, or by some other route or guidance system, such that the open distal ends of the two catheters appose, creating a continuous lumen.

As shown in FIG. 23, a pre-formed or steerable catheter 150 is passed around the cords 146 and/or papillary muscle 148. In this view, catheter 150 extends from the atrium 102 or 106 (FIG. 11), but the catheter could alternatively pass through the ventricular wall or ventricular outflow valve. As shown in FIG. 24, a second, sliding catheter 152 is passed over or adjacent to the shaft of the first catheter 150, or by some other route or guidance system, such that open distal ends 154 and 156 of the two catheters appose, creating a continuous lumen.

Figure 25:
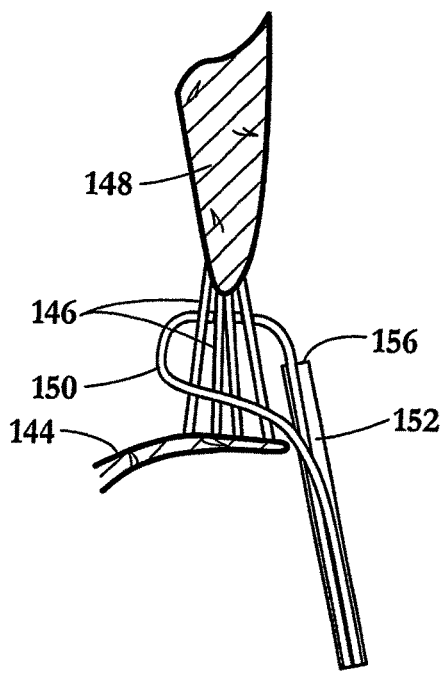
FIG. 25 is a diagram similar to FIGS. 22-24, showing a continuous tether passed through the looping and sliding catheters, retrieved out the proximal ends of the catheters.
Figure 26:
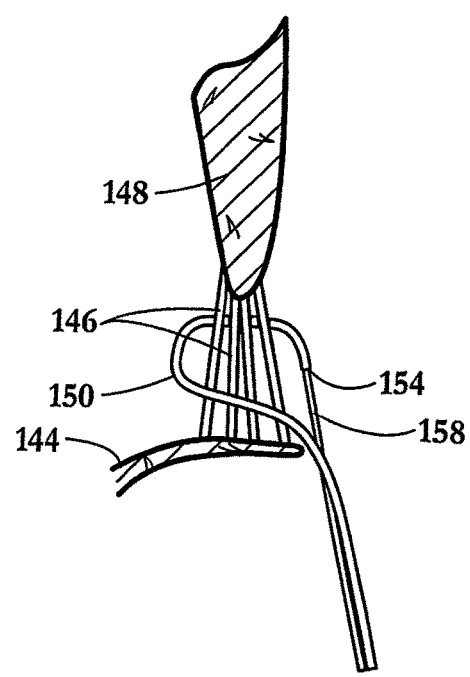
FIG. 26 is a diagram similar to FIGS. 22-25, showing that the second, sliding catheter has been removed revealing one part of the tether surrounding the cords
Figure 27:
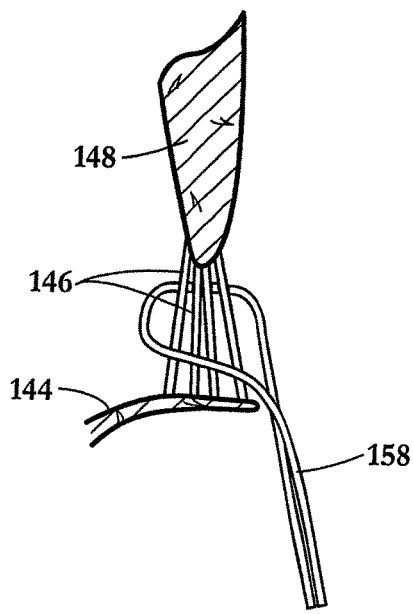
FIG. 27 is a diagram similar to FIGS. 22-26, showing that the preformed or steerable catheter, which previously surrounded the sub-valvular apparatus, has been removed revealing the free tether surrounding the cords, available for incorporation into the scaffold or valve.

Pursuant to FIG. 25 a continuous tether 158 is passed through looping catheter 150 and sliding catheter 152, via their apposed distal ends 154 and 156, and extends out the proximal ends (not shown) of the catheters. In FIG. 26 sliding catheter 152 has been removed, revealing one part of tether 158 surrounding the cords 146. In FIG. 27 preformed or steerable catheter 150, which previously surrounded the sub-valvular apparatus 146, 148, has been removed, revealing tether 158 free and surrounding the cords 146, available for incorporation into scaffold 20 or valve 42 (FIG. 9). Pursuant to one option, tether 158 extends through orifice or neo-annulus opening 28 prior to the seating of the prosthetic or bio-prosthetic valve 42. Upon the seating of valve 42, tether 158 is pinched or clamped between inner margin or rim element 26 (see, e.g., FIG. 2) and the seated valve.

The tethering of scaffold 20 and valve 42 to the subvalvular apparatus, i.e., cords 146 and/or papillary muscle 148, serves in part to anchor the implanted devices 20 and 42 in position in opposition to the pressure exerted during ventricular systole. In addition, the anchoring preserves the natural distribution of stresses throughout the heart and accordingly reduces the likelihood of cardiac failure owing to an imbalance in the forces affecting the heart muscles.

Figure 28:
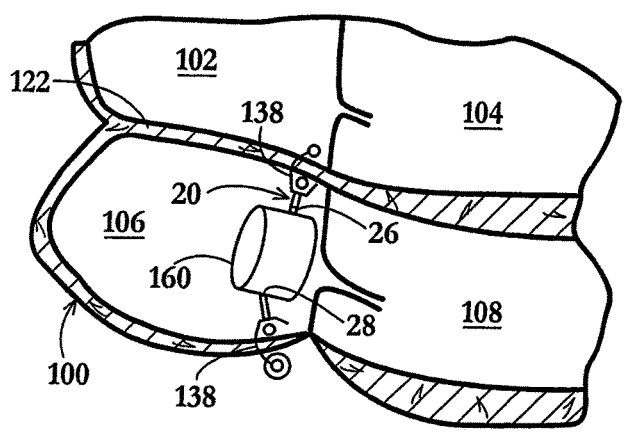
FIG. 28 is a diagram showing a four-chamber view of the heart with a cylindrical sheath, framework, or other support added at a neo-annulus of an implantable scaffold in accordance with the invention to act as a landing zone for a subsequently placed valve

FIG. 28 is a diagram similar to FIG. 11 and utilizes the same reference designations for corresponding structures. As depicted in FIG. 28, a cylindrical sheath, framework, or other support 160 is inserted into a neo-annulus orifice 28 of scaffold 20 to act as a landing zone for a subsequently placed prosthetic or bio-prosthetic valve (not shown). Tether 158 may be clamped between orifice margin or rim element 26 and cylindrical sheath, framework, or support 160. Sheath, framework, or support 160 provides increased surface area for attachment of an off-the-shelf valve and may be provided with fasteners (not shown) to securely link to margin or rim element 26.

Figure 29:
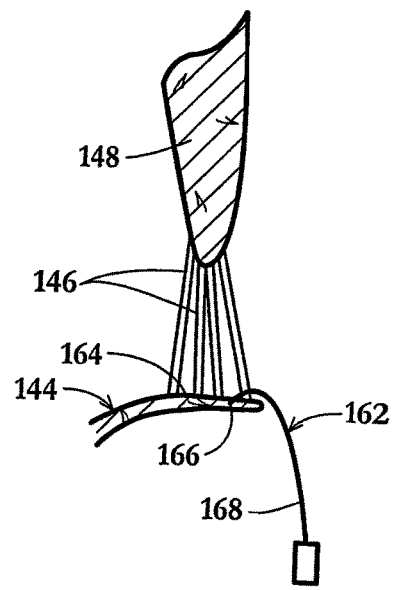
FIG. 29 is a diagram similar to FIG. 22 but showing an alternative embodiment for capture of the sub-valvular apparatus where an element is delivered to the underside of the valve leaflet (shown as a single barb on a single leaflet), to engage the valve on or near the attachment of the cordae, allowing an extension of the barb to attach to the scaffolding or neo-annulus allowing transmission of papillary systolic forces to the valve.

FIG. 29 shows an alternative embodiment for capture of the sub-valvular apparatus, including chordae tendineae 146 and papillary muscle 148, where a fastening element 162 is delivered to the underside 164 of valve leaflet 144 (shown as a single barb on a single leaflet), to engage the mitral valve on or near the attachment of the cordae. Fastening element 164 may take the form of a hook or barb 166 at the end of a tether 168. The hook or barb 166 is inserted into the tissue of the leaflet 144 and secured thereto along underside 164 or to cordal junctions. Tether 168 is left in place for incorporation into scaffold 20 or anchoring to the scaffold and the prosthetic valve, allowing transmission of papillary systolic forces to the valve.

Figure 30:
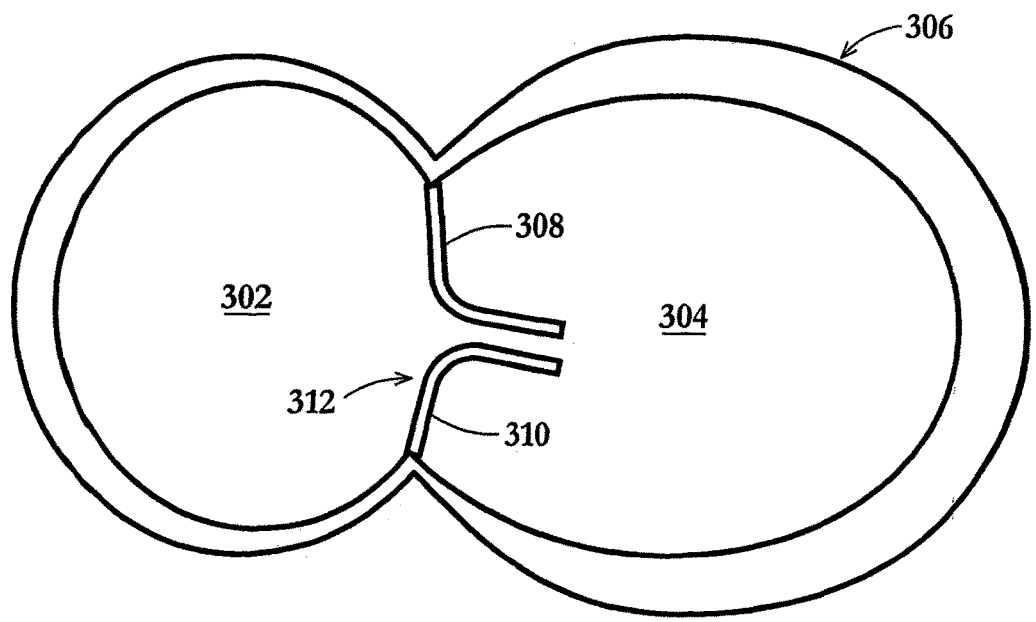
FIG. 30 is a schematic cross-sectional view of the left atrium and left ventricle of a heart, showing mitral valve leaflets in a nearly closed configuration.
Figure 31:
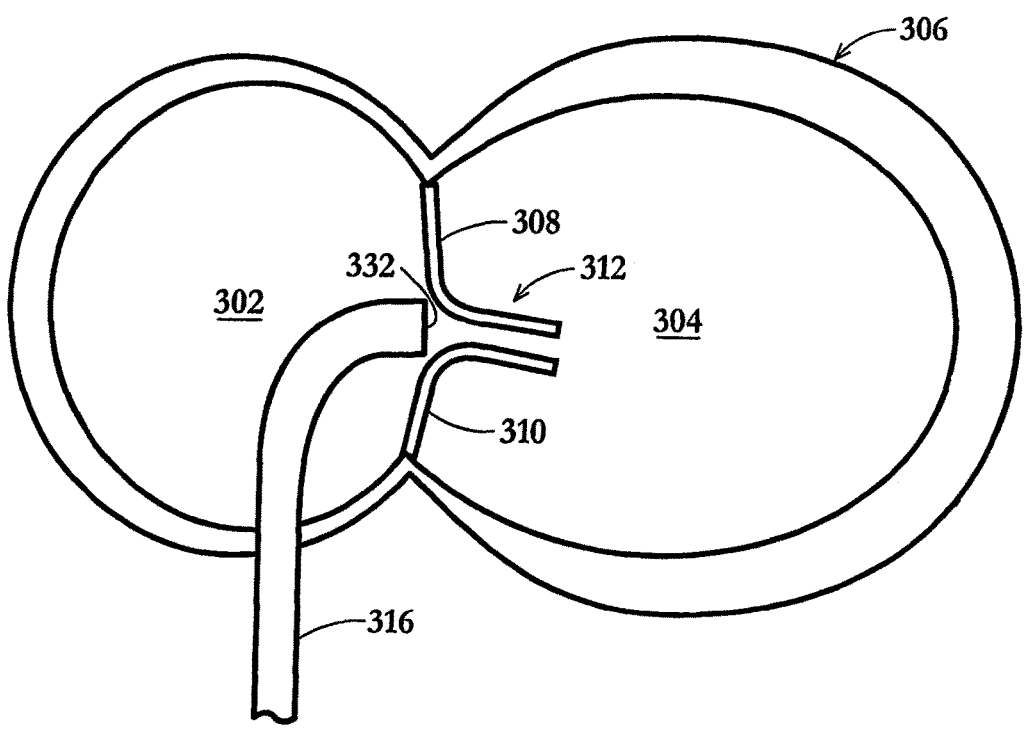
FIG. 31 is a schematic view similar to FIG. 29, showing a delivery catheter passed across the inter-atrial septum from the right atrium into the left atrium.

FIGS. 30 through 36 represent successive stages of a procedure for implanting an alternative valve scaffold 300 in accordance with principles delineated herein. FIG. 30 depicts a left atrium 302 and left ventricle 304 of a heart 306, showing leaflets 308 and 310 of a mitral valve 312 in a partially closed configuration representing a malfunctioning of the mitral valve. In a procedure deploying a prosthetic valve 314 (FIG. 36) to effectively replace the mitral valve 312, a delivery catheter 316 is passed across the inter-atrial septum 318 from the right atrium 320 into the left atrium 302, as shown in FIG. 31.

A distal end portion of catheter 316 carries valve scaffold or mounting platform 300 in a collapsed configuration (not shown). As described hereinafter with reference to FIGS. 32-34, the scaffold or platform 300 is ejected and expanded in stages to displace leaflets 308 and 310 outwardly, to fold or curl the leaflets into a more compact configuration and to attach the scaffold or frame to the leaflets. Scaffold 300 is made of at least one shape memory material so that the expansion and reconfiguration of the scaffold occurs automatically in response to the ejection of the scaffold from a distal tip 322 of catheter 316.

Figure 32:
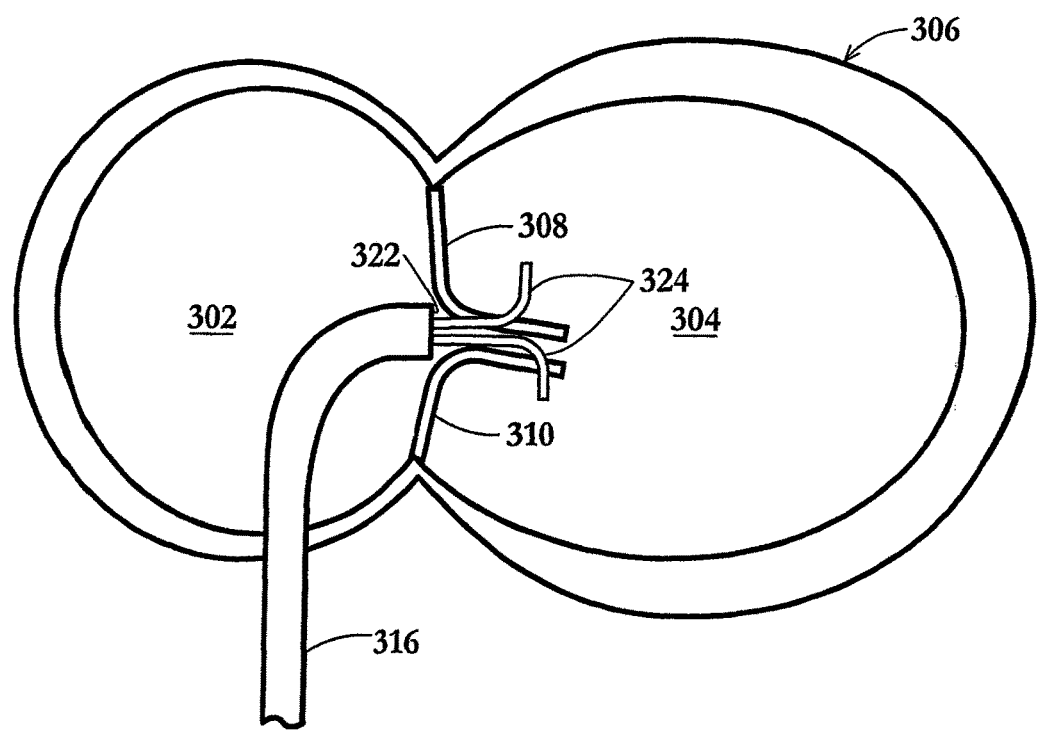
FIG. 32 is a schematic view similar to FIG. 30, showing an early stage of an implantation procedure wherein expanding ventricular fixation hooks of a collapsed valve-seating scaffold in accordance with another embodiment of the invention extend out of a distal end of the delivery catheter of FIG. 30.
Figure 33:
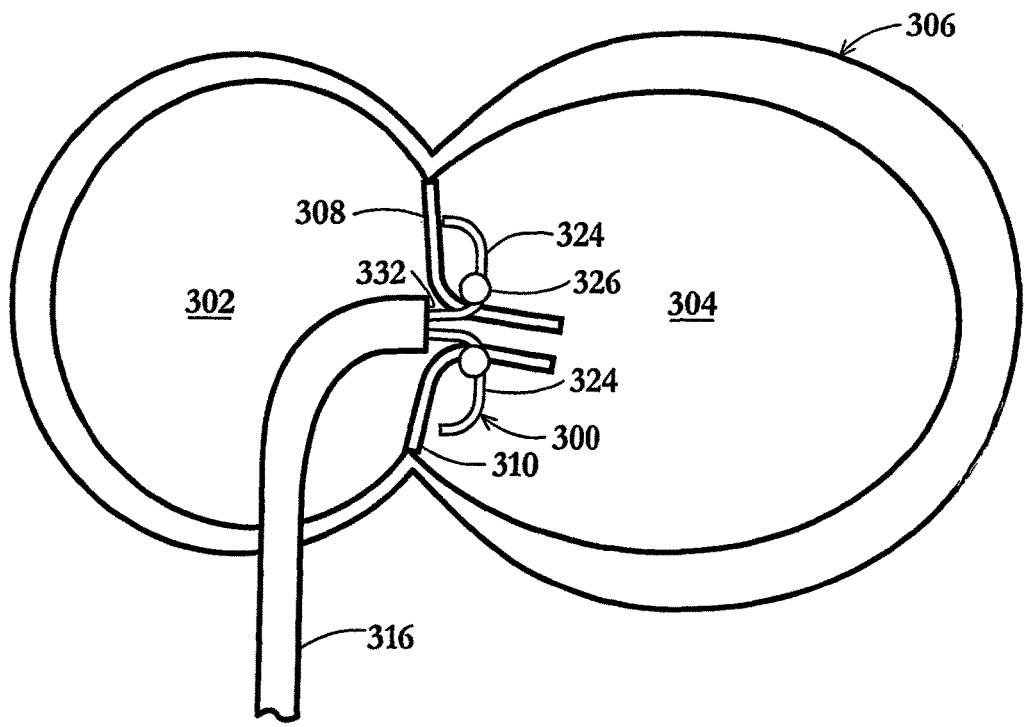
FIG. 33 is a schematic view similar to FIG. 31, showing an intermediate stage of an implantation procedure wherein a partially expanded annular member of the scaffold is disposed generally between the mitral valve leaflets and wherein the ventricular fixation hooks of FIG. 31 extend from the annular member behind the mitral valve leaflets.
Figure 34:
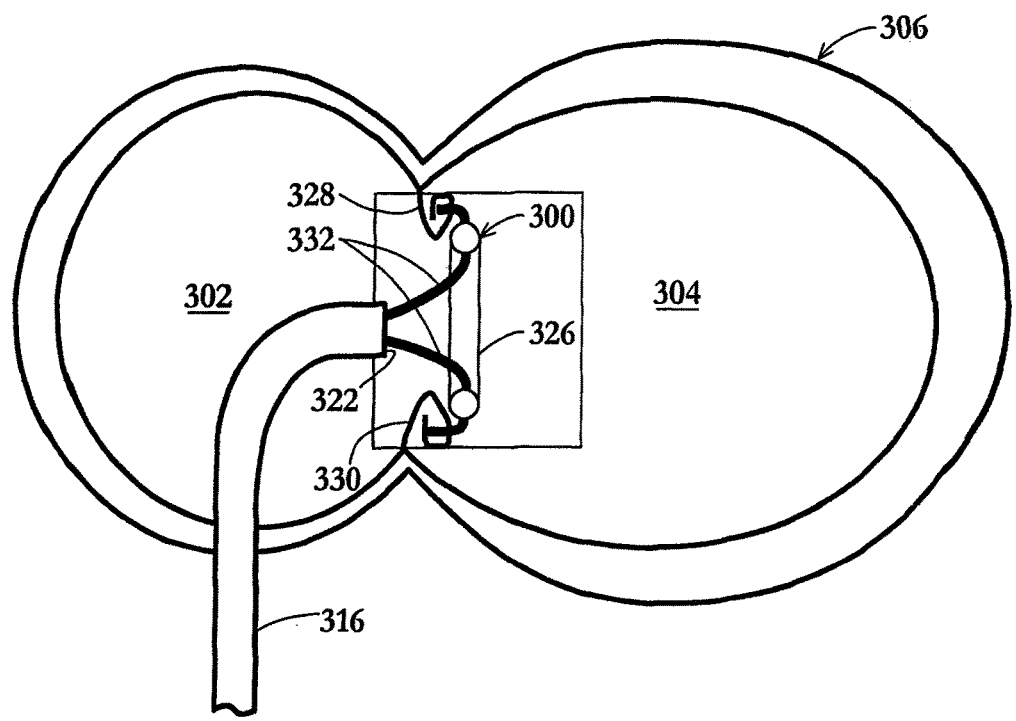
FIG. 34 is a schematic view similar to FIG. 32, showing a later intermediate stage of the implantation procedure wherein the annular member of the scaffold is further expanded and the mitral valve leaflets are folded or curled into a compact configuration and wherein the ventricular fixation hooks of FIGS. 31 and 32 are attached to the mitral valve leaflets.
Figure 37:
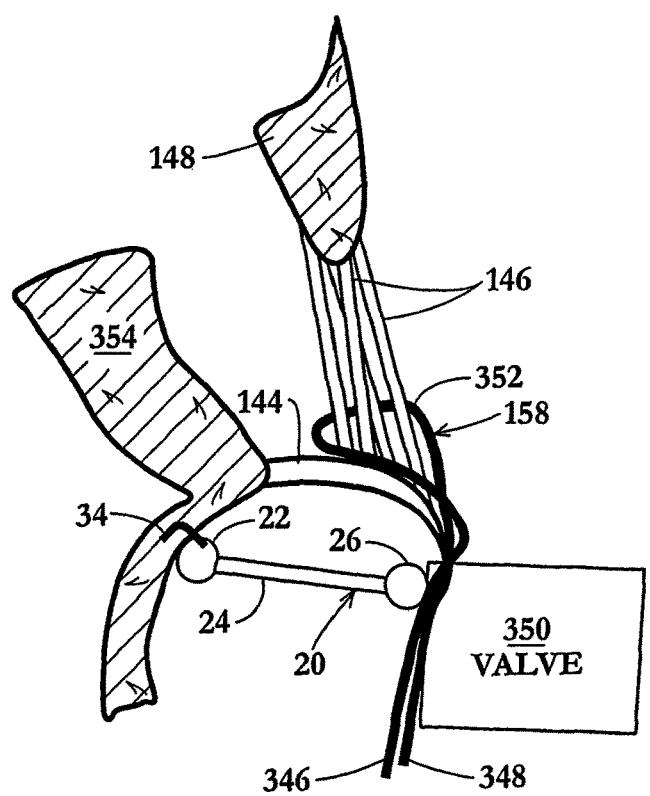
FIG. 37 is a diagram similar to FIG. 27, showing the two-strand tether surrounding the cords, inserted between the scaffold and valve.

After a maneuvering of catheter 315 so that distal tip 322 thereof is juxtaposed to mitral valve 312, as depicted in FIG. 32, the collapsed scaffold or valve-mounting platform 300 is pushed in the distal direction relative to catheter 316 so that a plurality of ventricular fixation hooks 324 of the scaffold emerge from the distal tip of the catheter and insert between the valve leaflets 308 and 310. Upon continued ejection of the collapsed scaffold 300 from catheter tip 322, an annular member 326 of the scaffold emerges into the gap between leaflets 308 and 310, as shown in FIG. 33. The ejected annular member 326 automatically expands thereby folding leaflets 308 and 310 outwardly into curled configurations 328 and 330, as illustrated in FIG. 34. During or immediately prior to this expansion of annular member 326, ventricular fixation hooks 324 pivot towards the curling or folding leaflets 308 and 310 and insert their distal tips between the chordae tendineae into the mitral valve tissues, thus attaching annular member 326 to the mitral valve leaflets 308 and 310 on the ventricular side thereof. FIG. 37 further illustrates an emergence, from catheter tip 322, of a plurality of atrial fixation hooks 332 that are connected to annular member 326. The distended atrial fixation hooks, 332, to the extent that they are still entrained by friction forces to the delivery catheter 316, may be used to fine tune the positioning of the scaffold 300 by maneuvering catheter 316 to exert displacement forces on the scaffold via the extended and deformed atrial fixation hooks.

Figure 35:
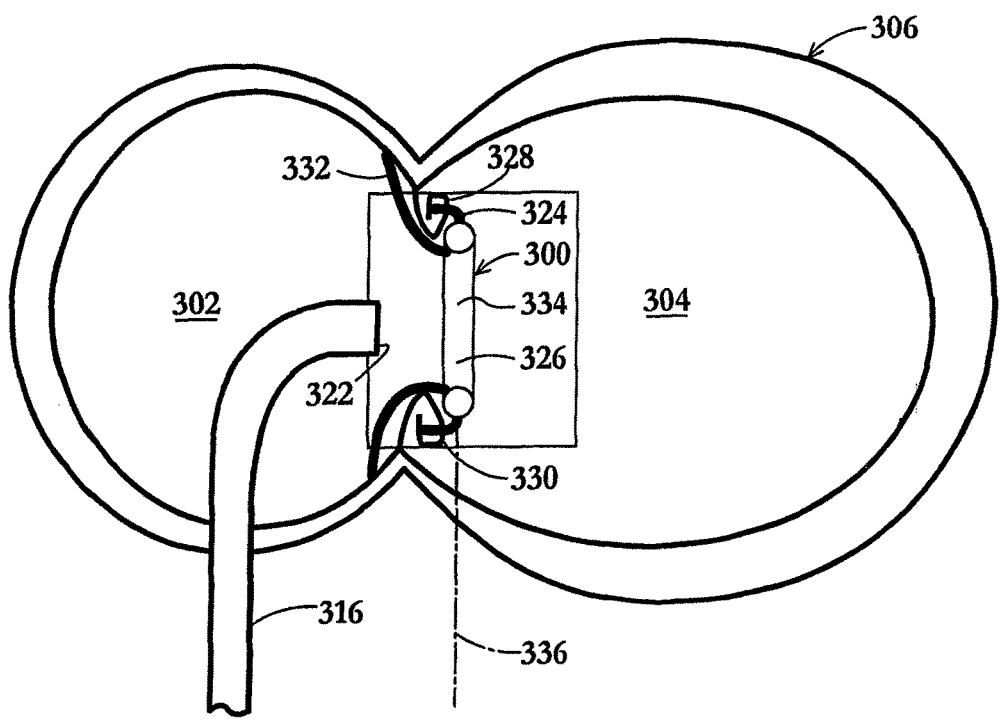
FIG. 35 is a schematic view similar to FIG. 34, showing in a still later intermediate stage of the implantation procedure wherein the scaffold is completely ejected from the delivery catheter and wherein now deployed atrial fixation hooks are extend from the annular member into the atrial chamber and are connected to the mitral valve leaflets.

FIG. 35 shows a late stage of an the implantation procedure wherein scaffold 300 is completely ejected from delivery catheter 316 and wherein atrial fixation hooks 332 have been completely ejected from catheter 317 so that the hooks can assume a predetermined clamping or attachment orientation with distal tips of the hooks inserted into the atrial or mitral-valve tissues on the atrial side of the folded or curled configurations 328 and 330 of the mitral valve leaflets 308 and 310.

Figure 36:
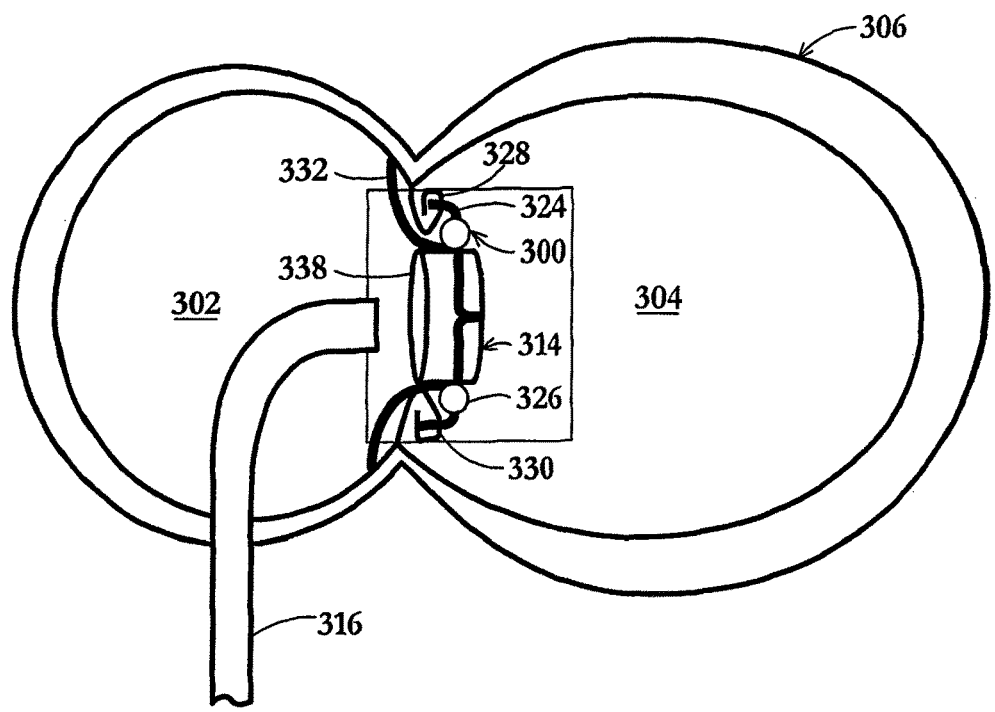
FIG. 36 is a schematic view similar to FIG. 35, showing terminal stage of the implantation procedure wherein a prosthetic valve is seated in the orifice of the valve scaffold.

Annular member 326 of scaffold 300 defines a neoannulus orifice 334 for receiving or seating prosthetic or bio-prosthetic valve 314 (FIG. 36). Ventricular fixation hooks 324 and atrial fixation hooks 332 are fasteners connected at least indirectly to the annular member for attaching the same all around an outer margin thereof to an tissue surface in the left atrium 302 and to a tissue surface in the left ventricle 304. The tissue surfaces may belong to the atrial leaflets or to the heart chamber walls.

Annular member 326 has a transverse dimension or thickness extending perpendicularly to a major plane 336 (FIG. 35) of the annular member. Ventricular hooks or fasteners 324 extend from the annular member 326 outwardly to one side of plane 336, towards the ventricle 304, while atrial fixation hooks or fasteners 332 extend from the annular member outwardly to an opposite side of plane 336, towards the left atrium 302. Hooks or fasteners 324 and 332 define a space therebetween for receiving and constraining curled configurations 328 and 330 of leaflets 308 and 310.

Annular member 326 and hooks or fasteners 324 and 332 are sized and configured to so constrain the curled configurations 328 and 330 of mitral valve leaflets 308 and 310 that a satisfactory liquid tight seal is created between the curled or folded leaflets and the scaffold 300. Hooks or fasteners 324 and 332 are each made of a shape memory material such as Nitinol, while annular member 326 is made of the same or a different shape memory material such as braided titanium.

When the implantable scaffold 3s disposed in a collapsed delivery configuration inside the distal end portion of delivery catheter 316, the annular member 326 assumes an elongate squashed shape such as that assumed by a collapsed rubber band. The shape memory material of annular member 326 is flexible but not elastic. Annular member 326 is substantially rigid in the finally expanded configuration wherein neo-annulus orifice 334 is sized to seat prosthetic or bio-prosthetic valve 314 in a liquid tight fit.

FIG. 36 depicts a terminal stage of the implantation procedure wherein leaflets 308 and 310 and mitral valve cords (not shown) are fixed to annular member 326 and wherein prosthetic or bio-prosthetic valve 314 is seated in orifice 334 of the valve scaffold 300. Annular member 326 may be provided with an annular lip or ridge (not shown) which is received in a groove (not shown) on a external wall 338 of valve 314, to enhance of implement formation of a liquid-tight seal.

Hooks or fasteners 324 and 332 are circumferentially spaced about the annular member 326 with an inter-hook spacing of 1-3 mm. Hooks or fasteners 324 and 332 may take any form suitable for attachment to ventricular, mitral valve and atrial tissues. The fasteners 324 and 332 may be barbs, anchors, claws, or clips instead of or in addition to hooks.

It is contemplated that hooks or fasteners 324 and 332 are pre-connected to annular member 326 during the manufacturing process at the factory. However, it is possible for one or more hooks 324 and/or 332 to be attached to annular member 326 in situ, as a step of the implantation procedure. It is contemplated that the procedure of FIGS. 30-36 is percutaneous. However, essentially the same procedure may be conducted via open heart surgery in appropriate cases.

FIG. 37 shows two strands 346 and 348 of the tether 158 of FIG. 27 extending between the inner margin or rim element 26 of scaffold 20 and a prosthetic valve 350. The procedure of FIGS. 22-27 represents one of several ways of anchoring the subvalvular apparatus (cords or chordae tendineae 146 and papillary muscle 148) to the scaffold 20 and valve 350. Tether 158 forms a noose 352 that is passed around cords 146. There are three kinds of cords: primary and secondary, which come off the papillary muscles, and tertiary, which come off the wall 354 of the left ventricle. Noose 352 can capture at least most, if not all, of the primary cords and probably most of the secondary cords. Strands or segments 348 and 348 of tether 158 are placed under tension as valve 350 is seated in orifice or neoannulus 28 and with echocardiographic monitoring, the tension may be adjusted until the systolic shortening caused by the cords pull on scaffold 20.

As depicted in FIG. 38, a fastener 356 may be advanced over both strands or segments 348 and 348 of tether 158 to secure the tether in position relative to the scaffold 20 and valve 350. Fastener 356 acts to compress or clamp the tether strands 346 and 348 at the site of contact with scaffold 20 or more particularly inner margin or rim element 26, acting like a nut of a bolt, so that the fastener, by virtue of its size, holds the noose strands of segments 346 and 348 against the scaffold. Fastener 356 may be coated with material that s blood compatible. Strands or tether segments 346 and 348 are severed at fastener 356 with an end-cutting device (not shown).

Figure 41:
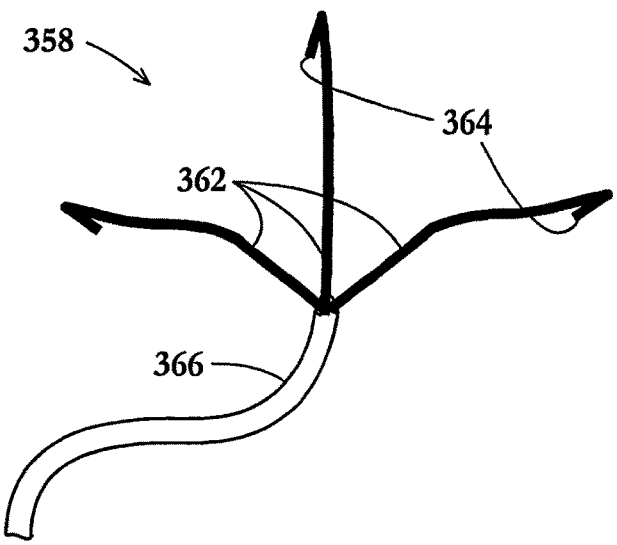
FIG. 41 is a top plan view of the grappling hook of FIGS. 39 and 40.

FIGS. 39-41 show a grappling hook device 358 that forms a particular embodiment of the fastening element 162 described hereinabove with reference to FIG. 29. Hook device 358 includes a stem 360 from which emanate three prongs or fingers 362 each provided at a free end with a hook or barb 364. FIGS. 39-41 depict hook device 358 in an expanded use configuration wherein prongs or fingers 362 are each generally C-shaped and are disposed in respective planes (see FIG. 41) oriented at an angle of about 30° to 60° relative to each other. A tension member or tether 366 is connected to stem 360.

Stem 360 and prongs or fingers 362 are made of a shape memory material such as nitinol, so that hook device 358 may be delivered in a collapsed configuration to an atrial site through a small diameter catheter and deployed through the orifice or neoannulus 28 of scaffold 20.

Figure 42:
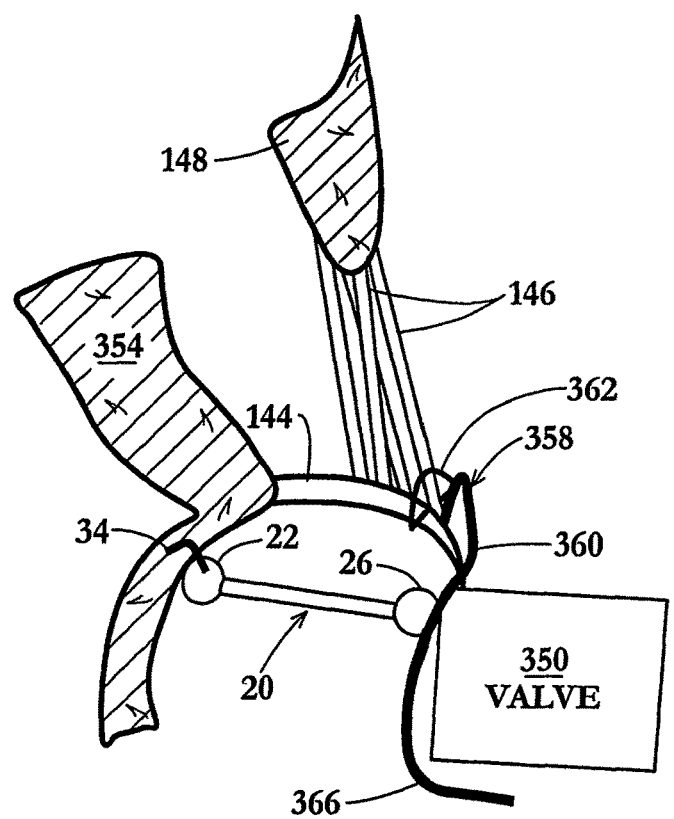
FIG. 42 is a schematic view similar to FIG. 37, showing use of the grappling hook of FIGS. 39-41 in an implantation procedure as described below with reference to FIG. 29.
Figure 43:
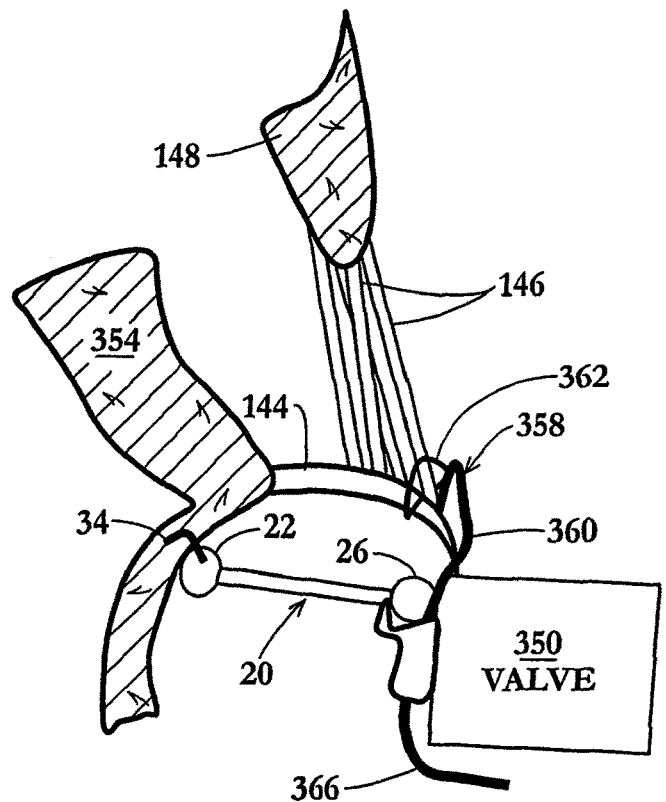
FIG. 43 is a diagram similar to FIG. 42, showing a fastener or locking element crimped to a tether or tension member of the grappling hook of FIGS. 39-42.
Figure 44:
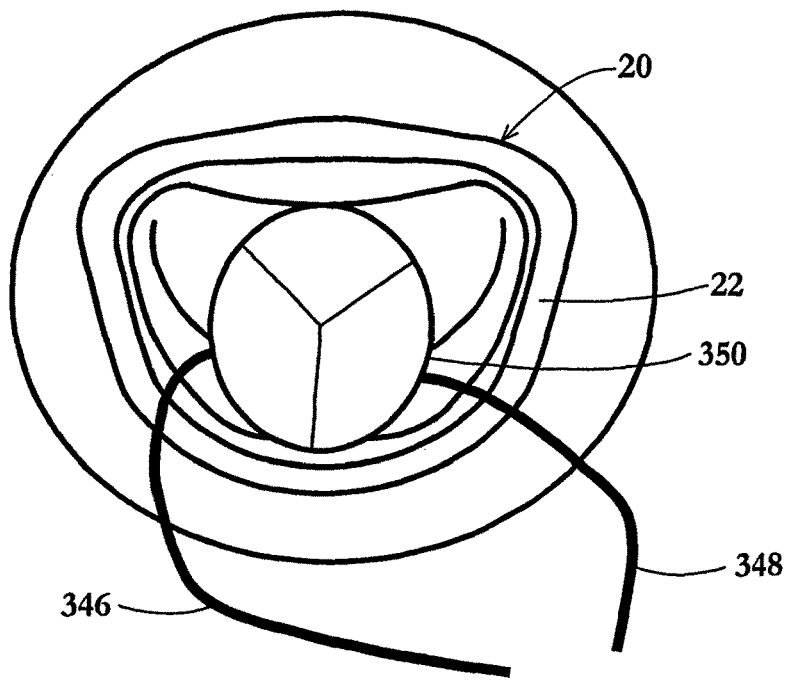
FIG. 44 is a view from the left atrium towards the mitral valve, showing an implantable scaffold in accordance with the invention fixed in position over a mitral valve and further showing two flexible tension members or tethers extending between the scaffold and a prosthetic valve inserted into the scaffold.

FIG. 42 shows grappling hook device 358 deployed so that barbs 364 at the ends of prongs or fingers 262 engage the edges of mitral valve leaflet 144. Grappling hook 359 engages leaflet 144 and retracts it to orifice or neoannulus 28 (se FIG. 2). Whereas the method of FIGS. 22-27, 37 and 38 transmits papillary forces by enveloping cords 146, the use of grappling hook device 358 pulls on the leaflets 144, which in turn, capture the cords 146. The mechanism of incorporation of the tension member or tether 366 into the combined scaffold 20 and valve 350 is identical to that described above with reference to FIGS. 22-27, 37 and 38, except there is only one tension member 366 per hook device 358, as opposed to the two strands or tether segments 346 and 348 associated with noose 352. As depicted in FIG. 43, a fastener 368 is advanced over tension member 366 of each hook device 358 deployed and the tension adjusted, then fixed. Tension member 366 is severed at fastener 368 with an end-cutting device (not shown). Fasteners 356 and 368 may be crimped to ensure a tight locking engagement with strands or tether segments 346, 348 or tether 366, respectively.

Figure 45:
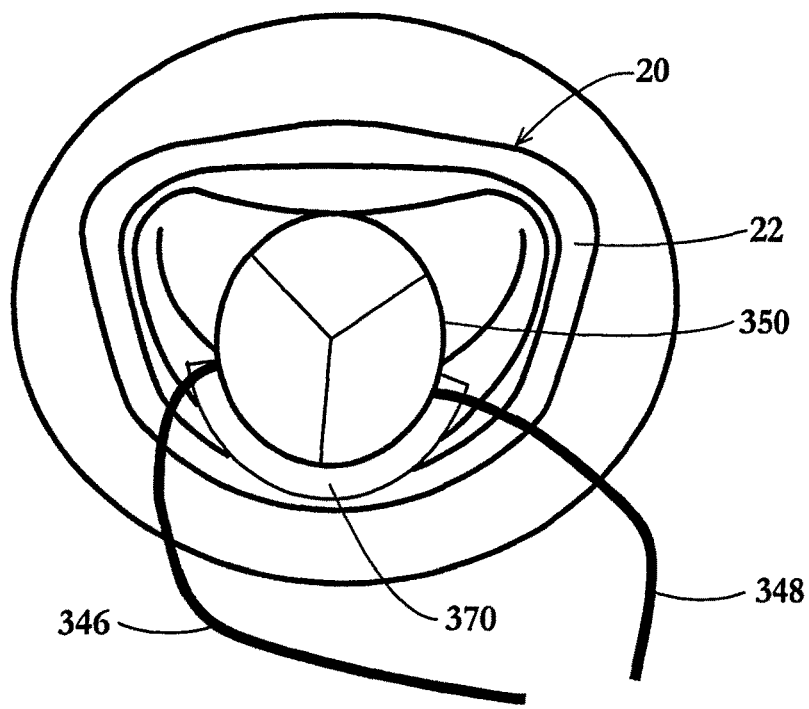
FIG. 45 is a view similar to FIG. 44, showing a spacer extending between the two tension members or tethers.
Figure 46:
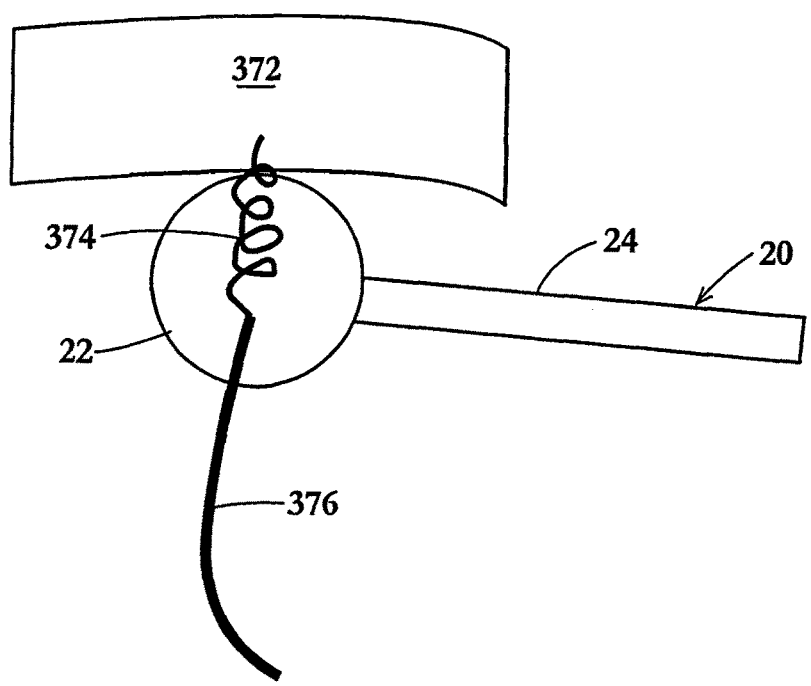
FIG. 46 is a schematic partial side elevational view of a valve-receiving scaffold in accordance with the invention and a means of attaching the scaffold to a heart wall.

As an alternative to fastener 356 of FIG. 38, FIG. 45 depicts a spacer member 370 that separates and connects strands or tether segments 346 and 348 associated with noose 352. Spacer member 370 is arc shaped, to fit snugly around cylindrically shaped valve 350 over a portion of inner margin or rim element 26. Strands or tether segments 346 and 348 are disposed with one toward one end of leaflet 144 and the other toward an opposite end. The use of spacer member 370 has the benefit of not foreshortening the leaflet 144.

Figure 48:
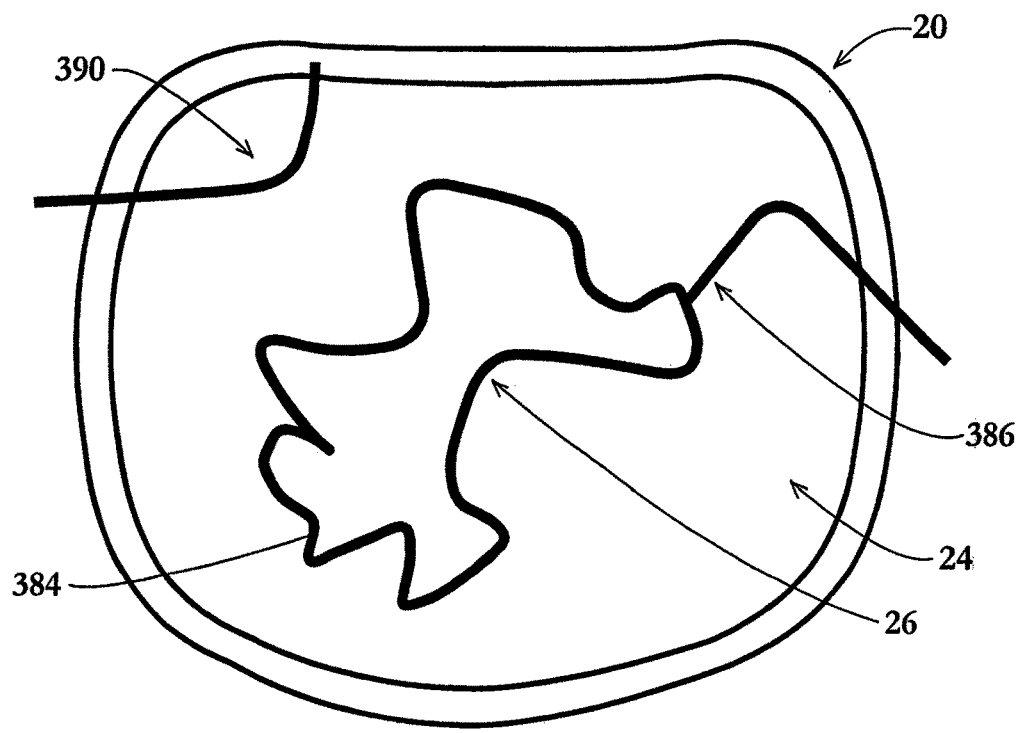
FIG. 48 is a front elevational view of a scaffold or valve-support implant in accordance with the invention, showing the implant in a partially collapsed configuration.

As illustrated in FIG. 48, outer margin or rim element 22 of scaffold 20 may be attached to the heart wall 372 by means of a helical coil element or cork screw 374 that advances into the heart wall upon a twisting of a positioning line 376 that is removably connected to a rear end of the coil or cork screw element.

Figure 47:
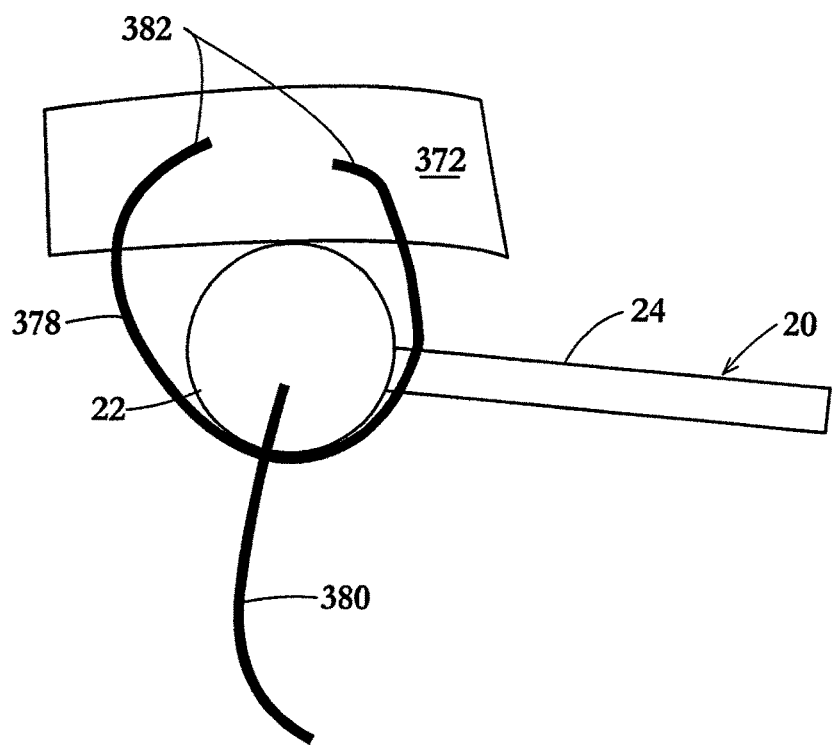
FIG. 47 is a view similar to FIG. 46, showing an alternative means of attaching the scaffold to a heart wall.

As shown in FIG. 47, outer margin or rim element 22 of scaffold 20 may be attached to the heart wall 372 by means of a staple 378 that is advanced over a positioning line or wire 380 and around margin or rim element 22 so that leg ends 382 of the staple are inserted into the heart wall. Staple 378 is then pinched, for instance, by a tubular member (not shown) inserted over positioning line or wire 380 and over a rear end of the staple, As depicted in FIG. 48, inner margin or rim element 26 of scaffold 20 may take the form of an annular tubular member with an enclosed lumen (like a non-distensible inner-tube). This annular tubular member 26 is inserted in a collapsed configuration via the delivery catheter (or otherwise in an open heart procedure). After ejection of the scaffold 20 from the distal end of the delivery catheter, the annular tubular member is expanded from a collapsed configuration 384 to a donut (toroidal) shape as in FIG. 2 et seq. by infusion of a liquid through a tube 386 communicating with the lumen of the tubular outer margin or rim element 22. The tubular member is inflatable but not expandable (i.e., is made of inelastic film material), so that valve 42 may be subsequently expanded into orifice or neo-annulus opening 28. In one iteration or embodiment of this approach, if a particular expanded configuration is found to be satisfactory, the inflation fluid could be replaced with another fluid via tube 386 or another tube (not shown) that would congeal into a solid or semi-solid, either by drainage and replacement with a different liquid, or addition of a second liquid, which, when mixed, caused the composite liquid to harden in the lumen and become solid or semi-solid.

Figure 49:
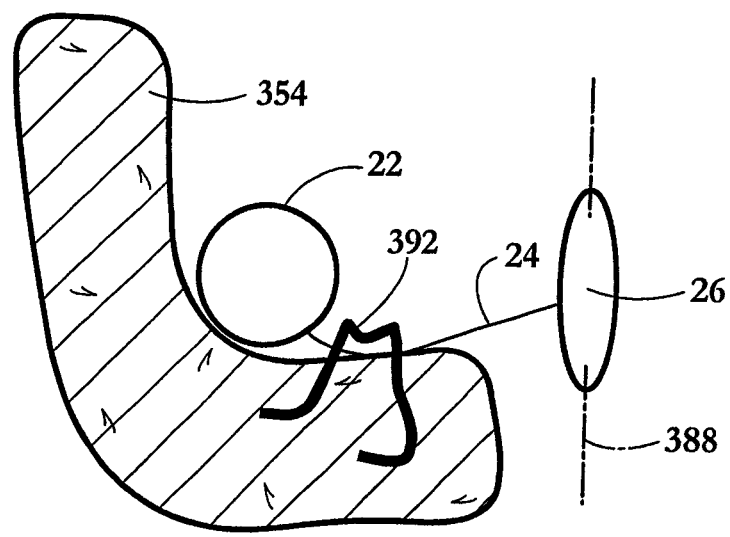
FIG. 49 is a partial cross-sectional view of a heart wall and a partial side elevational view of an embodiment of a valve-support scaffold in accordance with the invention, showing an alternative method of attachment of the latter to the heart wall, pursuant to the invention.

The cross-section of the inflatable lumen described above may be circular, or possibly oval with a long axis 388 (FIG. 49) oriented perpendicularly to membranous portion 24 of scaffold 20, thus providing a more cylindrical configuration to the neo-annulus.

Additionally or alternatively, outer margin or rim element 22 of scaffold 20 may take the form of an inflatable tubular member with an annular lumen inflatable by virtue of a removable tube 390 (FIG. 48), as described above for the inner margin or neo-annulus rim element 26. In this instance, the material of the tubular member may be rigid, but more likely semi-soft, allowing a tight fit with the heart wall. In this iteration, it may be necessary to fix the outer margin 26 to the heart wall indirectly by through and through staples, hooks, or barbs 392 (FIG. 49) at the adjacent edge of the membrane 24, rather than directly through the margin 26.

Alternatively, the lumen of the margin may contain a substance which is hydrophilic, such that it expands automatically when in contact with serum/blood/plasma. This may apply also to the neo-annulus.

Figure 50:
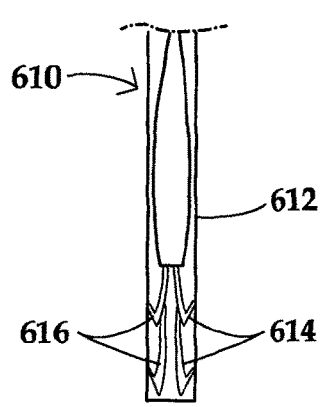
FIG. 50 is a schematic longitudinal cross-sectional view of a delivery catheter containing an implantable device in accordance with the present invention, in a collapsed, low profile configuration to facilitate minimally invasive access.
Figure 51:
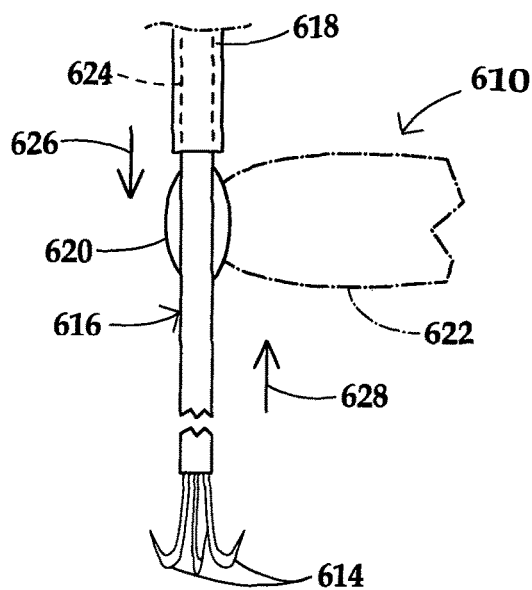
FIG. 51 is a schematic side elevational view of a tubular tether surrounding a proximal portion of an elongate tension member or tensile coupling element provided at a free or distal end with an entrainment element in the form of a grappling hook.

As illustrated in FIG. 50, a delivery system for an implantable valve support device 610 comprises a delivery catheter 612, which contains the implantable device in a collapsed low profile configuration to facilitate minimally invasive access. FIG. 50 shows a plurality of valve-leaflet entrainment or capture elements 614 in the form of hooks, e.g., grappling hooks, or barbs. As illustrated in FIG. 51, each leaflet entrainment element 614 is carried at the free or distal end of an elongate flexible tensile coupling element 616. Each tensile coupling element 616 extends through a respective tubular positioning tether 618 that is removably attached at its distal end to a locking element 620 in turn connected to a neo-annulus or scaffold 622 that receives and supports a prosthetic or bio-prosthetic valve. Positioning tether 618 surrounds a proximal portion 624 of tensile or tensile coupling member 616. As discussed in detail hereinafter, in a prosthetic-valve implantation procedure, neo-annulus or scaffold 622 is moved towards a native valve by exerting a distally directed force 626 on tubular positioning tether 618 while exerting a proximally directed force 628 on tensile coupling element 616.

Figure 52:
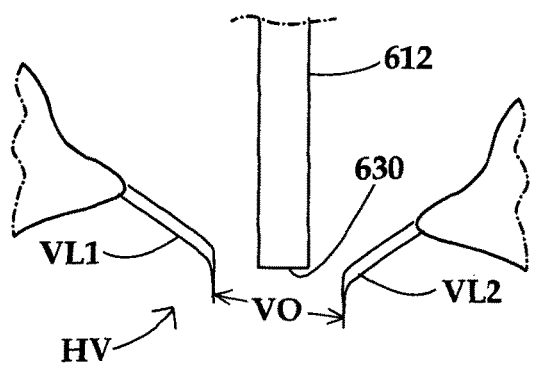
FIG. 52 is a schematic side elevational view of the delivery catheter of FIG. 50 as advanced through a vascular system of a subject to a native heart valve.
Figure 53:
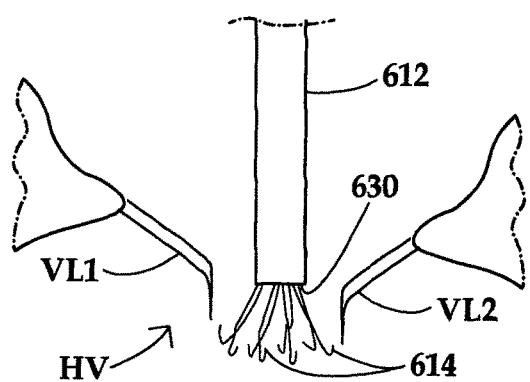
FIG. 53 is a schematic side elevational view similar to FIG. 52, showing a multiplicity of hook-like entrainment or capture elements on tensile coupling members as shown in FIG. 51, advanced inside the native valve of FIG. 52 into a heart chamber or blood vessel.
Figure 54:
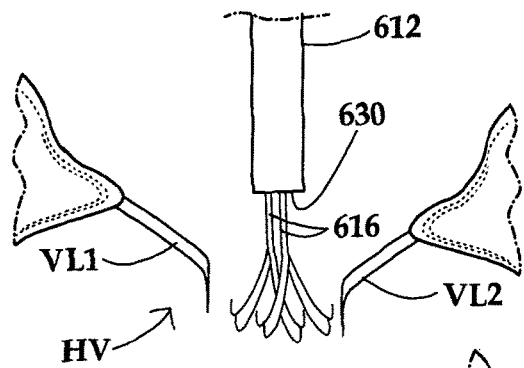
FIG. 54 is a schematic side elevational view similar to FIGS. 52 and 53, showing the delivery catheter retracted back across the native heart valve with the hooks and tension members remaining in place.

FIG. 52 shows delivery catheter 612 as advanced through a vascular system of a subject to a native heart valve HV having a pair of valve leaflets VL1 and VL2. A distal tip 630 of catheter 612 is located in or proximate to an orifice VO between valve leaflets VL1 and VL2. At that juncture of a valve implantation procedure, hook-like entrainment or capture elements 614 and distal end portions of tensile coupling elements 16 are ejected from the distal tip 630 of delivery catheter 612, as depicted in FIG. 53. Then, as shown in FIG. 54, delivery catheter 612 is retracted back across the native heart valve HV with the hooks 614 and tension members 616 remaining in place.

Figure 55:
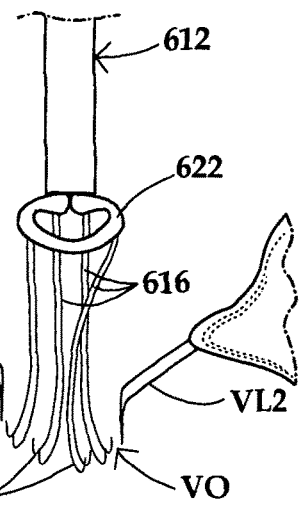
FIG. 55 is a schematic perspective or side elevational view similar to FIGS. 52-54, showing partial extrusion or ejection of a neo-annulus scaffold or valve support member from the delivery catheter, while hooks and tension elements remain in place adjacent to the native valve leaflets.
Figure 56:
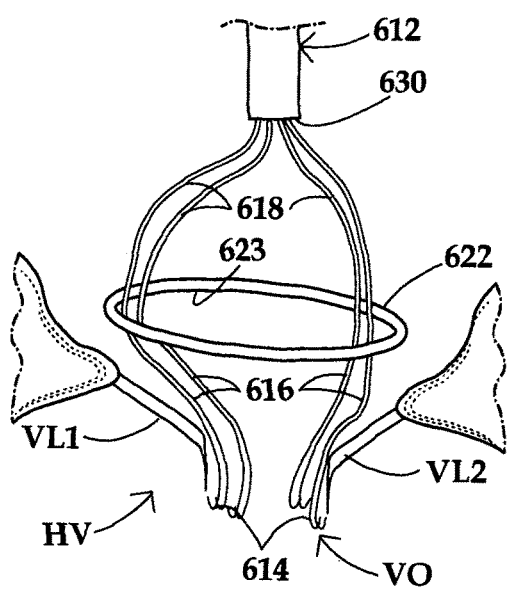
FIG. 56 is a schematic perspective view similar to FIGS. 52-55, showing the scaffold expanded in a heart chamber or blood vessel, ready for manipulation or positioning by a series of tethers like the tether of FIG. 51.

FIG. 55 shows a subsequent step of a valve implantation procedure, in particular a partial extrusion or ejection of neo-annulus or scaffold 622 from delivery catheter 612. Hooks 614 and tensile coupling elements 616 remain in place adjacent to the native valve leaflets VL1 and VL2. FIG. 56 shows neo-annulus or scaffold 622 fully ejected from catheter 612 and expanded in the heart chamber or blood vessel. Multiple positioning tethers 618 extend to respective locks 620 (FIG. 51) and support the expanded neo-annulus or scaffold 622 during the implantation procedure. Tensile coupling elements 616 extend from respective positioning tethers 618 at the periphery of neo-annulus or scaffold 622. Leaflet-entrainment hooks 614 dangle loosely within or beyond the native valve orifice VO.

As shown in FIG. 56, the expanded neo-annulus or scaffold 622 takes the form of a ring which defines a valve-receiving circular orifice 623. Neo-annulus scaffold 622 is preferably flexible for at least a given time after ejection from delivery catheter 612 so as to allow manipulation and reconfiguration after delivery, but also relatively inelastic so that a radially expanded valve 634 (FIG. 58 et seq.) does not distort it. Scaffold 622 may be constructed of a braided or monofilament metal or other appropriate synthetic or naturally occurring material with the appropriate physical characteristics. Alternatively, scaffold 622 made be made of nitinol optionally with a temperature-induced memory by which the scaffold assumes a substantially fixed ring shape after ejection from the delivery or deployment catheter 612.

Figure 57:
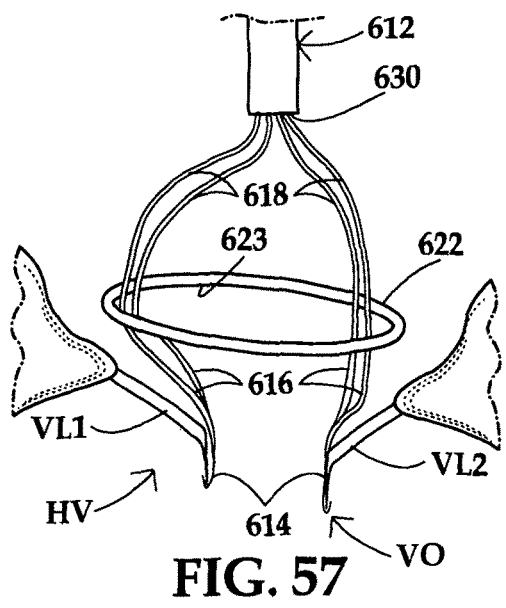
FIG. 57 is a schematic perspective view similar to FIGS. 52-56 showing initial purchase or entrainment of the native heart valve leaflets by the hooks of the tensile coupling elements, which condition of initial entrainment still allows normal or near normal valve function.
Figure 58:
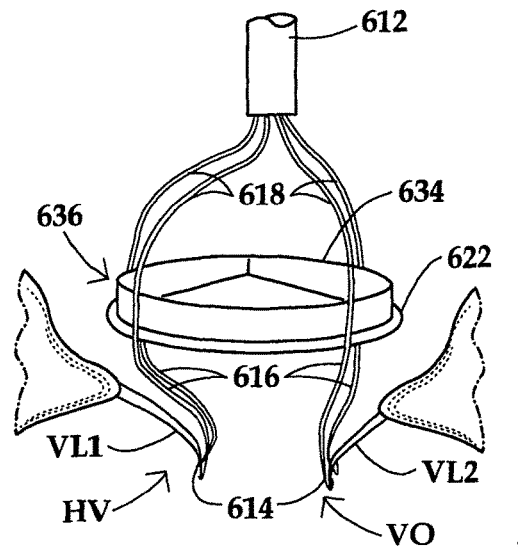
FIG. 58 is a schematic perspective view similar to FIGS. 52-57, showing a prosthetic or bio-prosthetic replacement valve deployed into an orifice of the scaffold or valve support member.

After the ejection of neo-annulus or scaffold 622, tensile coupling elements 616 are manipulated from outside the patient to bring hooks 614 into engagement with the edges (not separately designated) of valve leaflets VL1 and VL2, as depicted in FIG. 57. This initial entrainment allows normal or near normal valve function. Subsequently, as shown in FIG. 58, prosthetic or bio-prosthetic valve 634 is seated in neo-annulus orifice 623 and attached to scaffold 622 to form a neo-annulus/replacement valve complex 636.

Figure 59:
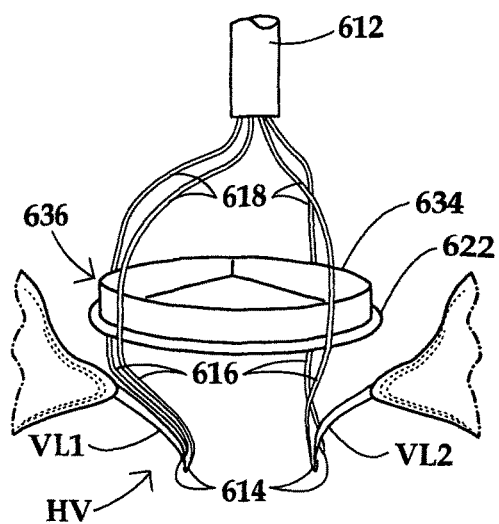
FIG. 59 is a schematic perspective view similar to FIGS. 52-58, showing a neo-annulus/replacement valve complex advanced towards the orifice of the native valve by exertion of a retractive or proximally directed force on the tensile coupling elements and a simultaneous exertion of a pushing or distally directed force on the tubular tethers.

FIG. 59 depicts scaffold 622 with the mounted valve 634 moved closer to native valve HV. This change in position of neo-annulus/replacement valve complex 636 is effectuated by pushing positioning tethers 618 in a distal direction, as indicated by force arrow 626 in FIG. 51, while simultaneously pulling tensile coupling elements 616 in a proximal direction, as indicated by force arrow 628 in FIG. 51.

Figure 60:
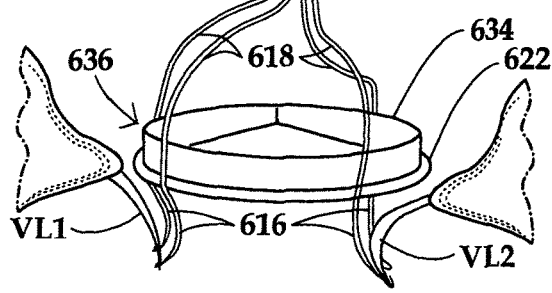
FIG. 60 is a schematic perspective view similar to FIG. 59, showing further advancement of the neo-annulus/replacement valve complex towards the orifice of the native valve.
Figure 61:
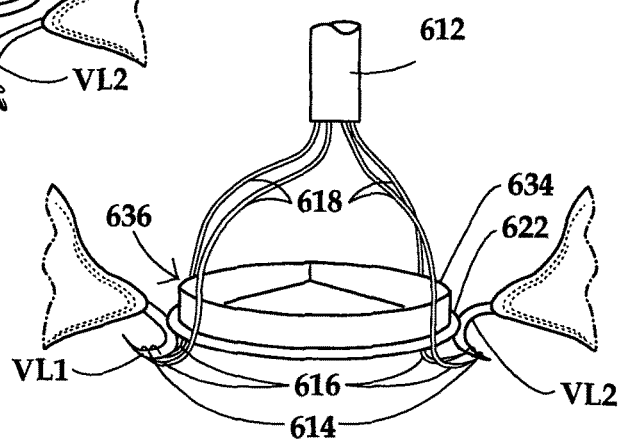
FIG. 61 is a schematic perspective view similar to FIGS. 52-60, showing a seating of the neo-annulus/replacement valve complex into the orifice of the native valve and full retraction of the tension or coupling members.

FIG. 60 is a schematic perspective view similar to FIG. 59, showing further advancement of neo-annulus/replacement valve complex 636 towards the orifice VO of the native valve HV. After a final advancement of neo-annulus/replacement valve complex 636, depicted in FIG. 61, the neo-annulus/replacement valve complex is seated into the orifice VO the native valve HV and tensile coupling elements are fully retracted to curl the lips or edges of valve leaflets VL1 and VL2.

Subsequently, as depicted in FIG. 62, positioning tethers 618 are removed or detached from the implanted neo-annulus/replacement valve complex 636 and tensile coupling elements 616 are severed at locks 620 (FIG. 51). In the completed implantation, neo-annulus/replacement valve complex 636 is held by tensile coupling elements 616 and entrainment hooks 614 in a fluid sealing engagement with valve leaflets VL1 and VL2. This mode of implantation ensures that the valve securing forces exerted by the chordae tendineae.

FIGS. 53-55 depict steps in a modified implantation procedure wherein neo-annulus or scaffold 622 is provided at spaced intervals around its circumference with a plurality of flexible elongate tensile suspension elements 638 that are attachable at their free ends 640 to a wall CVW of the heart or a blood vessel (collectively, "cardio-vascular wall"). Suspension members 638 are manipulated via respective deployment tethers 642 that extend from delivery catheter 612 or a separate deployment catheter (not illustrated) and detachably attach to the suspension members at free ends 640 thereof. Typically, free ends 640 of suspension members 638 are coupled to wall CVW after the ejection of scaffold 622 from catheter 612 but before the moving of neo-annulus/replacement valve complex 636 into engagement with valve leaflets VL1 and VL2, and preferably before the seating of prosthetic valve 634 in orifice 623 of neo-annulus or scaffold 622.

Scaffold 622 is optionally provided with suspension elements 638, which are extendible radially to attach to the heart or blood vessel wall CVW near the native valve HV for which replacement is intended. Suspension elements 638 appear like spider legs, or as ring-topped, flattened tripod (in an instance wherein three such elements are used). Suspension elements 638 may be constructed of a spring-like material and are curved to allow for fixation to heart or blood vessel wall CVW of variable contour and also allow for excursion of the neo-annulus scaffold 622 toward the valve HV as necessary.

FIG. 64 shows neo-annulus scaffold 622 supported by the deployed elongate suspension elements 638 of FIG. 63, and with deployment tethers 642 removed. Scaffold 622 is ready for capture of valve leaflets LV1 and LV2 by entrainment hooks 614 and for deployment of prosthetic valve 634 (not shown), followed by advancement of the complex 636 into the native valve orifice VO.

FIG. 65 depicts a detail of an alternative, auto-fixation, method of attachment of a suspension line 638 to cardio-vascular wall CVW. Suspension line 638 is provided at a free end with a barb 644 that anchors the suspension line to the cardiovascular wall CVW. Deployment tether 642 is removably coupled to suspension line 638 to permit the forceful insertion of barb 644 into the tissues of wall CVW and the subsequent detachment of tether 642 from suspension line 638.

Figure 66:
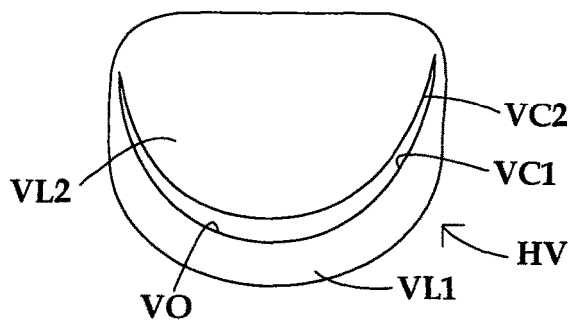
FIG. 66 is a schematic plan view of a native mitral valve, showing valve commissures.
Figure 67:
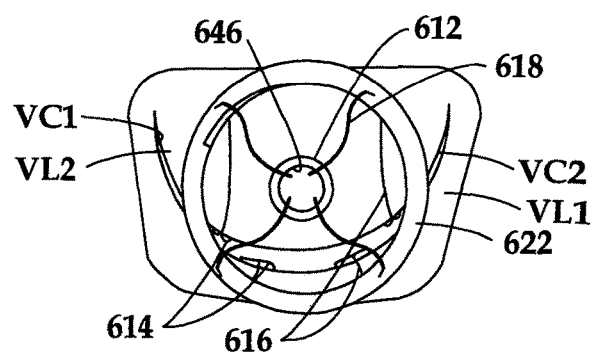
FIG. 67 is a schematic plan view similar to FIG. 66, showing a ring-shaped neo-annulus scaffold in place over the native mitral valve. Hooks for valve leaflet capture and the associated tensile coupling elements are visible through the orifice of the neo-annulus scaffold while the positioning tethers of FIG. 51 extend between the delivery catheter and the neo-annulus, the lumen of the catheter being shown in cross-section.
Figure 68:
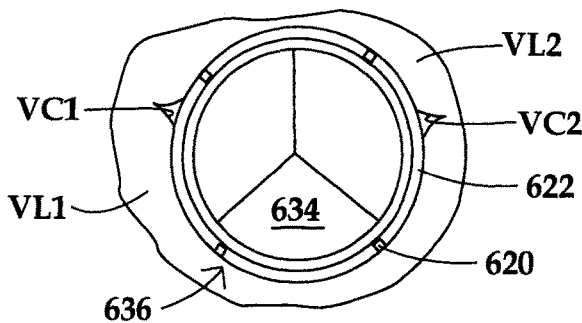
FIG. 68 is a schematic plan view similar to FIGS. 66 and 67, depicting the neo-annulus scaffold in position abutting the valve leaflets and with a prosthetic or bio-prosthetic replacement valve deployed, further depicting commissures leaving gaps in the seal around the neo-annulus, resulting in a perivalvular leak.

FIG. 66 is a schematic plan view of native mitral valve HV, showing valve commissure gaps VC1 and VC2 between valve leaflets VL1 and VL2. FIG. 67 illustrates ring-shaped neo-annulus scaffold 622 in place over the native mitral valve HV. Hooks 614 for capture of valve leaflets LV1 and LV2 and the associated tensile coupling elements 616 are visible through the orifice 623 of neo-annulus scaffold 622 while the positioning tethers 618 of FIG. 100 extend from delivery catheter 612 to the neo-annulus scaffold, the lumen 646 of the catheter being visible in cross-section. As shown in FIGS. 19 and 20, with neo-annulus scaffold 622 in position abutting the valve leaflets LV1 and LV2 and prosthetic or bio-prosthetic replacement valve 634 deployed, commissure gaps VC1 and VC2 are open at the periphery of the neo-annulus, resulting in a perivalvular leak. Two approaches for closing gaps VC1 and VC2 are discussed below.

Figure 69:
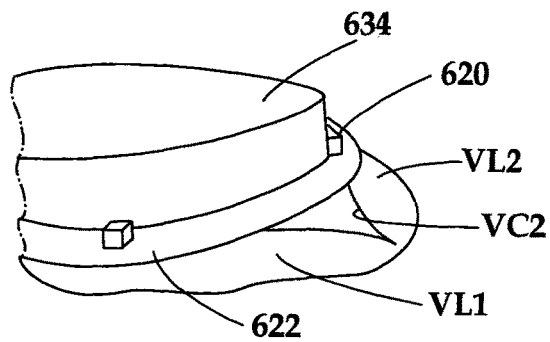
FIG. 69 is a partial schematic perspective view of the neo-annulus scaffold and replacement valve of FIG. 68 in position abutting the native-valve leaflets, illustrating a gap at a commissure, and also schematically illustrating locks on the tensile coupling elements holding them in place relative to the neo-annulus.

FIG. 69 also schematically illustrates locks 620 cooperating with the tensile coupling elements 616 to hold them in place relative to neo-annulus or scaffold 622.

FIG. 70 is a series of three side elevational views of a tissue approximation clip or anchor 650 in three configurations relative to apposed valve leaflets LV1 and LV2. Clip or anchor 650 is initially inserted in a distal direction 652 through a commissure gap VC1 or VC2. Then clip or anchor 650 us retracted in a proximal direction 654, causing apposition of the leaflets and a closing of the gap. Finally prongs 656 of clip or anchor 650 are bent downwardly at 658 for permanent placement.

FIG. 71 is a partial schematic perspective view similar to FIG. 69, showing anchor-shaped clip 650 deployed for leaflet-edge approximation. Typically, one or more clips or anchors 650 are deployed after the locking of neo-annulus/replacement valve complex 636 to the valve leaflets LV1 and LV2. However, one or more clips or anchors 650 may alternatively deployed prior to the engagement or locking of the neo-annulus/replacement valve complex 636 to the valve leaflets.

Figure 74:
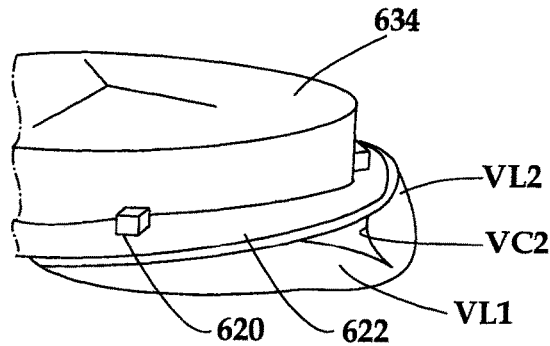
FIG. 74 is a partial schematic perspective view similar to FIG. 71, showing a bladder-like sealing component disposed around a periphery of the neo-annulus scaffold in a deflated insertion configuration.
Figure 75:
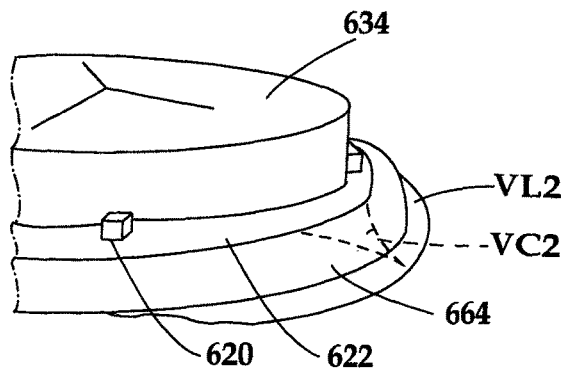
FIG. 75 is a partial schematic perspective view similar to FIG. 74, showing the bladder-like sealing component in an expanded sealing configuration, covering or closing a gap between valve leaflets.

In an alternative method for closing commisure gaps VC1 and VC2, neo-annulus or scaffold 622 is provided along an other periphery with a collapsed bladder-like component 660, as depicted in FIG. 72A. An inflation tube or port member 662 extends to collapsed bladder 660 for feeding thereto a fluid such as carbon dioxide, saline solution, a liquid polymer, a polymerizable monomer composition, etc., thereby expanding the collapsed bladder or balloon 660 to an enlarged configuration 664 shown in FIG. 72B. The expanded bladder configuration 664 is also depicted in FIGS. 73 and 75, while FIG. 74 shows the collapsed insertion configuration of balloon or bladder 660. As depicted in FIG. 75, expanded bladder configuration 664 covers and closes commisure gaps VC1 and VC2. Typically, as illustrated in FIGS. 74 and 75, the bladder 660, 664 is an annular member extending circumferentially about the outer periphery of neo-annulus or scaffold 622.

Figure 76:
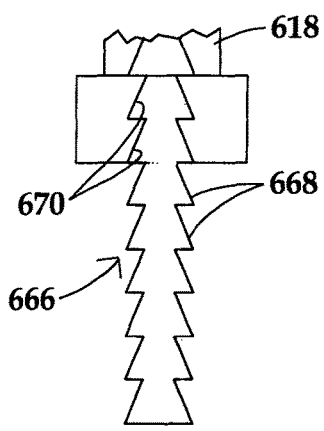
FIG. 76 is a schematic side elevational view of ratchet-type locking components provided on the neo-annulus scaffold and the distal end of a tensile coupling element to allow only one-way excursion of the tensile coupling element and its appended valve-capture or entrainment element (not shown), the tether being pushed in the distal direction and the tensile coupling element being pulled in the proximal direction to clamp the neo-annulus scaffold and attached replacement valve to the valve leaflets.

FIG. 76 is a schematic side elevational view of an incremental movement device in the form of ratchet-type locking components 620 and 666 provided on the neo-annulus scaffold 622 and distal ends of tensile coupling elements 616 to allow only one-way excursion of the tensile coupling elements and the appended valve-capture or entrainment elements 614 (see other figures). Locking component 666 is a series of tapered teeth 668 each having, for example, a frusto-conical form (FIG. 51). In that case, locking component 620 is a block provided internally with one or more tapered passageway sections 670 that are geometrically congruent with teeth 668. Tensile element 616 may be pulled in the proximal direction 628 while positioning tether 618 is pushed in the distal direction 626, which moves locking component 620, and accordingly scaffold 622 and neo-annulus/replacement valve complex 636, in the distal direction relative to tensile coupling element 616. However, the shapes of teeth 666 and passageway sections 670 prevent an opposite relative motion of tensile coupling element 616 and neo-annulus/replacement valve complex 636. Ratchet-type locking components 620 and 666 thus enable a clamping of the neo-annulus scaffold 622 and attached replacement valve 634 to the valve leaflets LV1 and LV2.

Figure 77A:
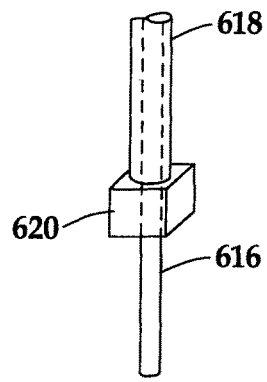
FIGS. 77A and 77B are a schematic perspective view and a schematic longitudinal cross-sectional view, respectively, showing another embodiment of a ratchet mechanism.
Figure 77B:
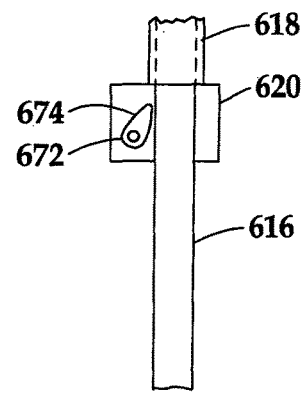

FIGS. 77A and 77B show another embodiment of a ratchet mechanism wherein lock 620 is provided internally with a pivotably mounted latch or détente 672 having a sharp end 674 pointed in a proximal direction, towards tether 618. Latch or détente 672 permits motion of tensile coupling element 616 in the proximal direction 28, that is, towards tether 618 but prevents the opposite motion.

Figure 78:
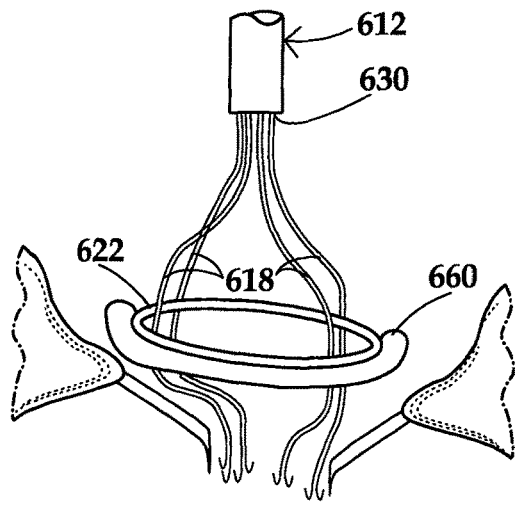
FIG. 78 is a schematic perspective view of a neo-annulus scaffold with collapsed perimetral closure bladder, tensile coupling elements with distal hooks entrained to the ends or edges of native valve leaflets, and tubular tethers extending from the distal end of a delivery catheter and holding the scaffold in position for installation.

FIG. 78 depicts neo-annulus scaffold 622 with collapsed perimetral closure bladder 660, tensile coupling elements 616 with distal hooks 614 entrained to the ends or edges of native valve leaflets LV1 and LV2, and tubular tethers 618 extending from the distal end of a delivery catheter 612 and holding the scaffold in position for installation.

Figure 79:
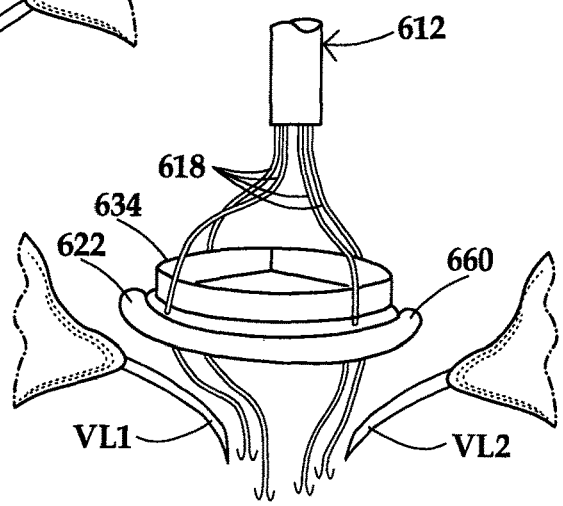
FIG. 79 is a schematic perspective view similar to FIG. 78, showing a replacement valve mounted to the neo-annulus scaffold.

FIG. 79 is a schematic perspective view similar to FIG. 78, showing replacement valve 634 mounted to the neo-annulus scaffold 622.

Figure 80:
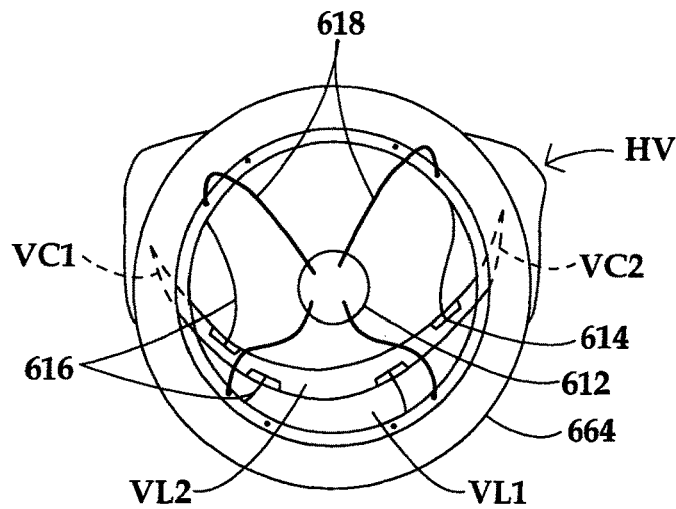
FIG. 80 is a schematic plan view of the neo-annulus scaffold of FIGS. 78 and 79 in place above the native mitral valve with native valve capture and the "sewing ring" or closure bladder inflated, but with the replacement valve omitted.

FIG. 80 shows neo-annulus scaffold 622 in place above the native mitral valve HV with native valve leaflets LV1 and LV2 captured and the "sewing ring" or closure bladder 660 in its inflated configuration 664 but with the replacement valve 634 omitted for clarity.

Suspension elements 638, as well as the neo-annulus or scaffold 622, may be covered or coated with a substance to enhance tissue ingrowth, prevent clot or blood adhesion, may be drug eluting, heparin or other substance bonding, or otherwise be constructed of a material that enhances tissue ingrowth, prevent clot or blood adhesion.

The implantation device and associated method described above are designed in such a way as to enhance delivery by construction of the scaffold so that valve-capture elements 614, suspension elements 638, if used, peri-valvular inflatable or gap-closure devices 650 and 660, if used, are incorporated into the neo-annulus 622 such that serial emergence from the delivery system 612 simplifies placement of the entire system. Combining valve deployment with capture of the native valve leaflets LV1 and LV2 may create a minimal risk of valvular stenosis or insufficiency. Further, the design of the device transfers all cardiac forces onto the native valve HV. In the case of AV valves, the scaffold or valve support device 622 is at least indirectly secured to chordae tendineae, and therefore, the papillary muscles of the heart. Therefore such a device can distribute forces to the prosthetic valve 634 similar to those typical of the normal, native valve.

Figure 81:
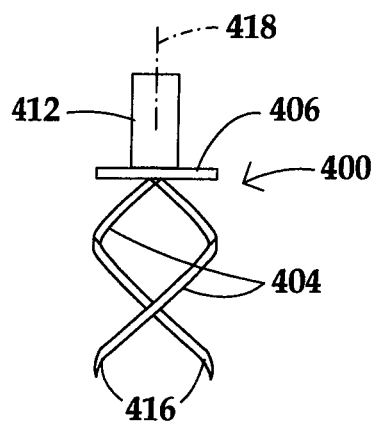
FIG. 81 is a schematic side elevational view of a helical fastener with a truncated sleeve, which is slidably disposed over a scaffold-positioning tether, in accordance with the present invention.

FIG. 81 et seq. below describe alternative methods and devices for implanting a prosthetic or bio-prosthetic valve in a heart chamber or blood vessel. Fastener or fixation devices 400, 428, and 436 described hereinafter are useful for attaching suspension elements 438 to cardio-vascular wall CVW.

Figure 82:
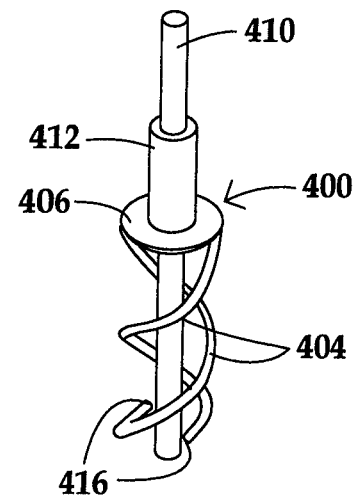
FIG. 82 is a schematic perspective or isometric view of a helical fastener similar to that of FIG. 81 sliding over a tether.
Figure 83:
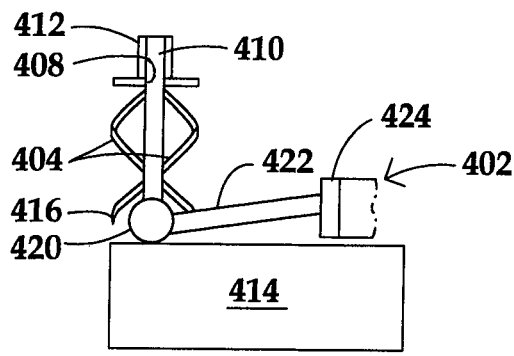
FIG. 83 is a schematic partial cross-sectional view of the helical fastener of FIG. 81 juxtaposed to a heart wall and a margin of a valve-support scaffold.

As illustrated in FIG. 81, a fastener or fixation device 400 for coupling a valve-supporting scaffold 402 (FIGS. 87 and 88) comprises a pair of helical prongs or legs 404 each attached at one end to a cap or head 406 in the form of a disk. As illustrated in FIG. 83, disk 406 is provided with a hole 408, which is traversed by a scaffold-positioning tether 410 (FIGS. 82, 83, 85) so that the fastener or fixation device 400 is slidable along the tether. During a deployment operation, a pusher member 412 in the form of an elongate sleeve or tube (only a distal end portion thereof shown in the figures) engages cap or head 406 to press fastener 400 to a distal end of tether 410 and into organic tissues, specifically a heart chamber or vessel wall 414. Once distal tips 416 of prongs or legs 404 enter the heart chamber or vessel wall 414, further distal motion of pusher member 412 induces fastener to turn about its longitudinal axis 418 (FIG. 81), twisting the fastener deeper into the organic tissues. Prongs or legs 404 straddle an outer margin or outer rim element 420 (FIGS. 83-86) of scaffold 402, with one of the prongs or legs passing through a membrane 422 that extends between margin 420 and an inner rim element or neo-annulus 424 of the scaffold. Prong tips 416 enter the heart or vessel wall on the opposing sides of margin 420, and the prongs or legs 404 cooperate with the organic tissue in a camming motion to induce rotation of the fastener 400.

Figure 84:
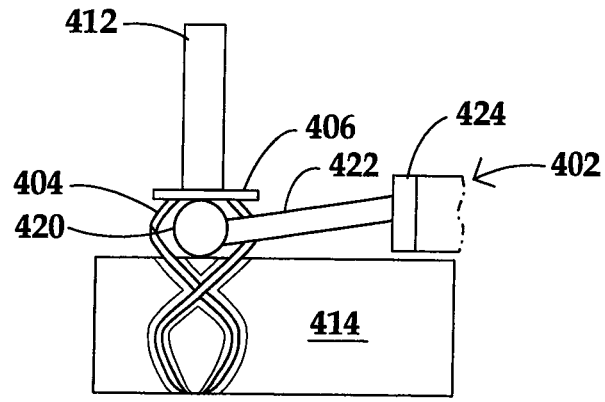
FIG. 84 is a schematic perspective view similar to FIG. 63, showing the neo-annulus scaffold supported by the deployed elongate suspension elements of FIG. 63, and with the deployment tethers of FIG. 63 removed, ready for valve capture and replacement valve deployment, followed by advancement of the complex into the native valve orifice.
Figure 85:
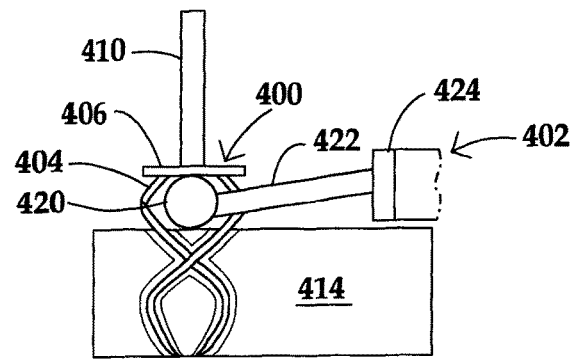
FIG. 85 is a schematic partial cross-sectional view similar to FIG. 84, showing the fastener partially embedded in the heart wall with the pusher sleeve or tube withdrawn, but the tether still attached to the scaffold margin.
Figure 86:
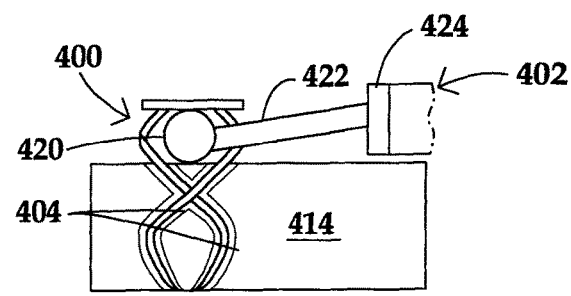
FIG. 86 is a schematic partial cross-sectional view similar to FIG. 84, showing the fastener partially embedded in the heart wall and holding the scaffold in place, but with the tether removed, this view representing the ultimate state of scaffold fixation.

Insertion of fastener 400 is complete when cap or head 406 comes into contact with margin 420, as shown in FIG. 84. Pusher member 412 is then withdrawn (FIG. 85). Tether 410 is also detached from scaffold 402 and withdrawn (FIG. 86). Pusher member 412 may be extracted from the heart or vessel and from the patient prior to the detachment and extraction of tether 410. Alternatively, tether 410 may be detached first (e.g., by a twisting of the tether), with a subsequent simultaneous extraction of the tether and pusher member 412.

Figure 87:
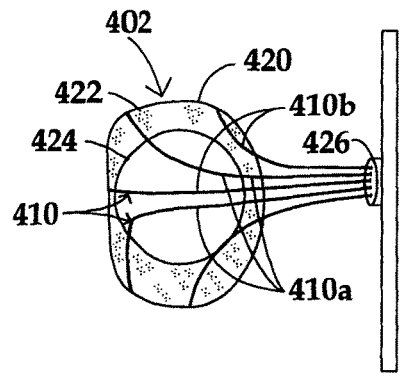
FIG. 87 a schematic perspective or isometric view of a valve-support scaffold in an expanded configuration and a plurality of positioning tethers.
Figure 88:
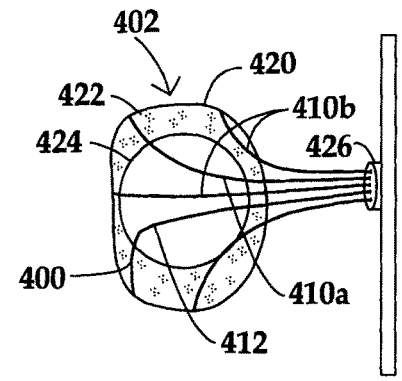
FIG. 88 is a view similar to FIG. 87, showing a pusher sleeve or tube advanced over a tether and in contact with a helical fastener at the margin of the valve-support scaffold, for deployment of the fastener into a heart or blood vessel wall.

FIG. 87 shows scaffold 402 after it has been ejected from a delivery catheter 426 and opened from a collapsed insertion configuration (not shown) to the illustrated expanded deployment configuration. A plurality of tethers 410, detachably linked at their distal ends to margin 420 of scaffold 402 at spaced locations therealong, includes three primary tethers 410a and optionally several secondary tethers 410b. Primary tethers 410a are manipulated to position margin 420 and concomitantly scaffold 402 into a desired position and orientation inside a target heart chamber or vessel. Fasteners 400 are initially deployed along the primary tethers 410a (see FIG. 88) to connect margin 420 to heart chamber or vessel wall 414 at three respective locations. Further fasteners 400 may be subsequently deployed along the secondary tethers 410b.

Figure 89:
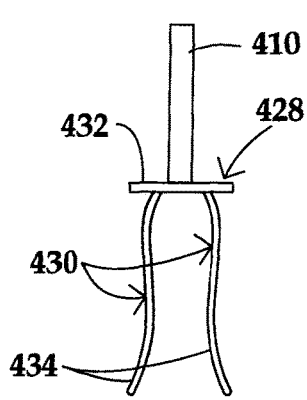
FIG. 89 is a schematic side elevational view of an alternative, two-pronged staple for fastening a margin of a valve-support scaffold to a heart or blood vessel wall.
Figure 90:
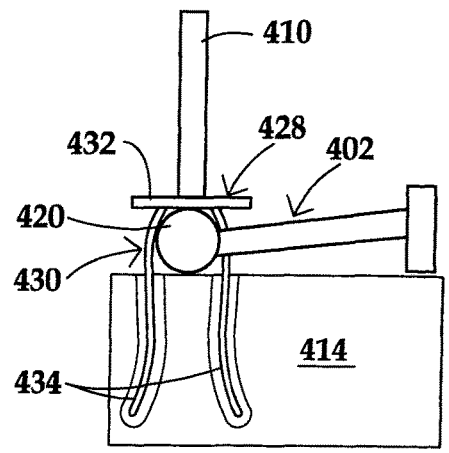
FIG. 90 is a schematic cross-sectional view of the staple of FIG. 89 with the prongs partially inserted into a heart or blood vessel wall over a margin or rim element of a valve-support scaffold or frame.
Figure 91:
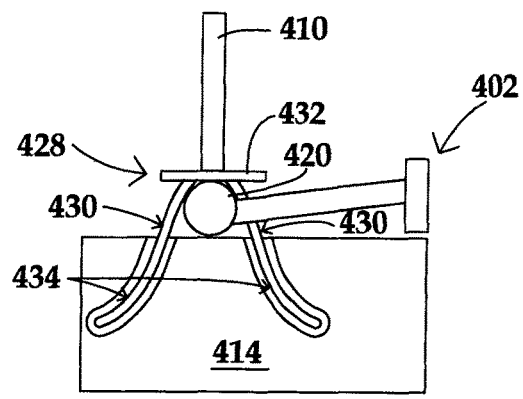
FIG. 91 is a schematic cross-sectional view similar to FIG. 90, showing the prons or legs of the staple in an angled-apart or expanded configuration to create fixation.

As depicted in FIGS. 89-91, an alternative fastener or margin fixation device 428 is a staple having two prongs or legs 430 each attached at one end to a cap or head 432 in the form of a perforated disk slidably traversed by tether 410. Prongs or legs 430 each exhibit a shallow S-shape with an outwardly turned tip 434, the two prongs being mirror images of one another. Tips 434 cause prongs or legs 430 to splay outwardly during an insertion operation, as shown in FIG. 91. This divergence or opening of the staple prongs 430 serves to anchor fasteners 428 in a heart chamber or vessel wall 414.

Figure 92:
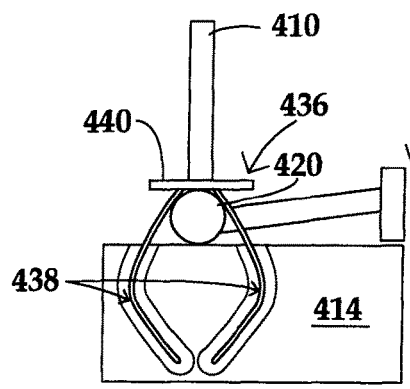
FIG. 92 is a schematic cross-sectional view of a second alternative staple configuration wherein the tips turn in to create fixation.
Figure 93:
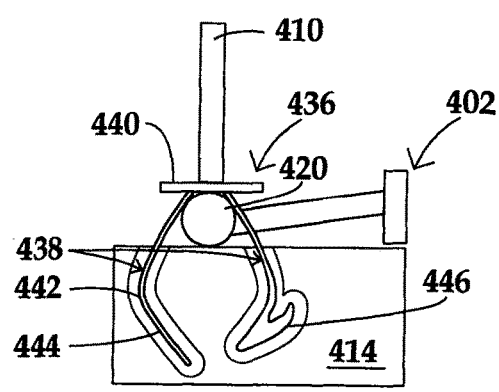
FIG. 93 is a schematic cross-sectional view similar to FIG. 92, shows a prong of the staple provided with a removal-prevention barb.

As illustrated in FIGS. 92 and 93, another alternative fastener or margin fixation device 436 is a staple having two prongs or legs 438 each attached at one end to a cap or head 440 again in the form of a perforated disk slidably traversed by tether 410. Prongs or legs 438 each have a slightly arcuate proximal portion 442 attached to cap or head 440 and an inwardly dog-legged distal end 444. Distal ends 444 cause prongs or legs 438 to crimp inwardly during an insertion operation. As shown in FIG. 93, one or both prongs 438 may carry a rearwardly oriented barb or hook 446 for providing enhanced resistance to removal of the fastener 436 from the heart or vessel wall 414.

Figure 94:
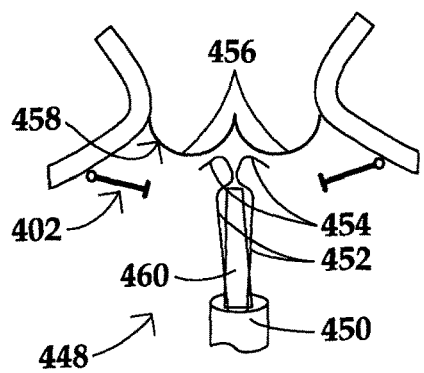
FIG. 94 is a schematic perspective or isometric view of a valve retrieval system, for capturing leaflets of a natural atrial valve and indirectly capturing the cords (not shown), showing the natural valve in a closed state.

FIG. 94 depicts a valve retrieval system 448 comprising an introducer catheter 450 and a plurality of tethers 452 deployed via the catheter and provided at their free ends with capture hooks or barbs 454 for entraining leaflets 456 of a natural atrial valve 458 and indirectly capturing the cords (not shown). Valve retrieval system 448 further includes a tether guide member 460, which maintains tethers 452 in a suitably arranged or distributed array. To that end, tether guide member may be provided with angularly spaced grooves or passageways for guiding the respective tethers 452. Valve retrieval system 448 is inserted into the patient after the installation of valve-supporting scaffold 402 and prior to the seating of a prosthetic valve 462 (FIGS. 101-103) in neo-annulus 424.

Figure 95:
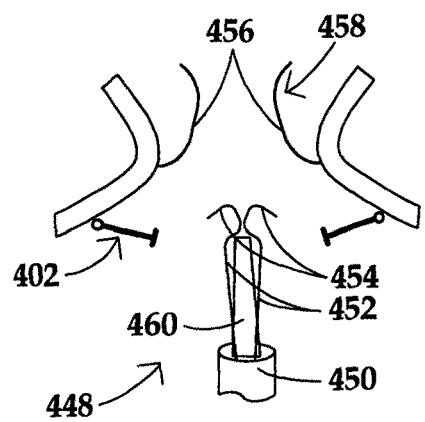
FIG. 95 is a schematic perspective or isometric view similar to FIG. 94, showing the valve in an opened state.
Figure 96:
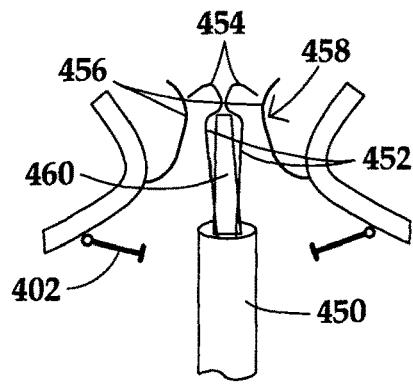
FIG. 96 is a schematic perspective or isometric view similar to FIGS. 94 and 95, showing the valve retrieval system advanced through the open valve.
Figure 97:
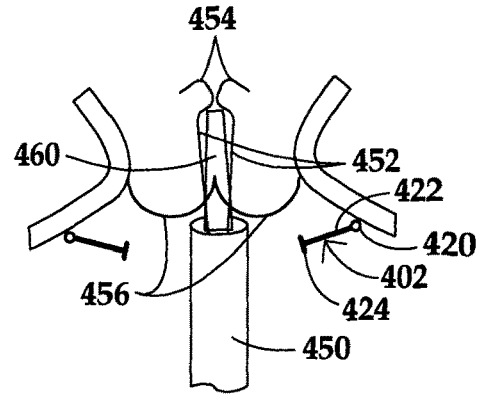
FIG. 97 is a schematic perspective or isometric view similar to FIG. 96, showing the valve closed around the valve retrieval system.
Figure 98:
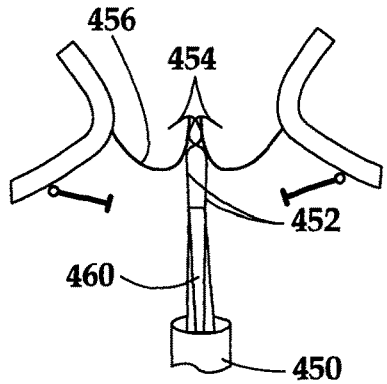
FIG. 98 is a schematic perspective or isometric view similar to FIG. 97, showing the retrieval system engaging the valve, with the delivery system retracted.
Figure 99:
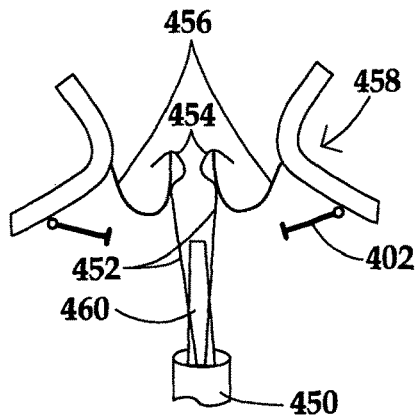
FIG. 99 is a schematic perspective or isometric view similar to FIG. 98, showing a pair of leaflet-capture tethers or the retrieval system shifted apart to engage and curl or otherwise engage and/or retract the leaflets

Upon an opening of the natural valve 458 as depicted in FIG. 95, valve retrieval system 448 is moved in a distal direction and inserted trough the open valve, as depicted in FIG. 96. The natural valve then closes over valve retrieval system 448 as shown in FIG. 97. At that juncture, valve retrieval system 448 is slightly retracted so that the hooks or barbs 454 are juxtaposed to the valve leaflets 456 as indicated in FIG. 98. Tethers 452 and tether guide member 460 are then manipulated to insert hooks or barbs 454 into valve leaflets 456. As indicated in FIG. 99, the distal ends of tethers 452 including hooks or barbs 454 shift laterally or outwardly to capture and entrain leaflets 456. This movement of tethers 452 is implemented via tether guide member 460. To that end, the grooves or channels in tether guide member 460 that guide tethers 452 may be formed with camming surfaces such as humps that move the tethers laterally outwardly upon a longitudinal shifting of the guide member 460 relative to the tethers.

Figure 100:
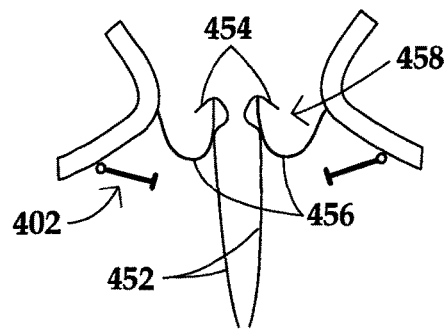
FIG. 100 is a schematic perspective or isometric view similar to FIG. 99, showing the retrieval system delivery apparatus removed.
Figure 101:
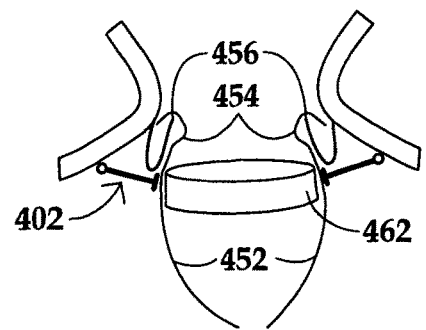
FIG. 101 is a view similar to FIG. 100, showing the tethers of the retrieval system drawn through a valve-receiving neo-annulus or aperture of a valve-support scaffold as a prosthetic valve is deployed into the neo-annulus of the scaffold.
Figure 102:
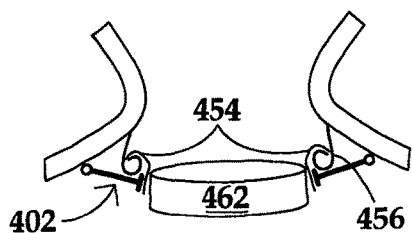
FIG. 102 is a view similar to FIG. 101, showing the tethers of the valve retrieval system completely engaged with the valve leaflets and fixing the leaflets to the valve-support scaffold as well as to the implanted prosthetic valve.
Figure 103:
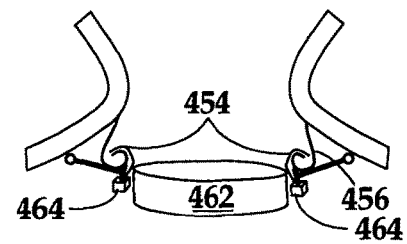
FIG. 103 is a view similar to FIG. 101, showing the native valve leaflets fully retracted and attached to the scaffold and the prosthetic heart valve and with locking apparatuses connected on the tethers of the heart valve retrieval system to reinforce fixation of those tethers to the scaffold and the deployed prosthetic valve.

After the ensnaring or snagging of leaflets 456 by hooks or barbs 454, catheter 450 and tether guide member 460 are withdrawn, as shown in FIG. 100. Then, as depicted in FIG. 101, prosthetic valve 462 is inserted inside a ring of tethers 452 so that the leaflet-entraining tethers are clamped between neo-annulus 424 of scaffold 402 and the prosthetic valve. Tethers 452 are further retracted at that juncture to curl leaflets 456 and constrain them about the margin 420 of scaffold 402, as illustrated in FIG. 102. Then tethers 452 are severed (FIG. 102) and locks 464 are attached to the severed tether ends (FIG. 103).

Figure 104:
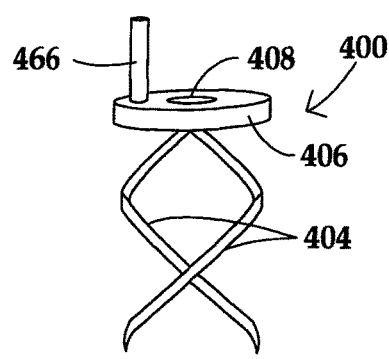
FIG. 104 is a schematic perspective or isometric view of the helical fixation device or fastener of FIG. 81, showing a pin disposed in a cap of the helical fixation device, which, when advanced into the heart or blood vessel wall, prohibits untwisting of the helical fastener.
Figure 105:
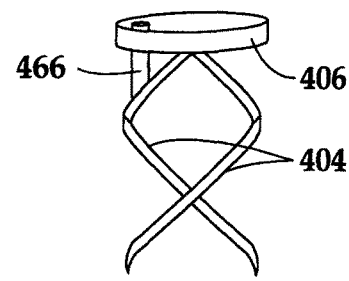
FIG. 105 is a view similar to FIG. 104, showing the pin in a deployed or advanced position.

As illustrated in FIGS. 104 and 105, fastener 400 may be provided with a pin 466 movably coupled to cap 406 for enabling a locking of the fastener to heart chamber or vessel wall 414. Upon completed insertion of prongs 404 into heart chamber or vessel wall 414, pin 466 is moved from a retracted neutral position (FIG. 104) to an advanced locking position (FIG. 105). In its advanced position, pin 466 prevents fastener 400 from rotating or untwisting from its inserted position clamping margin 420 to the heart or vessel wall.

FIG. 106 shows how delivery catheter 426 has a steerable distal end 468 which may assume any of a plurality of orientations 468a, 468b, etc. relative to a main body 470 of the catheter, thereby facilitating a placement of scaffold 402.

FIG. 107 depicts a distal end portion of a leaflet entrainment device 472 having four hooks or barbs 474 that are actively or passively released when engaged with a valve leaflet or cord.

FIG. 108 depicts a leaflet entrainment device 476 with two subassemblies 478 and 480 including respective tubular delivery members 482 and 484 and pairs of hooks or barbs, 486 and 488. Tubular delivery members 482 and 484 are spring biased to separate as illustrated after emergence from a delivery catheter 490.

FIGS. 109-113 depict a series of steps similar to those described hereinabove with reference to FIGS. 94-103, applied in a retrograde procedure to capture leaflets 500 of an aortic valve 502 and attach the captured leaflets to an implanted scaffold 504 and a prosthetic valve 506 which is seated in a neo-annulus 508 of the scaffold. The procedure of FIGS. 109-113 is particularly pertinent in solving a problem called "aortic insufficiency" where there is no calcium, so, like as in the case of the mitral valve, an expanding, radial-force valve cannot be used. This disease is a common occurrence as a result of LVAD (left ventricular assist device) placement.

Figure 109:
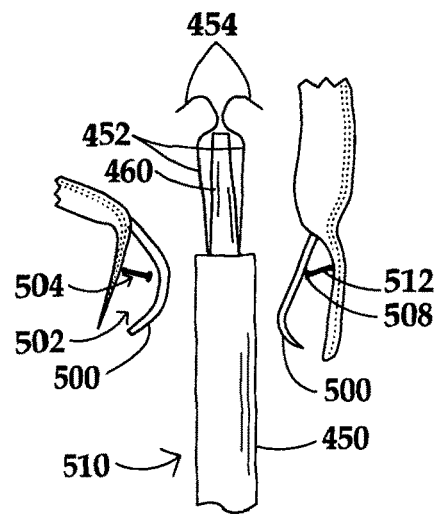
FIG. 109 is a schematic perspective or isometric view of a valve retrieval system inserted in a retrograde direction through an opened aortic valve.

As shown in FIG. 109, a valve retrieval system 510 which is similar if not identical to system 448, comprises the same components, namely, introducer catheter 450 and tethers 452 with capture hooks or barbs 454 at the free ends thereof. Hooks or barbs 454 are effective in the procedure of FIGS. 109-113 to entrain leaflets 500 of aortic valve 502. Again, tether guide member 460 maintains tethers 452 in a suitably arranged or distributed array. Valve retrieval system 448 is inserted into the aorta after the installation of valve-supporting scaffold 502 and prior to the seating of prosthetic valve 506 in neo-annulus 508.

Figure 110:
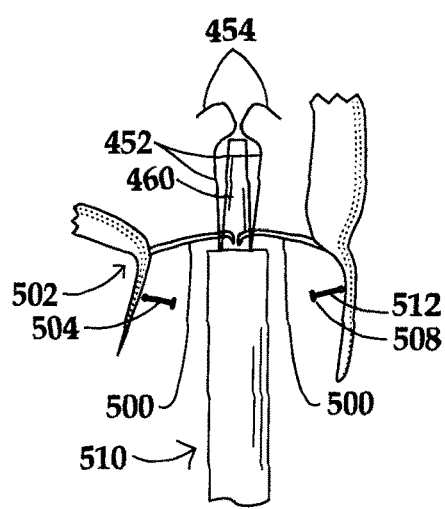
FIG. 110 is a schematic perspective or isometric view similar to FIG. 109, showing the aortic valve closed around the valve retrieval system.
Figure 111:
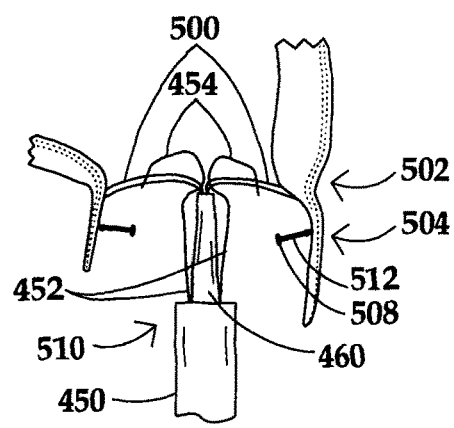
FIG. 111 is a schematic perspective or isometric view similar to FIGS. 109 and 110, showing the retrieval system engaging the valve.
Figure 112:
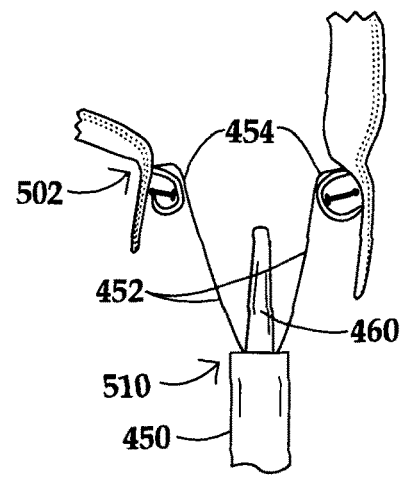
FIG. 112 is a schematic perspective or isometric view similar to FIGS. 109-111, showing a pair of leaflet-capture tethers or the retrieval system shifted apart and engaging and curling the leaflets.

Upon an opening of the aortic valve 502 as depicted in FIG. 109, valve retrieval system 448 is moved retrograde in the aorta (not separately labeled) and inserted through the open valve, as depicted. The aortic valve 502 then closes over valve retrieval system 448 as shown in FIG. 110. At that juncture, valve retrieval system 448 is slightly retracted so that the hooks or barbs 454 are juxtaposed to the valve leaflets 500 as indicated in FIG. 111. Tethers 452 and tether guide member 460 are then manipulated to insert hooks or barbs 454 into valve leaflets 500. As indicated in FIG. 112, the distal ends of tethers 452 including hooks or barbs 454 shift laterally or outwardly to capture and entrain leaflets 500. This movement of tethers 452 is implemented via tether guide member 460, as described above with references to FIGS. 94-103.

Figure 113:
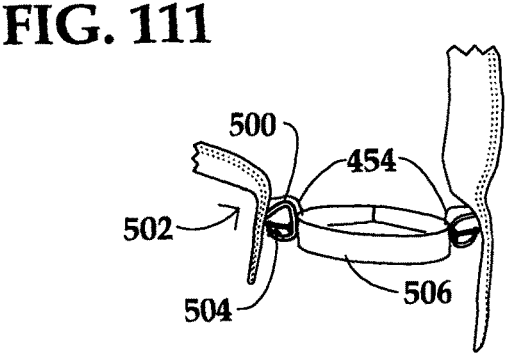
FIG. 113 is a schematic perspective or isometric view similar to FIGS. 109-112, showing the retrieval system delivery apparatus removed the tethers of the retrieval system drawn through a valve-receiving neo-annulus or aperture of a valve-support scaffold, and a prosthetic valve deployed into the neo-annulus of the scaffold.

After the ensnaring or snagging of aortic leaflets 500 by hooks or barbs 454, catheter 450 and tether guide member 460 are withdrawn, prosthetic valve 506 is inserted inside a ring of tethers 452 so that the leaflet-entraining tethers are clamped between neo-annulus 508 of scaffold 502 and the prosthetic valve. Tethers 452 are further retracted at that juncture to curl leaflets 456 and constrain them about the margin 512 of scaffold 502, as illustrated in FIG. 113. Then tethers 452 are severed. Locks 464 may be attached to the severed tether ends, as discussed hereinabove with reference to FIG. 103.

In another approach constituting a variation of the procedure described hereinabove with reference to FIGS. 1-30, a scaffold or valve support device with a central orifice defining annulus and a preferably flexible margin or perimeter element is attached to the atrial wall. One then waits a few (3-6) weeks for tissue growth to bind the scaffold or valve support device to the atrial wall. At that juncture a prosthetic or bioprosthetic valve is seated in the orifice.

Accordingly, fastening elements are provided herein or in U.S. Patent Application Publication No. 2010/0262232 and International Patent Application No. PCT/US2010/001077 for attaching said scaffold or valve support device either (1) to heart or blood vessel tissue adjacent to a native heart valve, (2) at least indirectly to leaflets of a native valve of a patient, or (3) to both adjacent tissue and directly or indirectly to heart valve tissue. Preferably, the attachment is such that the scaffold or valve support device potentially is in effective force-transmitting and effective perivulvular fluid-sealing contact with the target native valve and substantially fixedly attached to the patient.

Although the invention has been described in terms of particular embodiments and applications, one of ordinary skill in the art, in light of this teaching, can generate additional embodiments and modifications without departing from the spirit of or exceeding the scope of the claimed invention. For instance, instead of being attached directly to the valve leaflets VL1 and VL2, neo-annulus/replacement valve complex 36 of suitable dimensions may be attached in whole or in part to the cardio-vascular wall CVW about native valve HV. Accordingly, it is to be understood that the drawings and descriptions herein are proffered by way of example to facilitate comprehension of the invention and should not be construed to limit the scope thereof.

What is claimed is:

1. A surgical method for use in heart repair in a subject, comprising:
    providing an implantable scaffold including:
        an inner margin element defining an orifice for receiving or seating a prosthetic or bio-prosthetic valve, and
        a flexible outer margin element surrounding said inner margin element, said outer margin element and said inner margin element being different from one another and spaced in their entireties from one another, said outer margin element and said inner margin element being coplanar with one another in an expanded non-deformed pre-attachment configuration of said scaffold;
    disposing said scaffold in said expanded non-deformed pre-attachment configuration inside a vascular system of a patient;
    maneuvering said scaffold into position near a natural or native valve of the vascular system of the patient, the maneuvering of said expanded scaffold including manipulating a plurality of tethers or wires extending to said outer margin element, said manipulator tethers or wires being detachably connected at their distal ends directly to said outer margin element;
    individually or independently manipulating said manipulator tethers or wires to deform said outer margin element so as to conform said outer margin element to an irregular internal wall surface of said vascular system;
    attaching said outer margin element to said internal wall surface, the attaching of said outer margin element including applying at least one fastener or fixation mechanism to said outer margin element and said internal wall surface so that said outer margin element conforms to said internal wall surface; and
    upon the attaching of said outer margin element, detaching said manipulator tethers or wires from said outer margin element and concomitantly from said scaffold.

2. The method of claim 1 wherein the disposing of said scaffold includes:
    inserting a catheter into a vascular system of a patient, said scaffold being disposed in a collapsed configuration in said catheter; and
    thereafter ejecting said scaffold from a distal end of said catheter, said scaffold expanding from said collapsed configuration to said expanded non-deformed pre-attachment configuration.

3. The method of claim 2 wherein said manipulator tethers or wires extend within said delivery catheter.

4. The method of claim 1 wherein said at least one fastener or fixation mechanism includes a plurality of fasteners at mutually spaced locations about or along said outer margin element, the applying of said fasteners creating a continuous or near continuous contact between said internal tissue surface and said scaffold all along said outer margin element.

5. The method of claim 1 wherein said at least one fastener or fixation mechanism includes an element taken from the group consisting of an expandable stent-like framework, an inflatable ring-component, springs, tissue adhesive, magnets, penetrating hooks, and barbs.

6. The method of claim 1 wherein said scaffold includes a membrane extending between said outer margin element and said inner margin element.

7. The method of claim 6 wherein said membrane tents away from one side of said scaffold, to provide a space between said scaffold and a native valve.

8. The method of claim 1, further comprising disposing a prosthetic valve within said inner margin element so that said prosthetic valve is attached to said scaffold.

9. The method of claim 8, further comprising coupling said scaffold to sub-valvular apparatus of a native heart valve, the coupling including clamping a tether between said prosthetic valve and said inner margin element, said tether being attached to said sub-valvular apparatus.

10. The method of claim 1, further comprising securing said scaffold to cordae tendenae of the patient's heart, the securing including threading at least one tether element about the cordae tendenae, drawing said at least one tether element through said orifice defined by said inner margin element, and seating a prosthetic or bio-prosthetic valve in said orifice so that so that said at least one tether element is clamped between said inner margin element and said prosthetic or bio-prosthetic valve.

11. A surgical method for use in heart repair in a subject, comprising:
providing an implantable scaffold including:
an inner margin element defining an orifice for receiving or seating a prosthetic or bio-prosthetic valve, and
a flexible outer margin element surrounding said inner margin element, said outer margin element and said inner margin element being different from one another and spaced in their entireties from one another, said outer margin element and said inner margin element being coplanar with one another in an expanded non-deformed pre-attachment configuration of said scaffold;
inserting a catheter into a vascular system of a patient, said scaffold being disposed in a collapsed configuration in said catheter;
thereafter ejecting said scaffold from a distal end of said catheter, said scaffold expanding from said collapsed configuration to said expanded non-deformed pre-attachment configuration;
maneuvering the expanded scaffold into position near a natural or native valve of the vascular system of the patient, the maneuvering of said expanded scaffold including manipulating a plurality of tethers or wires extending through said catheter to said outer margin element, said manipulator tethers or wires being detachably connected at their distal ends directly to said outer margin element;
individually or independently manipulating said manipulator tethers or wires to deform said outer margin element so as to conform said outer margin element to an irregular internal wall surface of said vascular system;
attaching said outer margin element in a conforming configuration to said internal wall surface, the attaching of said outer margin element including applying a plurality of fasteners at spaced locations about said outer margin element; and
upon the attaching of said outer margin element, detaching said manipulator tethers or wires from said outer margin element and concomitantly from said scaffold.

12. The method of claim 11 wherein said fasteners each include an element taken from the group consisting of an expandable stent-like framework, an inflatable ring-component, springs, tissue adhesive, magnets, penetrating hooks, and barbs.

13. The method of claim 11 wherein said scaffold includes a membrane extending between said outer margin element and said inner margin element.

14. The method of claim 13 wherein said membrane tents away from one side of said scaffold, to provide a space between said scaffold and a native valve.

15. The method of claim 11, further comprising disposing a prosthetic valve within said inner margin element so that said prosthetic valve is attached to said scaffold.

16. The method of claim 15, further comprising coupling said scaffold to sub-valvular apparatus of a native heart valve, the coupling including clamping a tether between said prosthetic valve and said inner margin element, said tether being attached to said sub-valvular apparatus.

17. The method of claim 11, further comprising securing said scaffold to cordae tendenae of the patient's heart, the securing including threading at least one tether element about the cordae tendenae, drawing said at least one tether element through said orifice defined by said inner margin element, and seating a prosthetic or bio-prosthetic valve in said orifice so that so that said at least one tether element is clamped between said inner margin element and said prosthetic or bio-prosthetic valve.

* * * * *